US008062250B2

(12) United States Patent
Mogensen et al.

(10) Patent No.: US 8,062,250 B2
(45) Date of Patent: Nov. 22, 2011

(54) CANNULA DEVICE

(75) Inventors: Lasse Wesltoft Mogensen, Søborg (DK); Magnus Walter Göransson, Malmö (SE)

(73) Assignee: Unomedical A/S, Birkeroed (DK)

( * ) Notice: Subject to any disclaimer, the term of this patent is extended or adjusted under 35 U.S.C. 154(b) by 2083 days.

(21) Appl. No.: 11/023,840

(22) Filed: Dec. 23, 2004

(65) Prior Publication Data
US 2006/0036214 A1 Feb. 16, 2006

Related U.S. Application Data

(60) Provisional application No. 60/600,209, filed on Aug. 10, 2004.

(51) Int. Cl.
*A61M 31/00* (2006.01)
(52) U.S. Cl. ..................................... 604/93.01
(58) Field of Classification Search ............... 604/93.01
See application file for complete search history.

(56) References Cited

U.S. PATENT DOCUMENTS

| | | |
|---|---|---|
| 643,544 A | 2/1900 | Simmons |
| 1,592,462 A | 7/1926 | MacGregor |
| 1,838,825 A | 1/1929 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapata |
| 2,952,420 A | 9/1960 | Von Hoorn |
| 2,972,779 A | 2/1961 | Cowley |
| 3,055,361 A | 9/1962 | Ballard |
| 3,059,802 A | 10/1962 | Mitchell |
| 3,074,541 A | 1/1963 | Roehr |
| 3,107,785 A | 10/1963 | Roehr |

(Continued)

FOREIGN PATENT DOCUMENTS
DE 893 296 12/1953
(Continued)

OTHER PUBLICATIONS

"Why inset®?" inset® infusion set product overview; http://web.archive.org/web/20040906102448/http://www.infusion-set.com/Default.asp?ID=108; two pages.

*Primary Examiner* — Nicholas D Lucchesi
*Assistant Examiner* — Diva Ranade
(74) *Attorney, Agent, or Firm* — Brinks Hofer Gilson & Lione

(57) ABSTRACT

A cannula device for infusion sets is provided. The cannula device includes a housing and at least one membrane mounted to the housing and adapted for receiving a piercing member of a connector. The cannula device further includes a cannula mounted to the housing. The cannula device is adapted to removably attach to a base part of an infusion set. The cannula device can receive the piercing member from a first receiving direction and from a second receiving direction different from the first receiving direction, providing fluid communication between the piercing member and the cannula mounted to the housing.

28 Claims, 60 Drawing Sheets

U.S. PATENT DOCUMENTS

| | | |
|---|---|---|
| 3,154,080 A | 10/1964 | Rowan et al. |
| 3,221,739 A | 12/1965 | Rosenthal |
| 3,221,740 A | 12/1965 | Rosenthal |
| 3,306,291 A | 2/1967 | Burke |
| 3,317,166 A | 5/1967 | Janssen |
| 3,485,352 A | 12/1969 | Pilger |
| 3,509,879 A | 5/1970 | Bathish et al. |
| 3,519,158 A | 7/1970 | Anderson |
| 3,545,286 A | 12/1970 | Stenstrom |
| 3,547,119 A | 12/1970 | Hall et al. |
| 3,610,240 A | 10/1971 | Harautuneian |
| 3,648,999 A | 3/1972 | Bauer |
| 3,670,727 A | 6/1972 | Reiterman |
| 3,783,895 A | 1/1974 | Weichselbaum |
| 3,783,996 A | 1/1974 | Gerard et al. |
| 3,788,374 A | 1/1974 | Saijo |
| 3,810,469 A | 5/1974 | Hurschman |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,893,448 A | 7/1975 | Brantigan |
| 3,937,219 A | 2/1976 | Karakashian |
| 3,942,528 A | 3/1976 | Loeser |
| 3,986,507 A | 10/1976 | Watt |
| 3,986,508 A | 10/1976 | Barrington |
| 3,995,518 A | 12/1976 | Spiroff |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,306,705 A | 12/1981 | Svensson |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,365,630 A | 12/1982 | McFarlane |
| 4,378,015 A | 3/1983 | Wardlaw |
| 4,400,861 A | 8/1983 | Parker |
| 4,406,042 A | 9/1983 | McPhee |
| 4,415,393 A | 11/1983 | Grimes |
| 4,417,886 A | 11/1983 | Frankhouser et al. |
| 4,458,344 A | 7/1984 | Coogler |
| 4,464,178 A | 8/1984 | Dalton |
| 4,472,024 A | 9/1984 | Konomura et al. |
| 4,473,369 A | 9/1984 | Lueders et al. |
| 4,484,910 A | 11/1984 | Sarnoff et al. |
| 4,500,312 A | 2/1985 | McFarlane |
| 4,517,971 A | 5/1985 | Sorbonned |
| 4,525,157 A | 6/1985 | Vaillancourt |
| 4,530,695 A | 7/1985 | Phillips et al. |
| 4,531,686 A | 7/1985 | Shaw |
| 4,531,937 A | 7/1985 | Yates |
| 4,563,177 A | 1/1986 | Kamen |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,617,019 A | 10/1986 | Fecht |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A * | 7/1988 | Konopka et al. ......... 604/167.02 |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,129,884 A | 7/1992 | Dysarz |
| 5,134,593 A | 7/1992 | Logan et al. |
| 5,134,594 A | 7/1992 | Woo |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,314 A | 2/1993 | Peters |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |

| Patent | Date | Name |
|---|---|---|
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,487,506 A | 1/1996 | Drummond et al. |
| 5,490,841 A | 2/1996 | Landis |
| 5,492,313 A | 2/1996 | Pan et al. |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,519,167 A | 5/1996 | Kunimoto et al. |
| 5,520,654 A | 5/1996 | Wahlberg |
| 5,522,803 A | 6/1996 | Teissen-Simony |
| 5,527,287 A | 6/1996 | Miskinyar et al. |
| 5,533,974 A | 7/1996 | Gaba |
| 5,540,709 A | 7/1996 | Ramel |
| 5,545,143 A * | 8/1996 | Fischell ............ 604/180 |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,516 A | 1/1998 | Peterson et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| D402,538 S | 12/1998 | Wagter et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,873,540 A | 2/1999 | Hardin |
| 5,899,886 A | 5/1999 | Cosme |
| 5,911,705 A | 6/1999 | Howell |
| 5,913,846 A | 6/1999 | Szabo |
| 5,915,640 A | 6/1999 | Wagter et al. |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,947,931 A | 9/1999 | Bierman |
| 5,947,935 A | 9/1999 | Rinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,968,011 A | 10/1999 | Larsen et al. |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| 5,992,787 A | 11/1999 | Burke |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 * | 10/2001 | Marggi ............ 604/174 |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,379,335 B1 | 4/2002 | Rigon et al. |
| D456,692 S | 5/2002 | Epstein |
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |

| | | | | | | |
|---|---|---|---|---|---|---|
| D472,316 S | 3/2003 | Douglas et al. | 7,569,262 B2 | 8/2009 | Szabo et al. | |
| D472,630 S | 4/2003 | Douglas et al. | 7,648,494 B2 | 1/2010 | Kornerup et al. | |
| 6,572,586 B1 | 6/2003 | Wojcik | 7,766,867 B2 | 8/2010 | Lynch et al. | |
| 6,579,267 B2 * | 6/2003 | Lynch et al. ............... 604/174 | 2001/0004970 A1 | 6/2001 | Hollister et al. | |
| 6,582,397 B2 | 6/2003 | Alesi et al. | 2001/0016714 A1 | 8/2001 | Bell et al. | |
| 6,595,962 B1 | 7/2003 | Perthu | 2001/0021827 A1 | 9/2001 | Ferguson et al. | |
| 6,607,509 B2 | 8/2003 | Bobroff et al. | 2001/0039387 A1 | 11/2001 | Rutynowski et al. | |
| 6,607,511 B2 | 8/2003 | Halseth et al. | 2001/0039401 A1 | 11/2001 | Ferguson et al. | |
| 6,613,064 B2 | 9/2003 | Rutynowski et al. | 2001/0041875 A1 | 11/2001 | Higuchi et al. | |
| 6,620,133 B1 | 9/2003 | Steck | 2001/0049496 A1 | 12/2001 | Kirchhofer | |
| 6,620,136 B1 | 9/2003 | Pressly, Sr. et al. | 2001/0053889 A1 | 12/2001 | Marggi | |
| 6,620,140 B1 | 9/2003 | Metzger | 2001/0056284 A1 | 12/2001 | Purcell et al. | |
| 6,629,949 B1 | 10/2003 | Douglas | 2002/0022798 A1 | 2/2002 | Connelly | |
| 6,645,181 B1 | 11/2003 | Lavi et al. | 2002/0022855 A1 | 2/2002 | Bobroff et al. | |
| 6,645,182 B1 | 11/2003 | Szabo | 2002/0026152 A1 | 2/2002 | Bierman | |
| 6,659,982 B2 | 12/2003 | Douglas et al. | 2002/0055711 A1 | 5/2002 | Lavi et al. | |
| 6,685,674 B2 | 2/2004 | Douglas et al. | 2002/0068904 A1 | 6/2002 | Pluth et al. | |
| 6,699,218 B2 | 3/2004 | Flaherty et al. | 2002/0072720 A1 * | 6/2002 | Hague et al. ............... 604/264 | |
| 6,702,779 B2 | 3/2004 | Connelly et al. | 2002/0074345 A1 | 6/2002 | Scheider et al. | |
| 6,726,649 B2 | 4/2004 | Swenson et al. | 2002/0077599 A1 | 6/2002 | Wojcik | |
| 6,736,797 B1 * | 5/2004 | Larsen et al. ............ 604/167.05 | 2002/0082543 A1 | 6/2002 | Park et al. | |
| 6,749,587 B2 | 6/2004 | Flaherty | 2002/0107489 A1 | 8/2002 | Lee | |
| 6,749,589 B1 | 6/2004 | Douglas et al. | 2002/0111581 A1 | 8/2002 | Sasso | |
| 6,755,805 B1 | 6/2004 | Reid | 2002/0145073 A1 | 10/2002 | Swanson | |
| 6,776,775 B1 | 8/2004 | Mohammad | 2002/0156424 A1 | 10/2002 | Suzuki et al. | |
| 6,790,199 B1 | 9/2004 | Gianakos | 2002/0156427 A1 | 10/2002 | Suzuki et al. | |
| 6,805,686 B1 | 10/2004 | Fathallah et al. | 2002/0161322 A1 | 10/2002 | Utterberg et al. | |
| 6,808,506 B2 | 10/2004 | Lastovich et al. | 2002/0161332 A1 | 10/2002 | Ramey | |
| 6,811,545 B2 | 11/2004 | Vaillancourt | 2002/0161386 A1 | 10/2002 | Halseth et al. | |
| 6,814,720 B2 | 11/2004 | Olsen et al. | 2002/0165493 A1 | 11/2002 | Bierman | |
| 6,824,530 B2 | 11/2004 | Wagner et al. | 2002/0169419 A1 | 11/2002 | Steg | |
| 6,824,531 B1 | 11/2004 | Zecha, Jr. et al. | 2002/0173748 A1 | 11/2002 | McConnell et al. | |
| 6,830,562 B2 | 12/2004 | Mogensen et al. | 2002/0173769 A1 | 11/2002 | Gray et al. | |
| 6,837,877 B2 | 1/2005 | Zurcher | 2002/0183688 A1 | 12/2002 | Lastovich et al. | |
| 6,837,878 B2 | 1/2005 | Smutney et al. | 2002/0189688 A1 | 12/2002 | Roorda | |
| 6,840,922 B2 | 1/2005 | Nielsen et al. | 2002/0193737 A1 | 12/2002 | Popovsky | |
| 6,880,701 B2 | 4/2005 | Bergeron et al. | 2002/0193744 A1 | 12/2002 | Alesi et al. | |
| 6,916,017 B2 | 7/2005 | Noe | 2003/0014018 A1 | 1/2003 | Giambattista et al. | |
| 6,923,791 B2 * | 8/2005 | Douglas ............... 604/167.05 | 2003/0060781 A1 | 3/2003 | Mogensen et al. | |
| 6,926,694 B2 | 8/2005 | Marano-Ford et al. | 2003/0069548 A1 | 4/2003 | Connelly et al. | |
| 6,939,331 B2 | 9/2005 | Ohshima | 2003/0088238 A1 | 5/2003 | Poulsen et al. | |
| 6,949,084 B2 * | 9/2005 | Marggi et al. ............... 604/174 | 2003/0105430 A1 | 6/2003 | Lavi et al. | |
| 6,959,812 B2 | 11/2005 | Reif et al. | 2003/0109829 A1 | 6/2003 | Mogensen et al. | |
| 6,960,193 B2 | 11/2005 | Rosenberg | 2003/0125669 A1 | 7/2003 | Safabash et al. | |
| 6,979,316 B1 | 12/2005 | Rubin et al. | 2003/0125678 A1 | 7/2003 | Swenson et al. | |
| 6,991,619 B2 | 1/2006 | Marano-Ford et al. | 2003/0130619 A1 | 7/2003 | Safabash et al. | |
| 6,991,620 B2 | 1/2006 | Marano-Ford et al. | 2003/0139704 A1 | 7/2003 | Lin | |
| 6,994,213 B2 | 2/2006 | Giard et al. | 2003/0158520 A1 | 8/2003 | Safabash et al. | |
| 6,997,907 B2 | 2/2006 | Safabash et al. | 2003/0176843 A1 | 9/2003 | Wilkinson | |
| 7,014,625 B2 | 3/2006 | Bengtsson | 2003/0176852 A1 | 9/2003 | Lynch et al. | |
| 7,018,344 B2 | 3/2006 | Bressler et al. | 2003/0181863 A1 | 9/2003 | Davis et al. | |
| 7,022,108 B2 | 4/2006 | Marano-Ford et al. | 2003/0181868 A1 | 9/2003 | Swenson | |
| 7,047,070 B2 | 5/2006 | Wilkenson et al. | 2003/0181873 A1 | 9/2003 | Swenson | |
| 7,052,483 B2 | 5/2006 | Wojcik | 2003/0181874 A1 | 9/2003 | Bressler et al. | |
| 7,055,713 B2 | 6/2006 | Rea et al. | 2003/0187394 A1 | 10/2003 | Wilkinson et al. | |
| 7,056,302 B2 | 6/2006 | Douglas | 2003/0187395 A1 | 10/2003 | Wilkinson et al. | |
| 7,070,580 B2 | 7/2006 | Nielsen | 2003/0199823 A1 | 10/2003 | Bobroff et al. | |
| 7,074,208 B2 | 7/2006 | Pajunk et al. | 2003/0216686 A1 | 11/2003 | Lynch et al. | |
| D526,409 S | 8/2006 | Nielsen et al. | 2003/0220610 A1 | 11/2003 | Lastovich et al. | |
| 7,083,592 B2 | 8/2006 | Lastovich et al. | 2003/0225373 A1 | 12/2003 | Bobroff et al. | |
| 7,083,597 B2 | 8/2006 | Lynch et al. | 2003/0225374 A1 | 12/2003 | Mathiasen | |
| 7,097,631 B2 | 8/2006 | Trautman et al. | 2003/0229308 A1 | 12/2003 | Tsals et al. | |
| 7,109,878 B2 | 9/2006 | Mann et al. | 2003/0229316 A1 | 12/2003 | Hwang et al. | |
| 7,115,108 B2 | 10/2006 | Wilkenson et al. | 2004/0002682 A1 | 1/2004 | Kovelman et al. | |
| 7,115,112 B2 | 10/2006 | Mogensen et al. | 2004/0006316 A1 * | 1/2004 | Patton ............... 604/244 | |
| 7,141,023 B2 | 11/2006 | Diermann et al. | 2004/0026840 A1 | 2/2004 | Eckel et al. | |
| 7,147,623 B2 | 12/2006 | Mathiasen | 2004/0044306 A1 * | 3/2004 | Lynch et al. ............... 604/93.01 | |
| 7,186,236 B2 | 3/2007 | Gibson et al. | 2004/0049159 A1 | 3/2004 | Barrus et al. | |
| 7,211,068 B2 | 5/2007 | Douglas | 2004/0059316 A1 | 3/2004 | Smedegaard | |
| 7,214,207 B2 | 5/2007 | Lynch et al. | 2004/0068231 A1 | 4/2004 | Blondeau | |
| 7,214,215 B2 | 5/2007 | Heinzerling et al. | 2004/0069044 A1 | 4/2004 | Lavi et al. | |
| 7,250,037 B2 | 7/2007 | Shermer et al. | 2004/0087913 A1 | 5/2004 | Rogers et al. | |
| 7,258,680 B2 | 8/2007 | Mogensen et al. | 2004/0092865 A1 | 5/2004 | Flaherty et al. | |
| D554,253 S | 10/2007 | Kornerup | 2004/0092875 A1 | 5/2004 | Kochamba | |
| 7,303,543 B1 | 12/2007 | Maule et al. | 2004/0111068 A1 | 6/2004 | Swenson | |
| 7,309,326 B2 | 12/2007 | Fangrow, Jr. | 2004/0112781 A1 | 6/2004 | Hofverberg et al. | |
| 7,407,491 B2 | 8/2008 | Fangrow, Jr. | 2004/0116865 A1 | 6/2004 | Bengtsson | |
| 7,407,493 B2 | 8/2008 | Cane' | 2004/0133164 A1 | 7/2004 | Funderburk et al. | |
| 7,431,876 B2 | 10/2008 | Mejlhede et al. | 2004/0138612 A1 | 7/2004 | Shermer et al. | |

| | | |
|---|---|---|
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1* | 8/2004 | Hunn et al. ............. 604/164.01 |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1* | 5/2005 | Marrs et al. .................. 604/506 |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1* | 2/2006 | Mogensen et al. ....... 604/164.01 |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0066955 A1 | 3/2007 | Sparholt et al. |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2008/0312601 A1 | 12/2008 | Cane' |
| 2010/0004597 A1 | 1/2010 | Gyrn et al. |
| 2010/0137829 A1 | 6/2010 | Nielsen et al. |
| 2010/0228226 A1 | 9/2010 | Nielsen |

FOREIGN PATENT DOCUMENTS

| | | |
|---|---|---|
| DE | 1 053 541 | 3/1959 |
| DE | 26 20 009 A1 | 12/1977 |
| DE | 28 03 509 | 8/1979 |
| DE | 28 03 509 A | 8/1979 |
| DE | 37 15 965 A | 1/1988 |
| DE | 4 342 329 A1 | 6/1994 |
| DE | 196 31 921 | 3/1997 |
| DE | 298 18 311 U1 | 3/1999 |
| DE | 299 05 072 U1 | 9/1999 |
| DE | 298 18 311 U1 | 11/1999 |
| DE | 19847143 A1 | 1/2000 |
| DE | 101 06 074 A1 | 9/2000 |
| DE | 299 21 406 | 1/2001 |
| DE | 101 06 074 A1 | 6/2002 |
| DE | 101 17 285 A1 | 11/2002 |
| DE | 299 21 406 U1 | 11/2002 |
| DE | 203 20 207 U1 | 11/2004 |
| DK | DE 37 22 893 C1 | 6/1988 |
| DK | DE 38 23 447 | 2/1996 |
| DK | DE 196 10 692 A1 | 9/1997 |
| DK | DE 198 47 143 A1 | 1/2000 |
| DK | DE 100 49 001 A1 | 4/2002 |
| EP | 01176232 B1 | 9/1984 |
| EP | 0 188 014 B1 | 10/1985 |
| EP | 0 239 244 B1 | 2/1987 |
| EP | 0272530 A2 | 6/1988 |
| EP | 0 298 521 B1 | 9/1990 |
| EP | 0451040 A1 | 10/1991 |
| EP | 0 184 231 B1 | 1/1992 |
| EP | 0 475 857 | 3/1992 |
| EP | 0 544 837 B1 | 6/1993 |
| EP | 0 633 039 | 7/1994 |
| EP | 0615768 A2 | 9/1994 |
| EP | 0 651 662 B1 | 5/1995 |
| EP | 0652027 A1 | 5/1995 |
| EP | 0657184 A1 | 6/1995 |
| EP | 0 714 631 B1 | 6/1996 |
| EP | 744 183 A2 | 11/1996 |
| EP | 0 747 006 A1 | 12/1996 |
| EP | 0799626 A1 | 10/1997 |
| EP | 0 688 232 B1 | 12/1998 |
| EP | 0 884 108 A1 | 12/1998 |
| EP | 0 916 361 A1 | 5/1999 |
| EP | 0 931 560 A1 | 7/1999 |
| EP | 0937475 A2 | 8/1999 |
| EP | 0 956 879 A1 | 11/1999 |
| EP | 1 045 145 A1 | 10/2000 |
| EP | 1 060 757 A1 | 12/2000 |
| EP | 1 086 718 A | 3/2001 |
| EP | 1 125 593 A1 | 8/2001 |

| | | | | | | |
|---|---|---|---|---|---|---|
| EP | 1 167 765 | A2 | 1/2002 | WO | WO 01/72353 A2 | 10/2001 |
| EP | 0 775 501 | | 6/2002 | WO | WO 01/76684 A1 | 10/2001 |
| EP | 0 894 216 | B1 | 7/2003 | WO | WO 01/81785 A1 | 11/2001 |
| EP | 1329233 | B1 | 7/2003 | WO | WO 01/93926 A2 | 12/2001 |
| EP | 1350537 | A1 | 10/2003 | WO | WO 02/02165 A2 | 1/2002 |
| EP | 1360970 | A1 | 11/2003 | WO | WO 02/07804 A1 | 1/2002 |
| EP | 1 380 315 | A1 | 1/2004 | WO | WO 02/40083 A2 | 5/2002 |
| EP | 1407747 | A1 | 4/2004 | WO | WO 02/46080 | 6/2002 |
| EP | 1407793 | A1 | 4/2004 | WO | WO 02/053220 A2 | 7/2002 |
| EP | 1421968 | A2 | 5/2004 | WO | WO 02/066854 A1 | 8/2002 |
| EP | 0 956 879 | A1 | 7/2004 | WO | WO 02/068014 | 9/2002 |
| EP | 1177802 | B1 | 9/2004 | WO | WO 02/081012 A2 | 10/2002 |
| EP | 1475113 | A1 | 11/2004 | WO | WO 02/081013 A2 | 10/2002 |
| EP | 1495775 | A1 | 1/2005 | WO | WO 02/083206 A2 | 10/2002 |
| EP | 1502613 | A1 | 2/2005 | WO | WO 02/094352 | 11/2002 |
| EP | 1525873 | A1 | 4/2005 | WO | WO 02/100457 | 12/2002 |
| EP | 1527792 | A1 | 5/2005 | WO | WO 02/102442 A1 | 12/2002 |
| EP | 1616594 | A1 | 1/2006 | WO | WO 03/015860 A1 | 2/2003 |
| EP | 1704889 | A1 | 9/2006 | WO | WO 03/026728 | 4/2003 |
| EP | 1762259 | A1 | 3/2007 | WO | WO 03/068305 A1 | 8/2003 |
| EP | 1764125 | A1 | 3/2007 | WO | WO 03/075980 A2 | 9/2003 |
| FR | 576 849 | | 8/1924 | WO | WO 03/095003 A1 | 11/2003 |
| FR | 576849 | | 8/1924 | WO | WO 2004/012796 A1 | 2/2004 |
| FR | 2 611 013 | | 8/1988 | WO | WO 2004/029457 A1 | 4/2004 |
| FR | 2725902 | | 10/1994 | WO | WO 2004/030726 A | 4/2004 |
| FR | 2 733 915 | | 11/1996 | WO | WO 2004/037325 A1 | 5/2004 |
| FR | 2733915 | A1 | 11/1996 | WO | WO 2004/054644 A1 | 7/2004 |
| FR | 2 752 164 | A1 | 2/1998 | WO | WO 2004/056412 A2 | 7/2004 |
| FR | 2 781 617 | A1 | 1/2000 | WO | WO 2004/064593 A2 | 8/2004 |
| FR | 2781617 | A1 | 1/2000 | WO | WO 2004/071308 A1 | 8/2004 |
| GB | 478803 | | 1/1938 | WO | WO 2004/087240 | 10/2004 |
| GB | 591730 | | 3/1946 | WO | WO 2004/098683 A1 | 11/2004 |
| GB | 906574 | | 9/1962 | WO | WO 2004/101016 A1 | 11/2004 |
| GB | 1 268 575 | | 3/1972 | WO | WO 2004/101071 A2 | 11/2004 |
| GB | 1 403 034 | | 8/1975 | WO | WO 2004/110527 A1 | 12/2004 |
| GB | 2 088 215 | A | 6/1982 | WO | WO 2005/002649 A1 | 1/2005 |
| GB | 2 224 808 | A | 5/1990 | WO | WO 2005/004973 | 1/2005 |
| GB | 2 230 702 | A | 10/1990 | WO | WO 2005/018703 A2 | 3/2005 |
| GB | 2 270 552 | A | 3/1994 | WO | WO 2005/037184 A2 | 4/2005 |
| JP | 10179734 | A | 8/1991 | WO | WO 2005/037350 A2 | 4/2005 |
| JP | 5326062 | A | 12/1993 | WO | WO 2005/039673 A2 | 5/2005 |
| JP | 05326062 | A | 12/1993 | WO | WO 2005/046780 A1 | 5/2005 |
| JP | 7051251 | | 11/1995 | WO | WO 2005/065748 A1 | 7/2005 |
| JP | 8187286 | A | 7/1996 | WO | WO 2005/068006 A1 | 7/2005 |
| JP | 9217584 | A | 9/1997 | WO | WO 2005/072795 A2 | 8/2005 |
| JP | A-03-191965 | A | 7/1998 | WO | WO 2005/092410 A1 | 10/2005 |
| JP | 2000-59877 | A | 2/2000 | WO | WO 2005/094920 A1 | 10/2005 |
| JP | 3140740 | | 2/2000 | WO | WO 2005/118055 | 12/2005 |
| JP | 2000059877 | A | 2/2000 | WO | WO 2006/003130 A1 | 1/2006 |
| JP | 3140740 | B2 | 3/2001 | WO | WO 2006/015507 A2 | 2/2006 |
| JP | 2002-028246 | | 1/2002 | WO | WO 2006/015600 A2 | 2/2006 |
| NL | 1017427 | C | 11/2002 | WO | WO 2006/024650 A2 | 3/2006 |
| WO | WO 81/01795 | A1 | 7/1981 | WO | WO 2006/032689 A1 | 3/2006 |
| WO | WO 82/03558 | A1 | 10/1982 | WO | WO 2006/032692 A1 | 3/2006 |
| WO | WO 87/06474 | | 11/1987 | WO | WO 2006/061027 A2 | 6/2006 |
| WO | WO 92/04062 | A1 | 3/1992 | WO | WO 2006/061354 A1 | 6/2006 |
| WO | WO 93/03787 | | 3/1993 | WO | WO 2006/062912 A1 | 6/2006 |
| WO | WO 93/05840 | | 4/1993 | WO | WO 2006/075016 A1 | 7/2006 |
| WO | WO 93/11709 | A1 | 6/1993 | WO | WO 2006/077262 A1 | 7/2006 |
| WO | WO 94/20160 | | 9/1994 | WO | WO 2006/077263 A1 | 7/2006 |
| WO | WO 95/28327 | A | 10/1995 | WO | WO 2006/089958 A1 | 8/2006 |
| WO | WO 96/32981 | A1 | 7/1996 | WO | WO 2006/097111 A2 | 9/2006 |
| WO | WO 96/20021 | A1 | 10/1996 | WO | WO 2006/108775 A2 | 10/2006 |
| WO | WO 96/35472 | A1 | 11/1996 | WO | WO 2006/120253 A2 | 11/2006 |
| WO | WO 98/09065 | | 3/1998 | WO | WO 2006/121921 A2 | 11/2006 |
| WO | WO 98/26835 | A1 | 6/1998 | WO | WO 2006/122048 A1 | 11/2006 |
| WO | WO 98/33549 | A1 | 8/1998 | WO | WO 2007/000162 A1 | 1/2007 |
| WO | WO 98/58693 | | 12/1998 | WO | WO 2007/002523 A2 | 1/2007 |
| WO | WO 99/07435 | | 2/1999 | WO | WO 2007/020090 A1 | 2/2007 |
| WO | WO 99/33504 | | 7/1999 | WO | WO 2007/065944 A1 | 6/2007 |
| WO | WO 99/36009 | | 7/1999 | WO | WO 2007/071255 A1 | 6/2007 |
| WO | WO 99/56802 | | 11/1999 | WO | WO 2007/071258 A1 | 6/2007 |
| WO | WO 99/61815 | | 12/1999 | WO | WO 2007/093051 A1 | 8/2007 |
| WO | WO 00/02614 | | 1/2000 | WO | WO 2007/093182 A2 | 8/2007 |
| WO | WO 00/03757 | | 1/2000 | WO | WO 2007/122207 A1 | 11/2007 |
| WO | WO 00/44324 | A1 | 8/2000 | WO | WO 2007/140631 A1 | 12/2007 |
| WO | WO 01/04507 | A1 | 1/2001 | WO | WO 2007/140783 A2 | 12/2007 |
| WO | WO 01/30419 | A2 | 5/2001 | WO | WO 2007/140785 A1 | 12/2007 |
| WO | WO 01/68180 | | 9/2001 | WO | WO 2007/141210 A1 | 12/2007 |

| | | |
|---|---|---|
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/034830 A1 | 4/2010 |

* cited by examiner

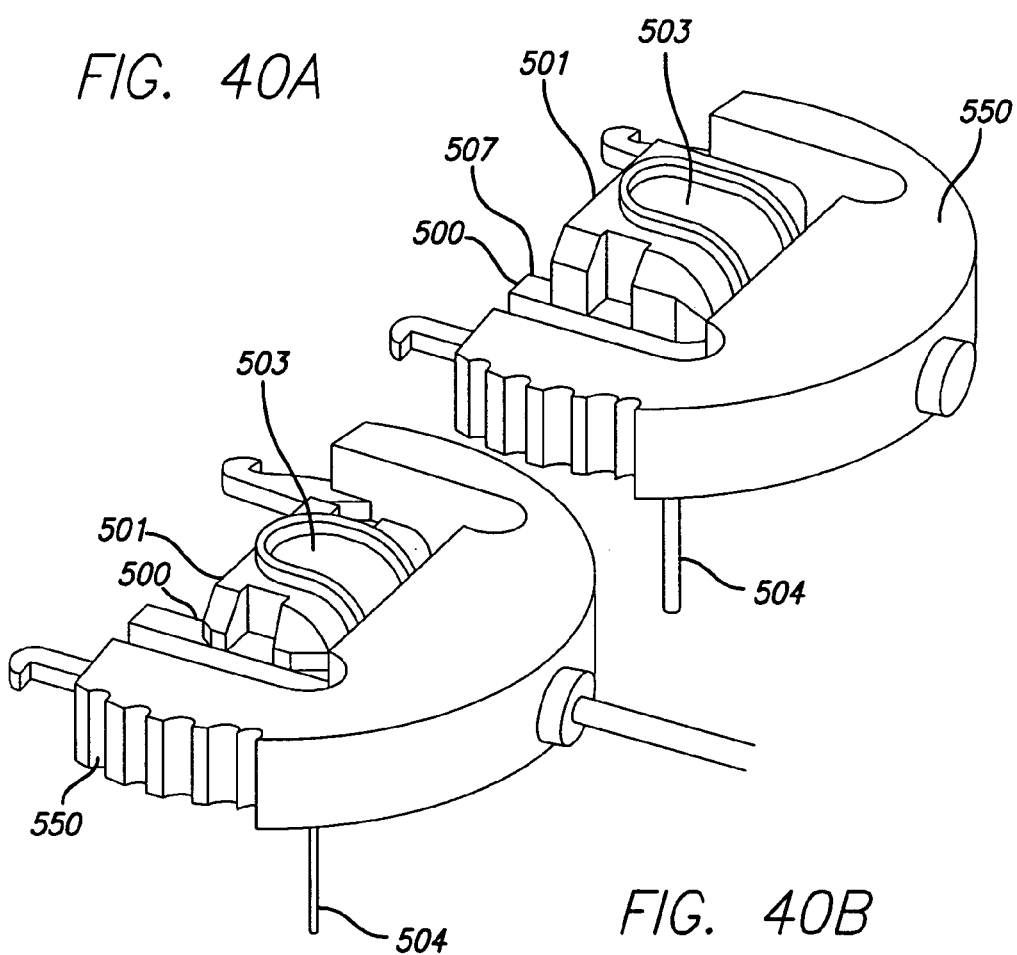

CANNULA DEVICE

This application claims the benefit of U.S. Provisional Application No. 60/600,209, filed Aug. 10, 2004.

FIELD OF THE INVENTION

The present invention relates to a cannula device, especially for use in infusion sets. The cannula device may be used in conjunction with various versions of infusion sets.

BACKGROUND

Normally, an infusion set for intermittent or continuous administration of a therapeutic substance, such as insulin, is in the form of a two-part device.

A traditional infusion set comprises a base part having a cannula for insertion into a patient where the base part has means for receiving a connector cannula extending from a connector and for bringing the connector cannula into fluid communication with the cannula of the base part. Often, the connector needle is in fluid communication with a drug delivery device, such as an insulin pump.

Different kinds of infusion sets are described in WO 02/068014 A2, EP 0 956 879 A1, U.S. Pat. No. 5,522,803, U.S. 2003/0225373 A1 and WO 03/026728 A1.

U.S. 2003/0176852A1 discloses an infusion set in which a base part comprises a pivoting member, the base part comprising a cannula for insertion into a patient and pivoting member has an inner cavity with one receiving end adapted to receive an inserter needle or a piercing member and two connecting ends (316I and 320) for further connection with the cannula of the base part. During insertion, the pivoting member is positioned orthogonally to the base part and an inserter needle penetrates a membrane in the receiving end. The needle passes through a canal and through the first connecting end into the cannula which then can be inserted. After insertion, the needle is removed and the pivoting member is connected with a connector. The connector and the pivoting member are connected from the same direction as the connection between the pivoting member and the inserter. The pivoting member is then turned in order for the second connecting end to align with the cannula. This device has the drawback that it is very sensitive to movement of the pivoting member since a small turning will close off the delivery of drugs.

WO 02/094352 A2 discloses an infusion set having a base part that can receive an insertion needle from one direction and a connector needle from a second direction. This design does not allow the patient to choose the direction he/she wants to connect the connector with the base part.

In the infusion sets described above, the construction of the cannula and the means for providing fluid communication between the cannula and the cannula from the connector are unique for each set. Normally each infusion set also utilizes a specific set of guiding and/or locking members and thus allows only for a specific connector to engage with the base part.

It would be highly desirable from both a production point of view and practical use if a universal part having a cannula and means adapted to receive the cannula from the connector and fitting to most/all common infusion sets available. Aspects of the present invention are intended to cover both infusion sets as described above and variants thereof when such a universal part is used therein.

Furthermore, in the infusion sets described above, both the connector and the base part have to be substituted if the patient wishes to change to a different base part. It would be advantageous if different types of connectors could be used with the same base part and different types of base parts could be used with the same connector. It would also be advantageous if connection from different angles would be possible.

BRIEF SUMMARY

An object of the present invention is therefore to provide a cannula device which can be used as a component in most if not all common infusion sets and which allows for connection from more than one direction.

According to one aspect of the present invention, a cannula device for infusion sets is provided. The cannula device includes a housing and at least one membrane mounted to the housing and adapted for receiving a piercing member of a connector. A cannula is mounted to the housing. The cannula device is adapted to removably attach to a base part of an infusion set. The cannula device can receive the piercing member from a first receiving direction and from a second receiving direction different from the first direction, providing fluid communication between the piercing member and the cannula.

According to another aspect of the present invention, a cannula device for mounting to a base part of an infusion set is provided. The cannula device includes a housing and at least one membrane adapted to receive a piercing member of a connector and a cannula mounted to the housing. The cannula device is adapted to removably attach to a base part of an infusion set. The cannula device can receive the piercing member from a first receiving direction and from a second receiving direction being different from the first direction providing fluid communication between the piercing member and the cannula.

According to another aspect of the present invention, an infusion set is provided. The infusion set includes a base part and a cannula device removably connected to the base part. The cannula device includes a housing having at least one membrane secured thereto, and a cannula mounted to the housing. The cannula device is adapted to receive a piercing member of a connector from a first receiving direction and from a second receiving direction different from the first direction, providing fluid communication between the piercing member and the cannula of the cannula device.

An advantage of the cannula device of the present invention is that it can be used as a key component in infusion sets with both parallel and orthogonal connection between the connector and the base part seen relative to the skin of the carrier. Thus this key component can be mass produced and be used as a component in a series of desired designs of the infusion sets. This results in lower manufacturing costs, a more flexible production line and a more flexible product.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

The cannula device will be described in further detail with reference to the figures.

FIGS. 40A and B are perspective views showing the cannula device mounted in the connector at different positions;

DETAILED DESCRIPTION OF THE INVENTION

Figure 1:
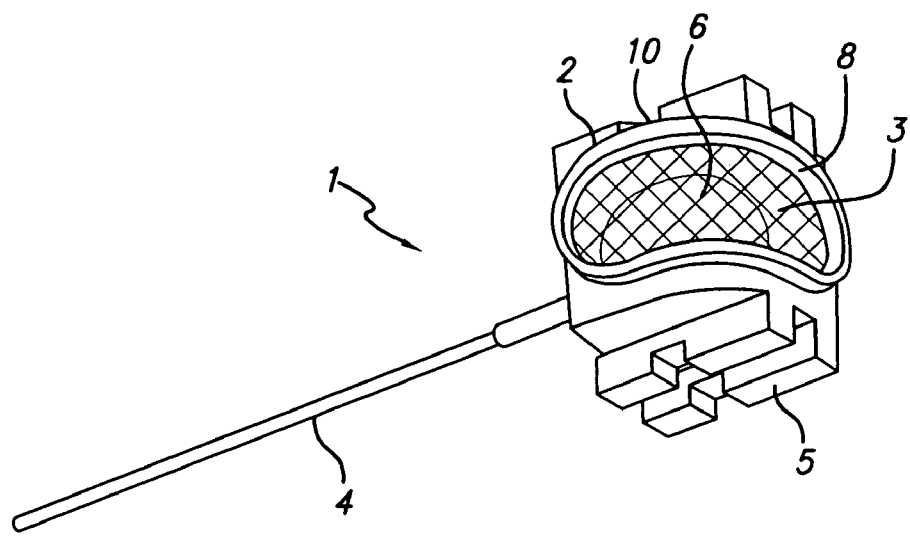
FIG. 1 is a perspective view of an embodiment of the cannula device of the present invention.

FIG. 1 shows a first embodiment of the present invention. In this embodiment, the cannula device 1 includes a housing 2 and a membrane 3 which together define a cavity 6 being adapted to receive a piercing member extending from a connector. A cannula 4 is mounted in the housing 2 and is in fluid communication with the cavity 6. The membrane 3 may have an oval or elongated shape covering at least a portion of two sides 8, 10 of the cannula device 1. Alternatively, the membrane 3 may cover at least a portion of one or more sides other than the two sides 8, 10. The membrane 3 may also be configured in an alternative shape, for example, but not limited to, circular, rectangular, triangular and others. This allows for connection with a connector from more than one angle. The membrane 3 is shown as a single membrane that curves around the cavity 6. Alternatively, more than one membrane may be provided for entry of a piercing member in different receiving directions as described below.

Figure 2:
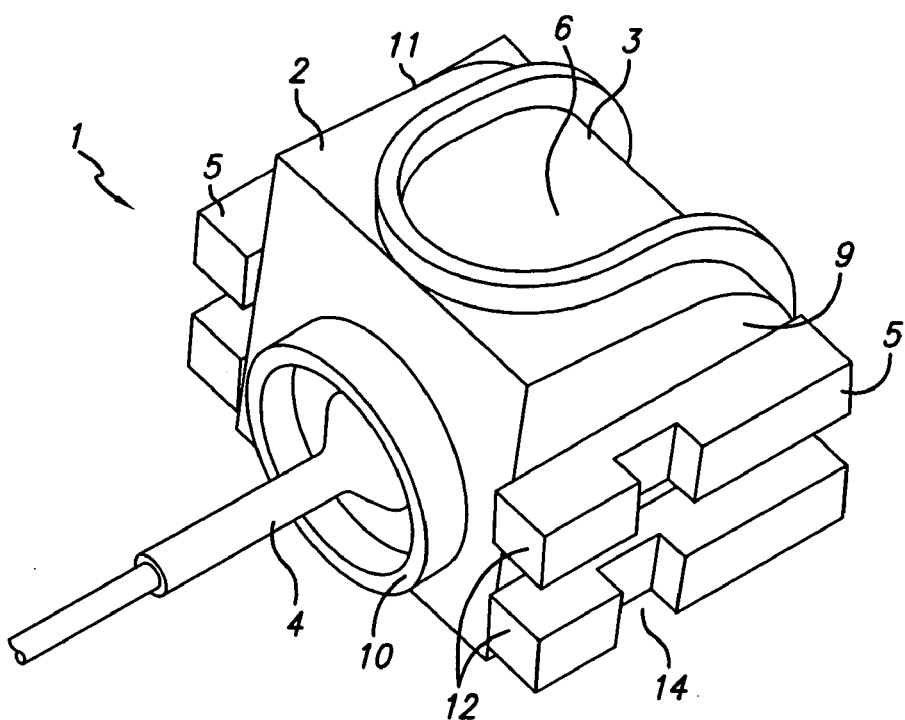
FIG. 2 is an enlarged view of the housing of the cannula device shown in FIG. 1.

In the embodiment shown in FIG. 1, guiding members 5 are provided on the housing 2, thus guiding the connection with a device such as the connector, the inserter, or both. This helps ensure that the cannula from the connector, the connector needles, or both, properly align as described below. As shown in FIGS. 1 and 2, and described below, the guiding members 5 may guide connection from at least two angles being essentially orthogonal to each other.

FIG. 2 shows the cavity 6 defined by the housing 2 and the membrane 3. The cavity 6 may be in fluid communication with the cannula 4. As shown, a pair of guiding members 5 extends from the housing 2, opposite each other on sides 9, 11 of the housing 2. Each guiding member 5 may include a pair of elongate rail members 12 adapted to slidably engage with a device such as a connector or an inserter as described below. Each rail member 12 may further include a notch 14 defined in the rail member 12 for removably engaging another or the same device. Additional guiding members 5 are possible for removable engagement with the device such as the connector, for example from an infusion set, or an inserter, as will be apparent to one of skill in the art.

Figure 3:
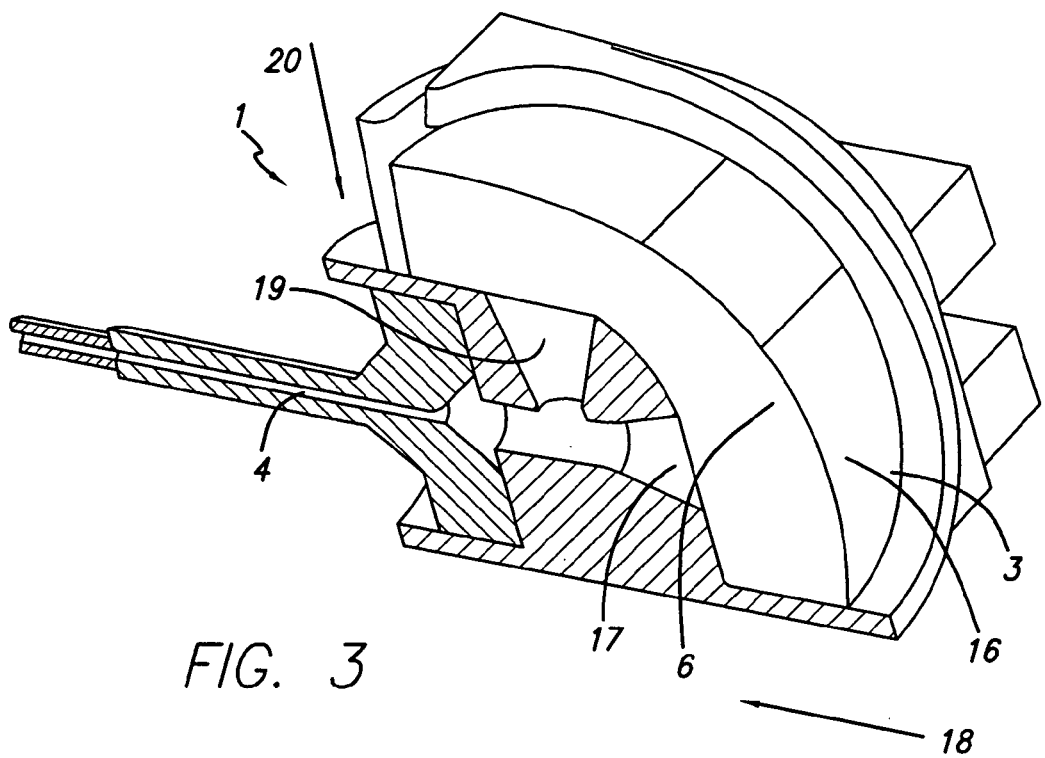
FIG. 3 is a sectional view of the cannula device shown in FIG. 2.

A sectional view of the cannula device 1 shown in FIG. 3 shows the cavity 6 in further detail. The cavity 6 defines a chamber 16 which is in fluid communication with the cannula 4. An piercing member (such the piercing member 580, 680 described below) can penetrate the membrane 3 at any position on the membrane 3 and communicate with the chamber 16. Thus, the piercing member such as a piercing member may be in fluid communication with the cannula 4 of the device 1, and making it possible to connect the connector to the cannula device 1 from different angles. As shown in FIG. 3, the cannula device 1 may further include entry channels 17 and 19 of the cannula 4. Entry channels 17 and 19 may be in fluid communication with the chamber 16 for reception of a therapeutic substance through the piercing member. Alternatively, the entry channels 17 and 19 may directly receive the piercing member for delivery of the therapeutic substance as described below.

Figure 4:
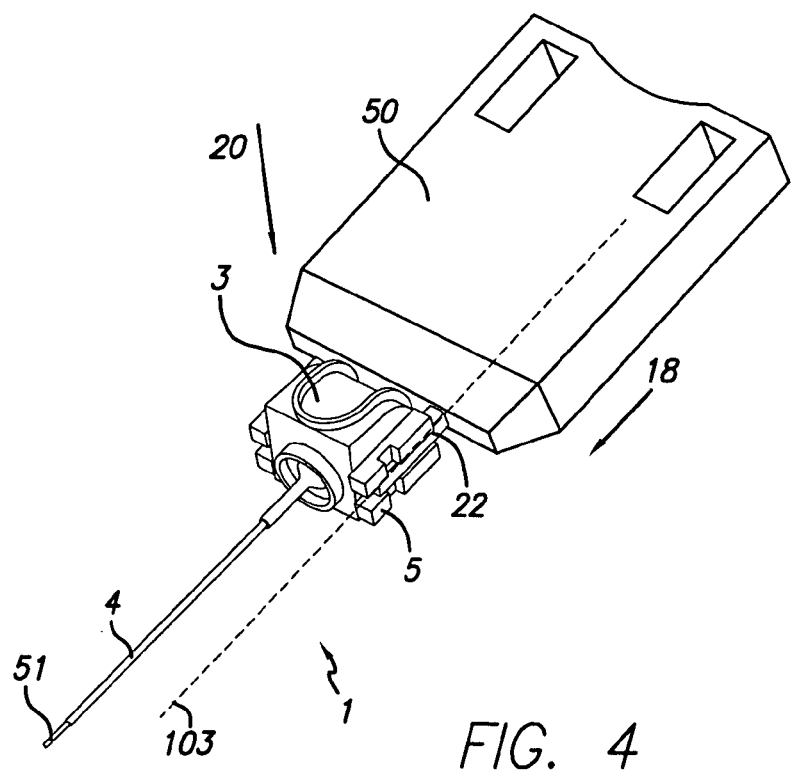
FIG. 4 is a perspective view of the cannula device coupled with an inserter.

As shown in FIG. 4, the cannula device 1 is connected to an inserter 50. A needle 51 extends from the inserter 50, penetrating the membrane 3 at a first position and extending out through the cannula 4. The inserter 50 is used to place the cannula 4 of the device 1 subcutaneously in the patient. After insertion, the inserter 50 is removed and the cannula 4 is left in the patient for delivery of a therapeutic substance and later withdrawal, for example, when a base part (shown in FIG. 5), the cannula device 1, or both, are removed. FIG. 4 shows that the inserter 50 can be connected to the cannula device 1 from a first insertion direction 18 that may be generally parallel to or aligned with the axis 103 of the cannula 4. A portion of the membrane 3 remains accessible and thus illustrates that it is possible to connect to a connector from a second direction 20 which is different from the first direction 18. As shown, there is approximately a 90° angle between the two directions 18, 20. The first direction 18 and the second direction 20 may be predetermined by the location of the entry chambers 17 and 19 for direct reception of the piercing member. Alternatively, any reception direction may be used with the chamber 16 that allows fluid communication between the piercing member and the cannula 4 of the cannula device for delivery of the therapeutic substance. By way of example, additional angles between the first direction 18 and the second direction 20 are possible. Preferably, the angle between the first direction 18 and the second direction 20 is in the ranges from about 5o to about 175o, more preferably from about 30o to about 150o. Preferably, the angle between the first direction 18 and the second direction 20 is at least about 45o, more preferably about 60o, 75o, 85o most preferably about 90o. One of skill in the art will understand that additional connection directions are possible and from many different angles.

Figure 5:
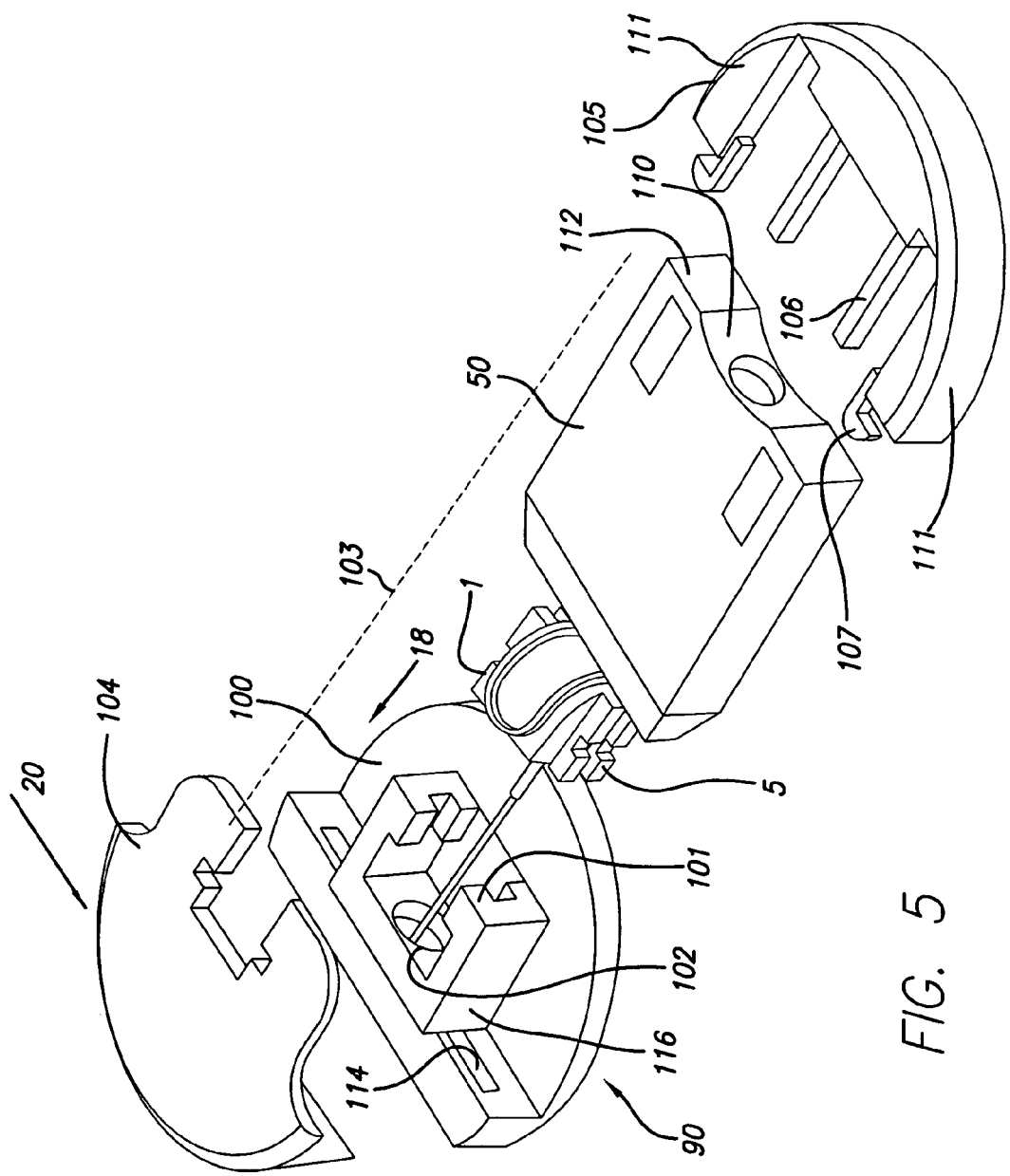
FIG. 5 is a perspective view of the cannula device mounted in a base part of an infusion set.

As shown in FIG. 5, the cannula device 1 assembles into a base part 100 of an infusion set 90. In this embodiment, the base part 100 includes base guiding members 101 which fit together with the guiding members 5 mounted on the housing 2 of the cannula device 1. The guiding members 5 on the cannula device 1 may be used to guide and align the cannula device 1 into the base guiding members 101 of the base part 100 and to guide the connection to a connector. An opening 102 in a portion of the base guiding members 101 of the base part 100 allows for connection of the guiding members 5 of the cannula device 1 or a device, such as a connector or an inserter from a second and different direction 20 than the first direction 18 which is parallel to the axis 103 of the cannula 4. The guiding members 5 may be elongated rectangular rails, as shown in this embodiment, or pins, or other types of known alignment mechanisms.

Protecting members 104, 105 are also shown in FIG. 5. The protecting members 104, 105 secure and at least partially enclose, and cover the cannula device 1 on a plurality of sides. The protecting member 105 includes guiding arms 106 and locking arms 107 similar to guiding and locking arms that may be provided on a connector. Exemplary engagement of the locking arms of a connector with an infusion set is described in detail in U.S. Pat. No. 5,522,803 which is incorporated by reference herein in its entirety. The guiding arms 106 are adapted to slidably fit with mating openings 110 formed in the inserter 50 as shown in FIGS. 5 and 6.

Figure 6:
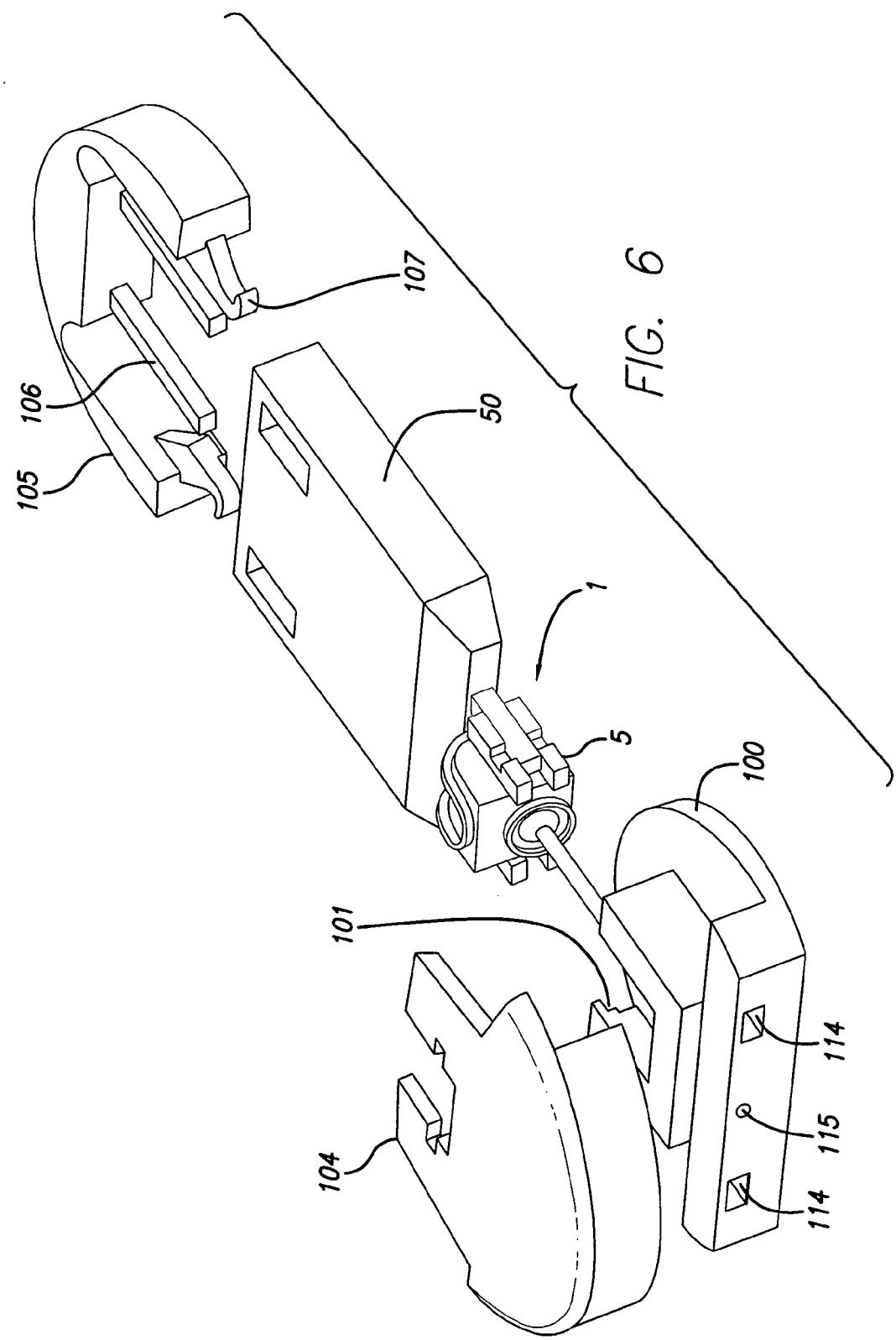
FIG. 6 is an exploded perspective view of the cannula device mounted in a base part.
Figure 8:
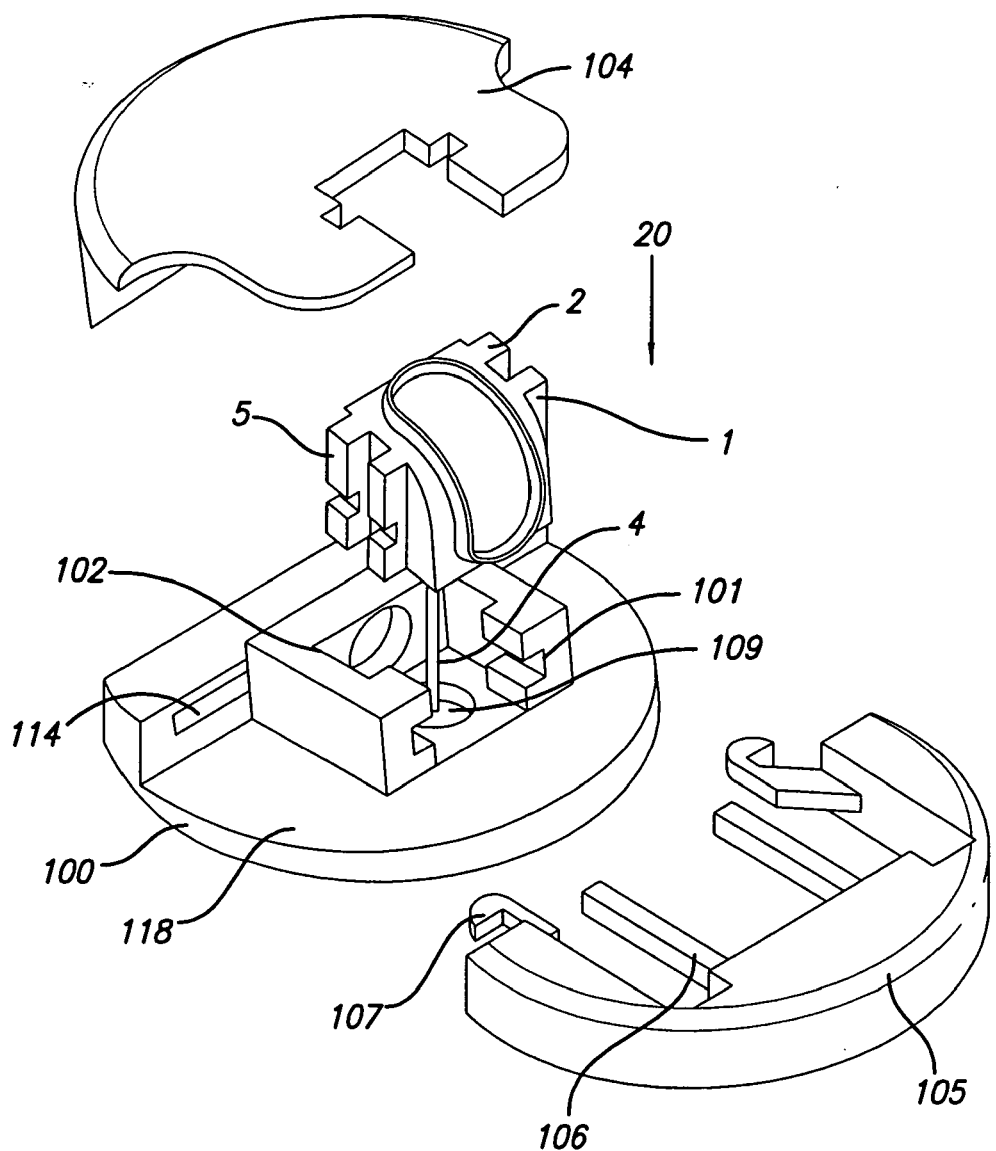
FIG. 8 is an exploded top perspective view showing the cannula device mounted in a base part in which a cannula is essentially orthogonal to the main plane of the base part.

FIG. 6 illustrates an alternative, perspective view of the embodiment shown in FIG. 5. Alternatively, the guiding arms 106 may slidably fit with the guiding members 101 of the base 100 as shown in FIG. 8 showing the inserter 50 removed. The locking arms 107 may releasably engage openings 114 formed in the base 100. The releasable engagement of the cannula device 1 with the base part 100 allows for exchange of the base part 100 and the cannula device 1. For example, but not limited to the following, the cannula device 1 may be removed from the base part 100 by sliding the cannula device 1 out of the base part 100. Another cannula device 1 may be slid into the same base part 100 using the same guiding arms 106 of the base part 100. An advantage of the present invention is that the same base part may be reused several times by the patient, thus saving medical expenses. Additionally, the exchangeable cannula device and the base part allow for the use of different cannula devices in the same base part, for example, but not limited to, having a different size cannula 4 with the cannula device 1, i.e., the length or the diameter of the cannula 4. This exchange allows the infusion sets to be configured in sets that are tailored for the patient using these modular components.

Figure 7:
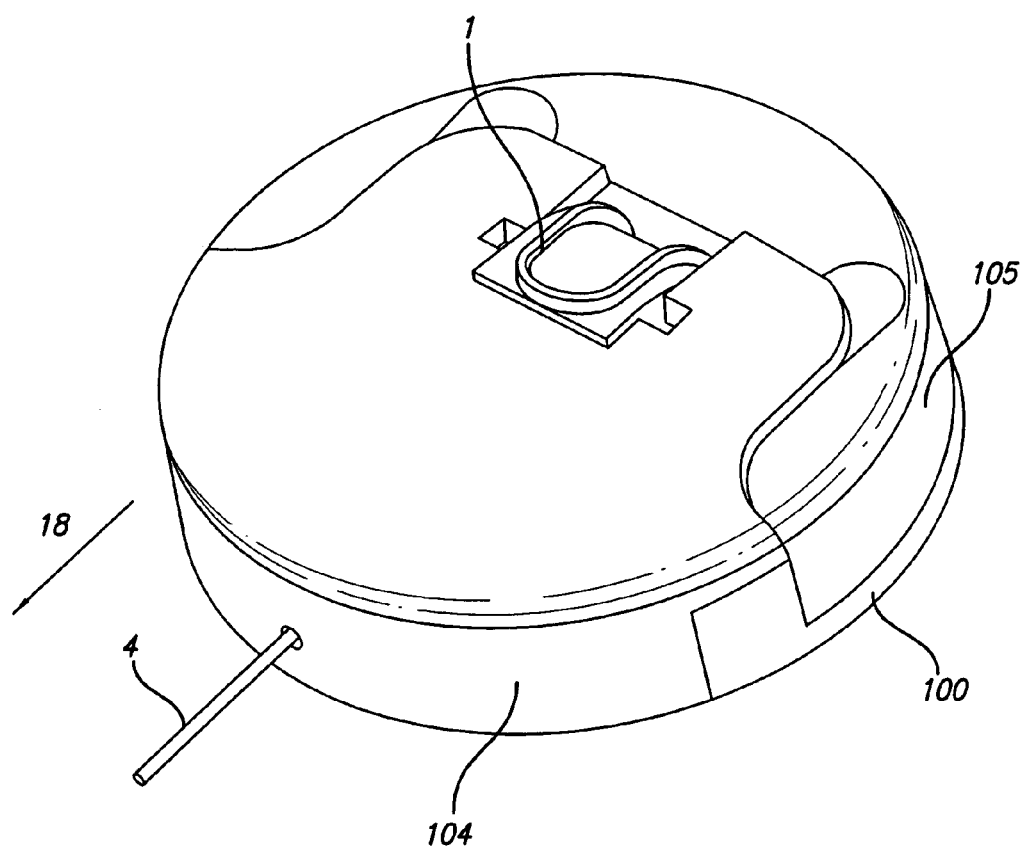
FIG. 7 is a top view of the cannula device mounted in a base part and encapsulated by protecting members.

FIG. 7 illustrates the cannula device 1 releasably mounted on the base part 100 and the cannula device 1 and the base 100 are capped by protecting members 104 and 105.

FIG. 8 shows the cannula device 1 mounted in the base part 100 in an alternative position to that shown in FIGS. 5-7. In particular, the cannula device 1 is mounted in the second direction 20 wherein the cannula 4 is mounted on the base part 100 essentially orthogonal to a main plane 118 of the base part 100. The base part 100 includes multiple guiding members 105 and openings 102 to allow removable attachment of the cannula device 1 in at least these multiple orientations. As shown in FIG. 8, the guiding members 5 of the housing 2 releasably fit with the opening 102 on the base part 100. Changing the orientation of the guiding members 5 of the housing 2 with respect to the guiding members 101 and the openings 102 on the base part 100 allows the angle between the cannula 4 and the base part 100 to be changed, which may be desired in certain circumstances. Protecting members 104, 105 may also be engaged with the base member 100 when the guiding members 5 of the housing 2 are slidably received in the openings 102 of the base part 100.

Figure 9:
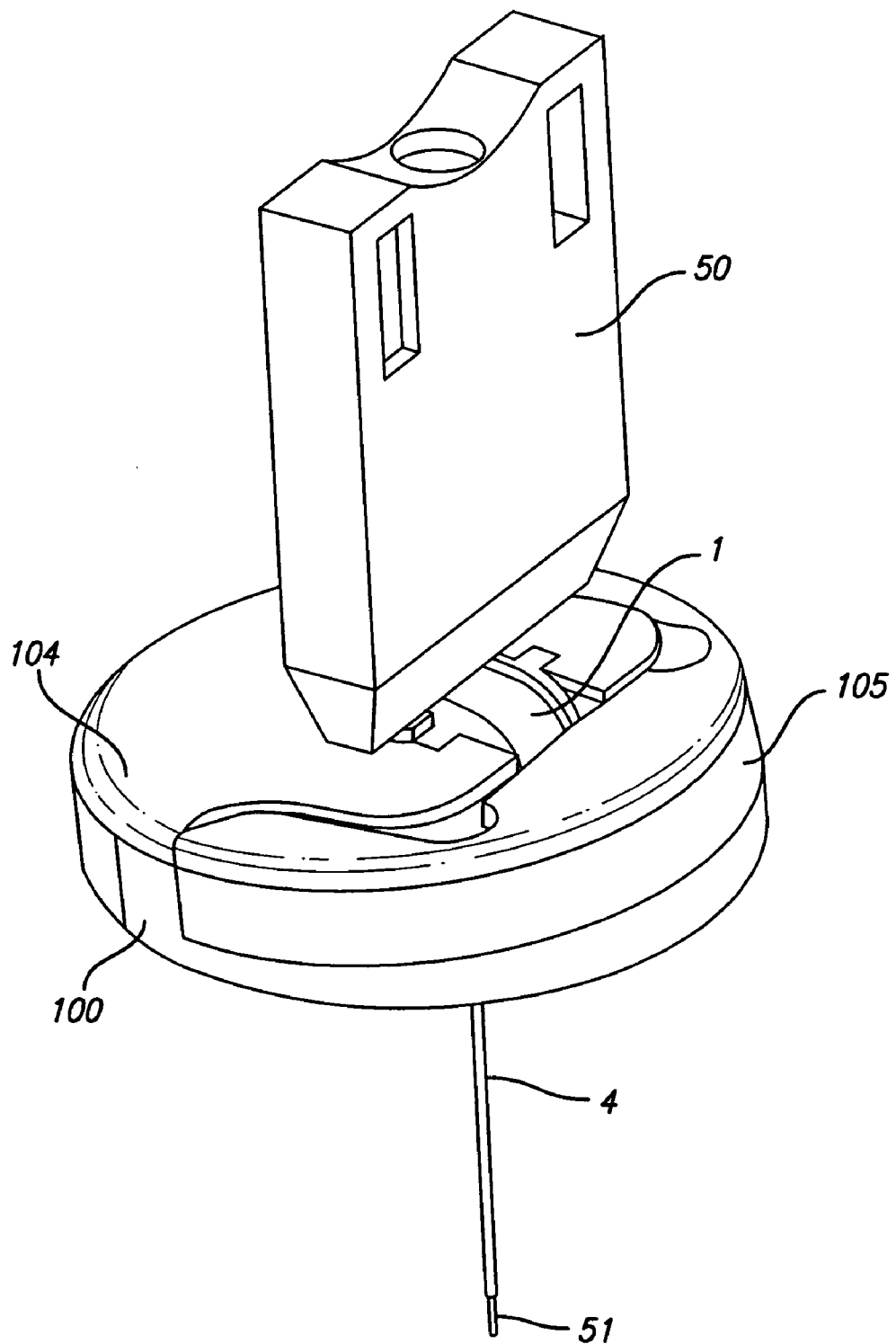
FIG. 9 is a side view of an inserter coupled with the embodiment shown in FIG. 8.

As shown in FIG. 9, in combination with FIG. 8, the inserter 50 including the needle 51 extending through the cannula 4 is connected to the cannula device 1 when the cannula device 1 is slidably received in the opening 102 in the base part 100. The protecting members 104, 105 are also engaged with the base part 100. Alternatively, a connector (for example, a connector 450, 550, 650, described below) may be engaged with the base part 100 in the position shown for the inserter 50 or in the position shown for the protecting member 105 and be connected to the cannula device 1. As shown in FIG. 9, the cannula device 1 and the inserter 50 are engaged with the base part 100 in an orthogonal direction as compared to the parallel direction shown in FIG. 7.

Figure 10:
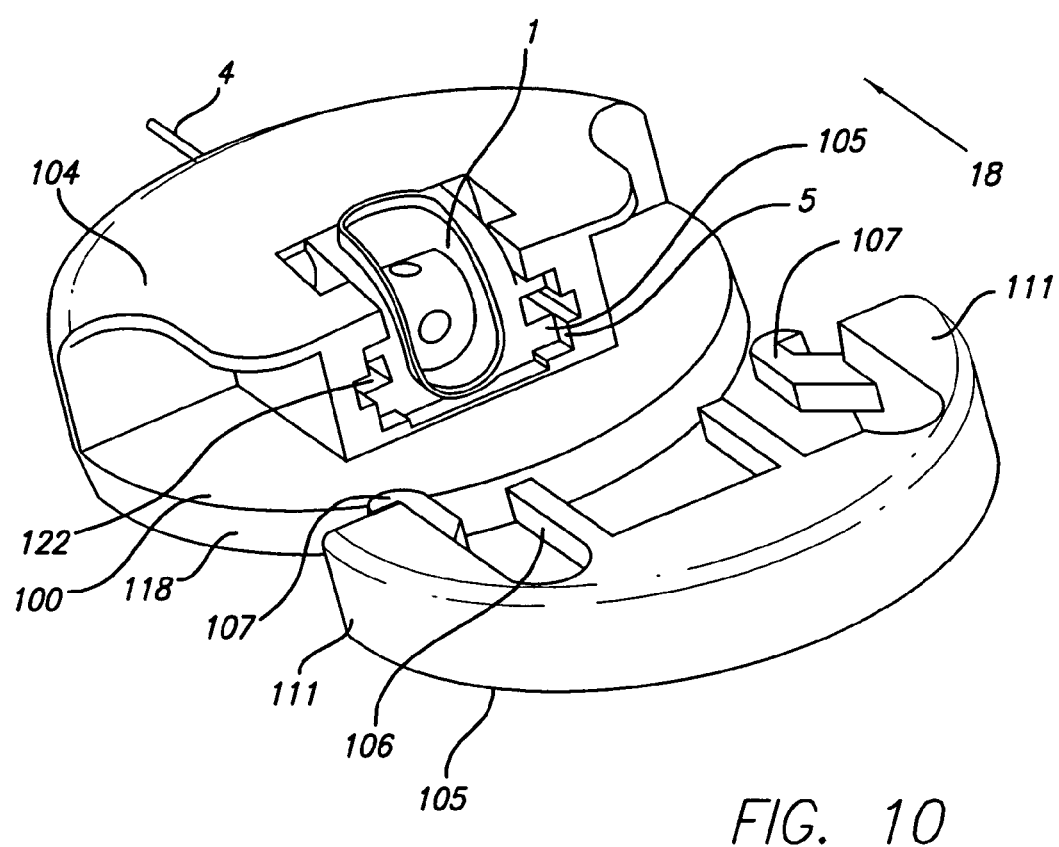
FIG. 10 is a perspective view showing the mounting of the cannula device in the base part.

In FIG. 10, the cannula device 1 is mounted in the base part 100 in the first direction 18 where the cannula 4 is substantially parallel with the main plane 118 of the base part 100. The cannula device 1 may be slidably retained in the base part 100 by the friction between the guiding members 5 of the cannula device 1 and the guiding members 101 of the base part 100. The guiding arms 106 of the protecting member 105 may be slidably engaged in an opening 122 formed in the base 100 when the cannula device 1 is engaged with the base 100. The cannula device 1 may also be engaged with the base part 100 using several methods known to one of skill in the art. For example, but not limited to, mechanical means, such as rims, grooves or taps; by adhesives such as glue or by friction such as the cannula device 1 fitting with the opening 102 in the base part 100 and being retained therein by the friction between the sides of the guiding means 5 of the cannula device 1 and the sides of the opening 102. The base part 100 may further include locking members that removably secure the cannula device 1 in the base part 100. In addition, the cannula device 1 may have locking members, such as the engaging notch 14, shown in FIG. 2, for securing the cannula device 1 in the base part 100. The locking members may further include disengagement members for releasing the locking members.

Figure 11:
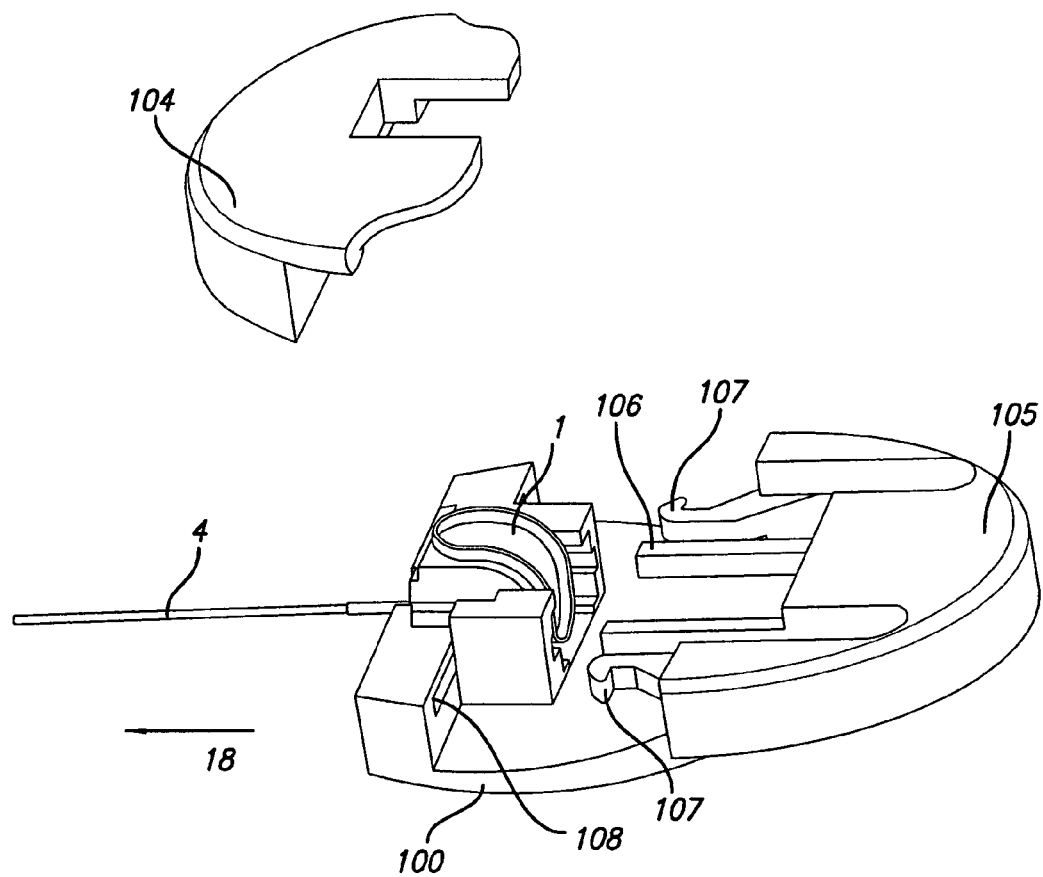
FIG. 11 is an exploded side view showing another position for the cannula device mounted in the base part.
Figure 12:
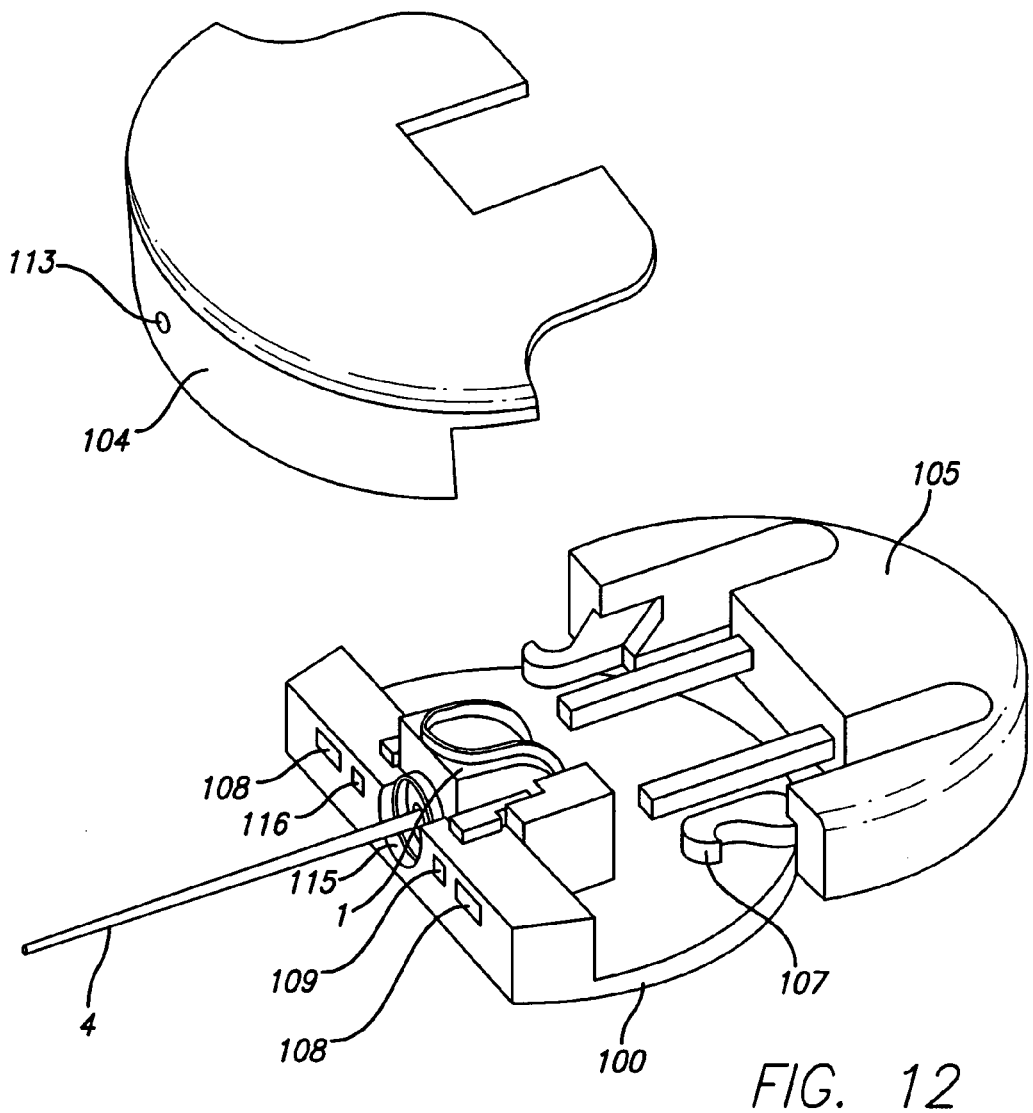
FIG. 12 is an exploded view showing the embodiment of FIG. 11 from a different angle.

FIGS. 11 and 12 show how the locking arms of the protecting member 105, or alternatively a connector having similar locking arms (as shown in FIGS. 52-57), can engage in openings 107 in the base part 100. The cannula 4 is shown extending in the parallel direction, similar to FIG. 7.

Preferably, the cannula device 1 of the present invention is made from the following materials, but is not limited to the materials described herein. One of skill in the art will recognize that other materials are possible and are within the scope of the present invention.

The housing 2 of the cannula device 1 of the present invention is preferably made from a plastic material, more preferably polypropylene. The membrane of the present invention is preferably made of silicone, more preferably self-sealing silicone. The membrane is preferably adapted to be penetrated by and seal around a piercing member to enable fluid communication with the cannula of the cannula device or with at least one cavity for each of the receiving directions.

The cannula 4 of the cannula device 1, as shown, preferably is a soft cannula. Preferably, the cannula 4 is made of a plastic material. Preferred plastic materials for the soft cannula 4 are also materials which are sufficiently flexible to, bend, when the patient moves and sufficiently rigid to avoid kinking and closing off the drug supply. Further, the material should be compatible with medical use i.e. minimal skin irritation, non-toxic, non-decomposable in the body, etc. Thermoplastic elastomers (TPE) are a type of materials which satisfy these requirements. Examples of such elastomers include, but are not limited to: polyester ethers, ECDEL, styrene based TPE, olefin based TPE, urethane based TPE, ester based TPE, amid based TPE, polyolefines and silicone rubbers. In a preferred embodiment, the material is selected from the group consisting of polypropylene, C-FLEX™, mixtures of C-FLEX™, and polypropylene, LUPOLEN™ 1840H, LUPOLEN™ 3020D, PELLETHANE™ 2363-75D, PELLETHANE™ 2363-55D, TECOTHANE™ and CARBOTHANE™.

An alternative embodiment of the present invention is shown in FIGS. 13-25 illustrating the same cannula device 1 mounted in a different type of base part 200. FIGS. 13-25 show how the cannula device of FIGS. 1-12 can be mounted in different types of infusion sets, illustrating an advantage of the cannula device of the present invention.

Figure 13:
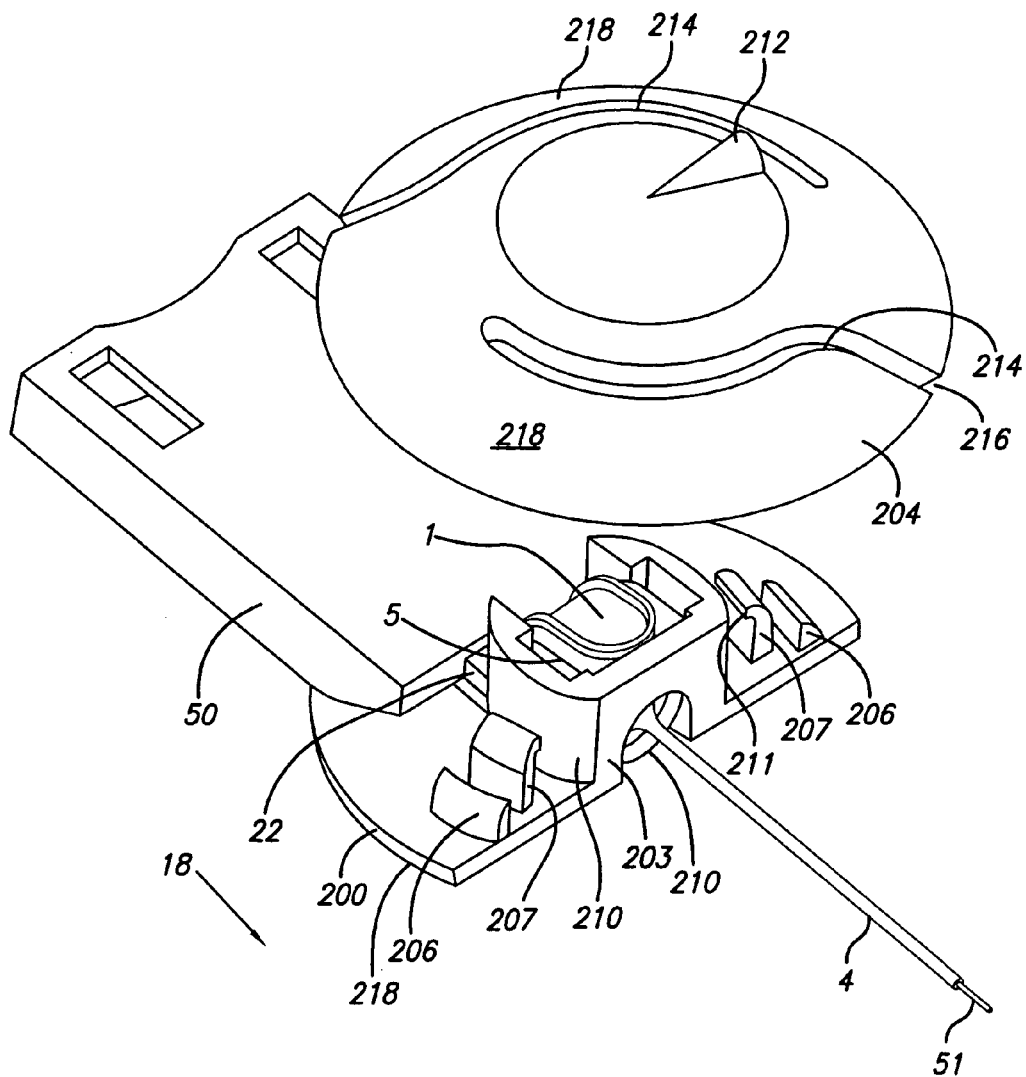
FIG. 13 is an exploded view of the cannula device mounted in a second type of base part including an inserter and a protective member.

As shown in FIG. 13, the cannula device 1 is engaged with the base part 200 in the first direction 18 where the cannula 4 is generally parallel to a main plane 218 of the base part 200. FIG. 13 also shows the inserter 50 with the needle 51 connected to the cannula device 1 and extending through the cannula 4. The projections 22 extend from the inserter 50 and slidably engage with the guiding members 5 of the cannula device 1.

In this embodiment, the base part 200 includes guiding members 201 which fit together with the guiding members 5 on the cannula device 1 as described above. The cannula 4 extends through an opening 203 in the base part 200, the opening 203 being sized to receive a annular ring 210 of the cannula device 1. The base part 200 further includes upstanding guiding members 206, 207 adapted for sliding reception of corresponding guiding members 208, 209 of a protecting member 204 once the inserter 50 is removed from the cannula device 1. The protecting member 204 may cover the cannula device 1 while the cannula 4 is secured in the skin of the patient and capable of delivering therapeutic substances to the patient through the cannula 4.

Figure 16:
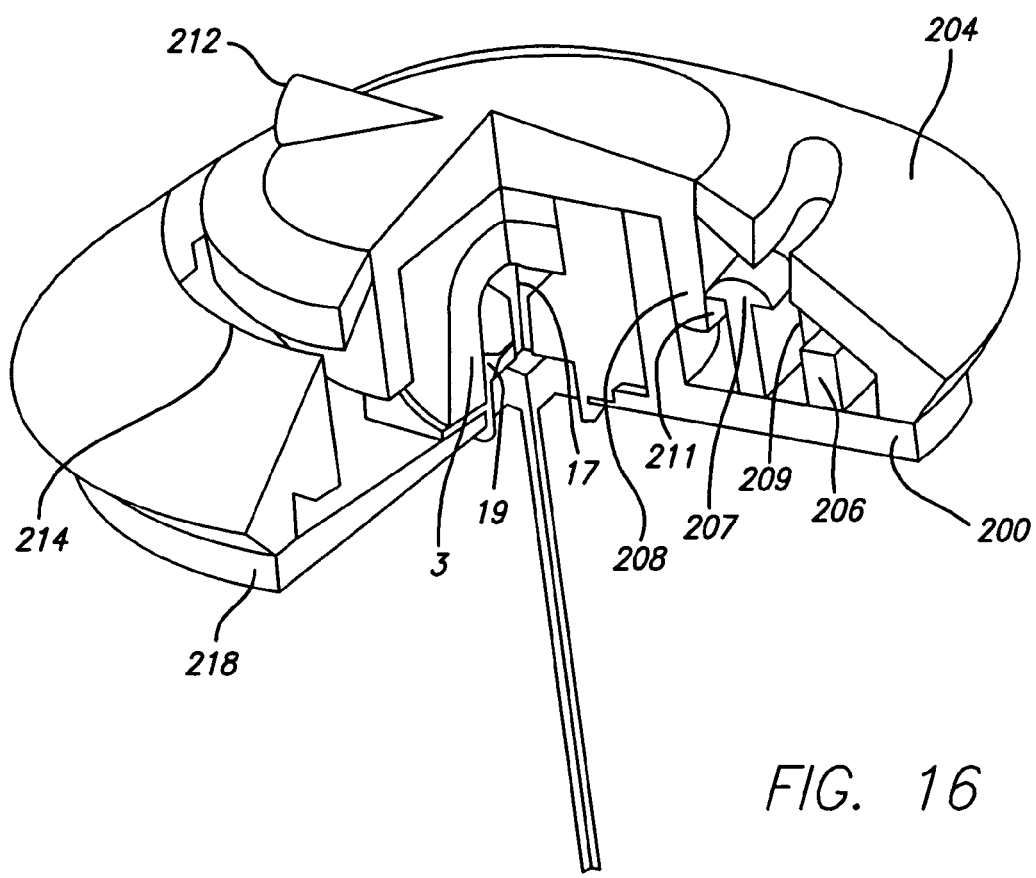
FIG. 16 is a sectional view of the embodiment shown in FIG. 15.

The guiding members 208, 209 can best be seen in FIG. 16 where the guiding members 206, 207 of the base 200 and the guiding members 208, 209 of the protecting member 204 are adapted to rotatably fit together to removably secure the protecting member 204 to the base part 200. Preferably, the guiding members 207, 208 may further include barbed projections 211 to facilitate the engagement. The guiding members 206, 209 may also include barbed projections 111. As shown in FIG. 13, the base part 200 preferably includes two upstanding guiding members 206, 207 on opposite sides of the base part 200. Alternatively, any number of guiding members 206, 207 or only guiding member 207 may be used to engage corresponding guiding members 208, 209 or guiding member 208 respectively, and the guiding members 206, 207 and 208, 209 may be of any size sufficient to removably secure the protecting member 204 to the base 200. other alignment, locking and/or guiding mechanism may be implemented.

Figure 15:
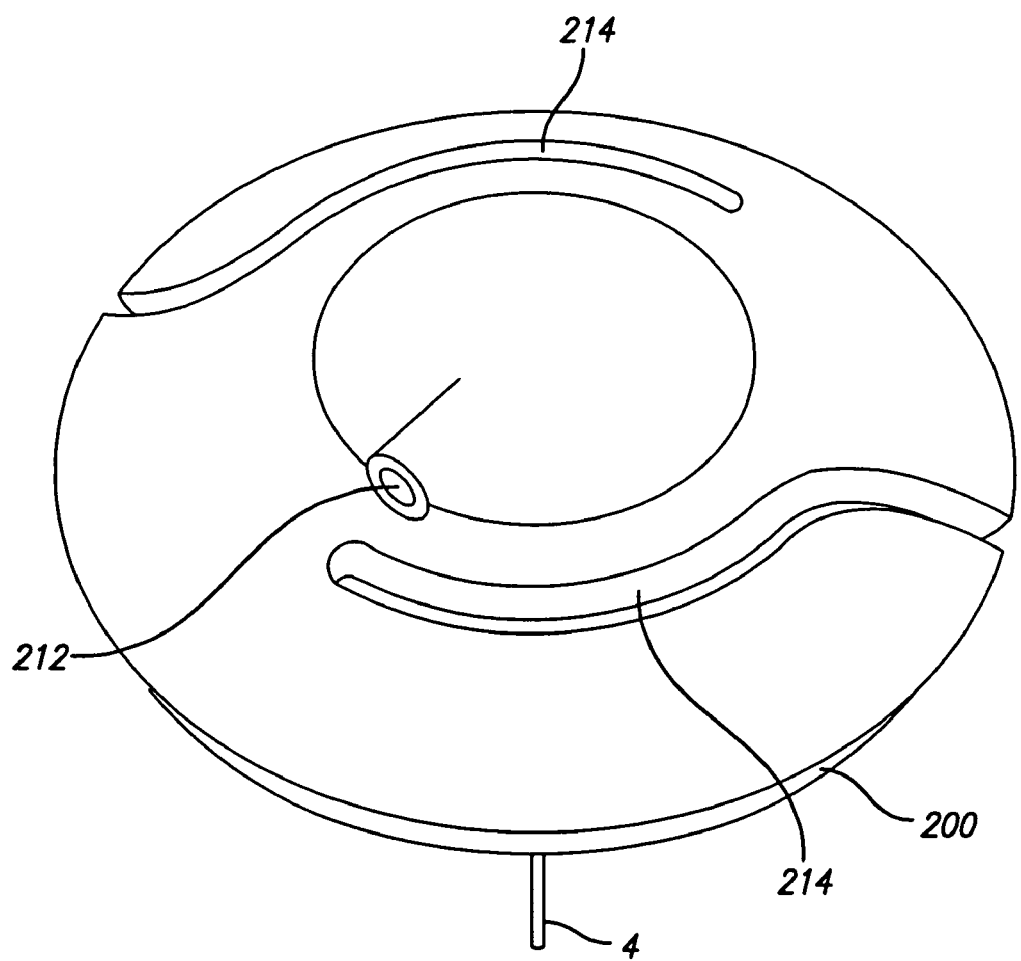
FIG. 15 is a top perspective view of the cannula device in the base part with a protective member.

The protecting member 204 may include an opening 212 as best can be seen in FIG. 15. Tubing (not shown) for delivering a therapeutic substance to the cannula device 201 may be inserted through the opening 212 so that the therapeutic substance may be delivered to the patient through the cannula 4 while the cover is in position on the base part 200. The protecting member 204 may further include elongate openings 214 on opposite sides of the protecting member 204. Preferably, the openings 214 extend from the periphery 216 of the member 204 inward and generally follow the contour of the periphery 216. Sides 218 of the protecting member adjacent the openings 214 provide partially flexible surfaces for gripping and turning the protecting member 204 to engage or release the base member 200. However, one of skill in the art will recognize that alternative engagement and release may be achieved by any mechanism commonly known to one of skill in the art.

Figure 14:
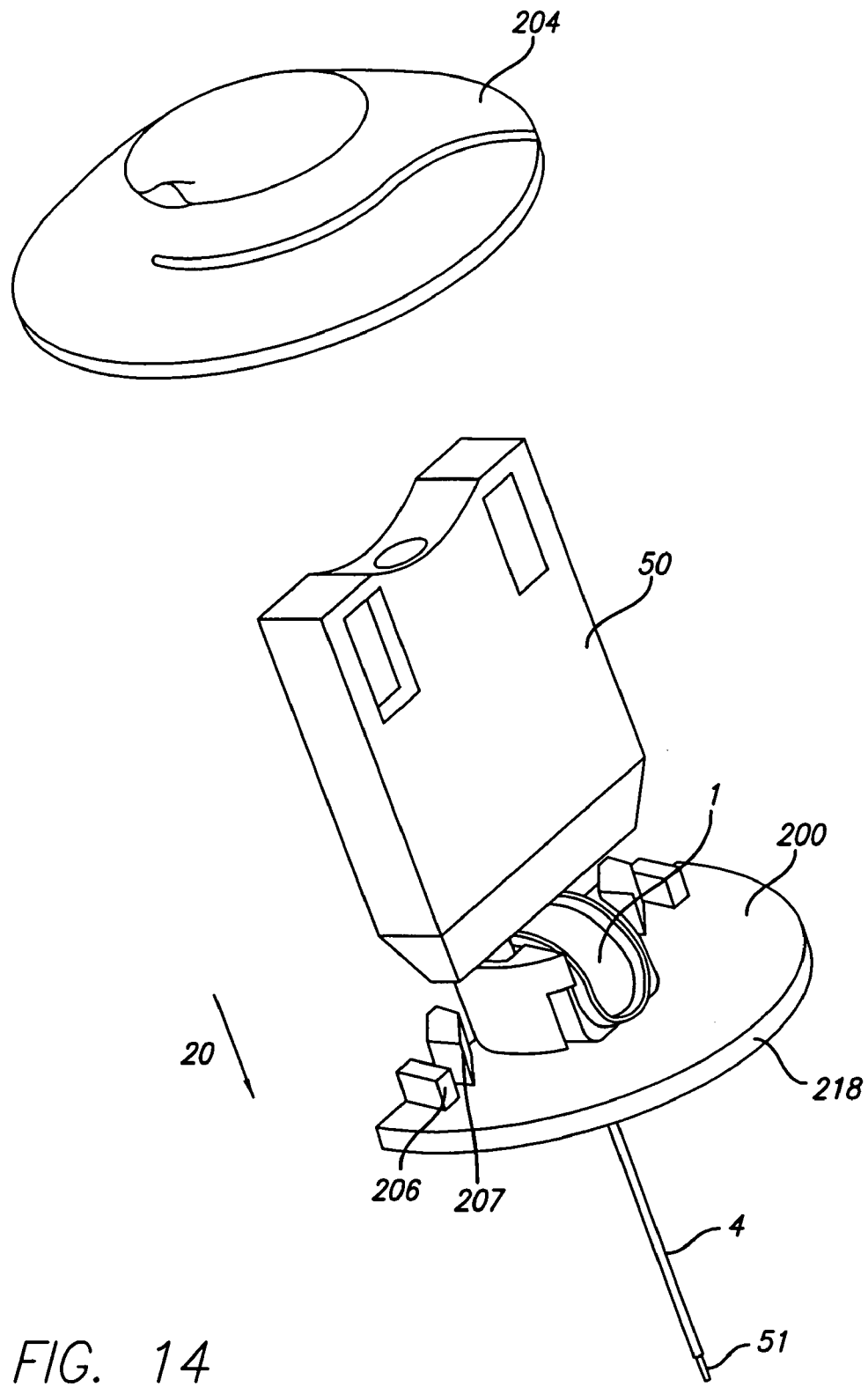
FIG. 14 is an exploded view of the cannula device mounted in the base part shown in FIG. 13 wherein the cannula device is mounted in an orthogonal direction.

FIG. 14 illustrates the cannula device 1 engaged with the base part 200 in the second direction 20 where the cannula 4 is generally perpendicular to the main plane 218 of the base part 200. FIG. 14 also shows the inserter 50 with the needle 51 connected to the cannula device 1 and extending through the cannula 4. The engagement of the inserter 50 and the protecting member 204 are as described above in FIG. 13. Once the inserter 50 is removed from the cannula device 1 and base part 200, the protecting member 204 may be engaged with the guiding members 206, 207 of the base part 200 as shown in FIG. 15. In some embodiments, protecting members may be engaged with the base part while an inserter is also engaged with the base part as described below. In the embodiment shown in FIG. 15, the cannula 4 extends from the bottom of the base 200. As discussed above, tubing may extend from the opening 212.

FIG. 16 illustrates a sectional view of the device shown in FIG. 15 where the protecting member 204 is engaged with the base part 200 and the cannula device 1 is positioned in the base part 200 with the cannula 4 projecting from the base part perpendicular to the main plane 218 of the base part 200. The protecting member 204 is sized and shaped to fit with the base part 200.

The guiding member 207 of the base part 200 and the guiding member 208 of the protecting member 204 having barbed projections 211 on the inner pair of guiding members 207, 208 are shown rotatably secured together. As discussed above and shown in FIG. 16, the outer pair of guiding members 207, 208 do not include barbed projections 211, however one of skill in the art will recognize that each of the guiding members 207, 208 may include guiding projections 211. The entry channels 17 and 19 of the cannula device 1 are below the membrane 3 that is protected by the protecting member 204.

Figure 17:
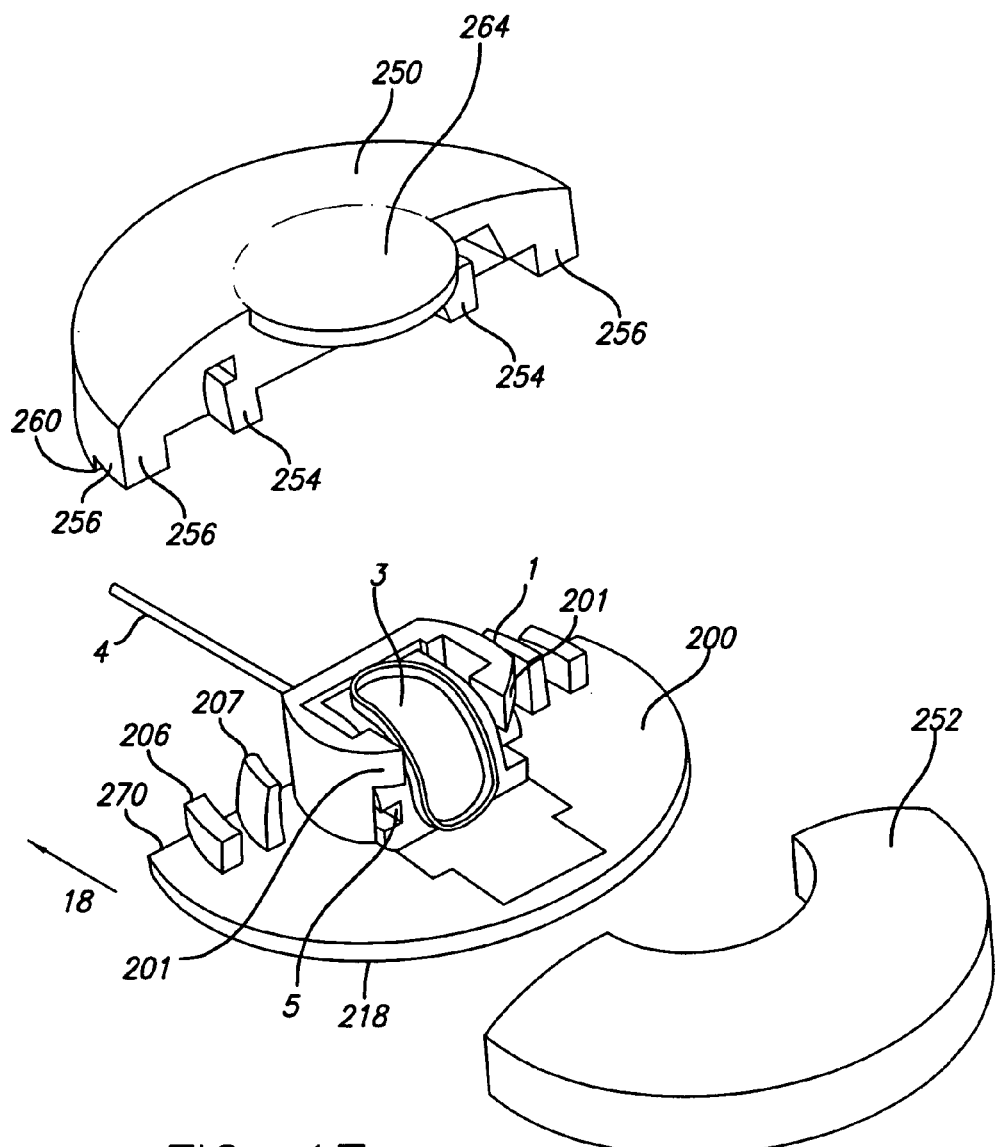
FIG. 17 is an exploded view of the embodiment shown in FIG. 14 having a different protective member.

FIG. 17 illustrates the same cannula device 1 engaged with the same base part 200 via the guiding members 5 of the cannula device 1 inserted into the base guiding members 201 where the cannula 4 extends in the first direction 18 generally parallel to the main plane 218 of the base part 200. FIG. 17 illustrates a pair of protecting members 250, 252 that may be engaged with the base part 200 to cover the cannula device 1 and the base part 200. The protecting members 250, 252 are sized and shaped to fit together with the base part 200 to cover the base part 200. As discussed above, alternative shapes for the base part 200 and the protecting members 250, 252 are possible. Other structures for mating these multiple members together may also be utilized.

The protecting member 250 includes a pair of guiding members 254 that may be adapted to engage the guiding members 207 of the base part 200. As described above, the base part 200 may include guiding members 206. The guiding members 206 may slide together with protrusions 256 on the periphery 258 of the protecting member 250. The protecting member 250 may further include a notch 260 for engaging an edge 270 of the base part 200. The protecting member 250 covers a portion of the membrane 3 of the cannula device 1 and may also engage the protecting member 252 to cover the base part 200 when the base part 200 is adhered to the skin of the patient and the cannula 4 is positioned transcutaneously for delivery of the therapeutic substance. As shown in FIG. 17, the protecting member may include a portion 264 for covering the membrane 3 of the cannula device 1 and the portion 264 may be made from a material that is different from the remainder of the protecting member and penetrable by a needle, such as the needle 51 of the inserter 50. For example, the portion 264 may be integrally molded to the member 250 and be formed from an elastomer. The protecting member 252 may be slidably engaged with the protecting member 250.

Figure 18:
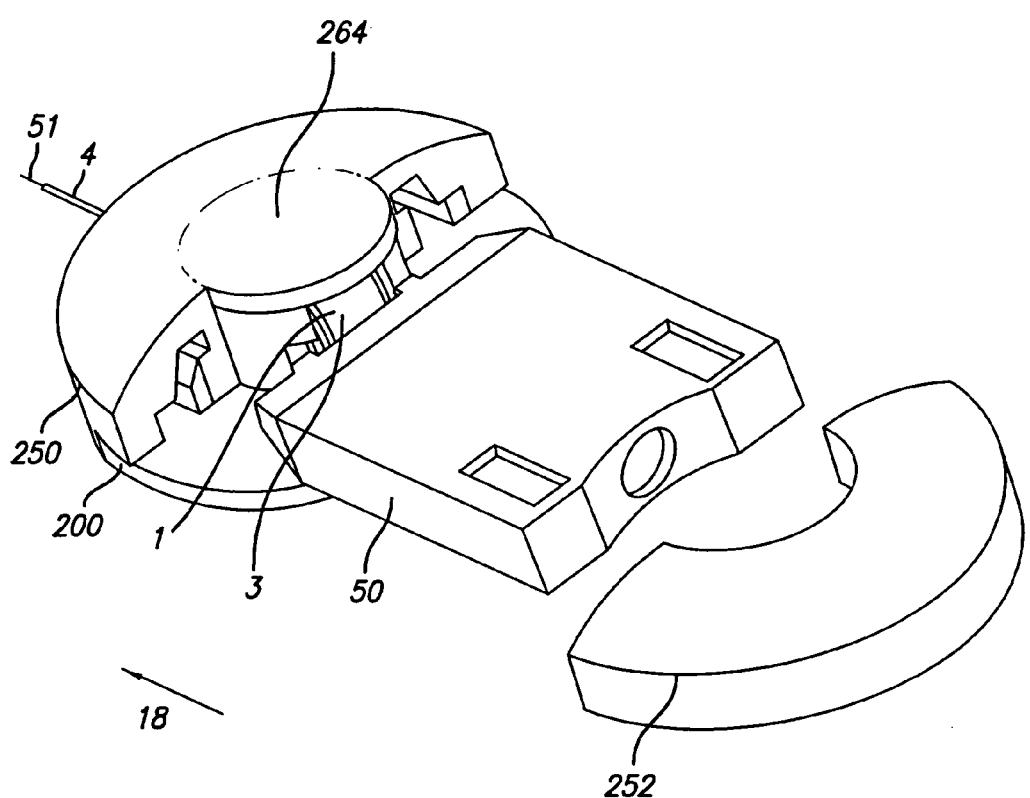
FIG. 18 is a perspective view of an embodiment of the cannula device, the base part and an inserter.

FIG. 18 shows the protecting member 250 engaged with the base part 200 as described above for FIG. 17. While the protecting member 250 is engaged with the base part 200, the protecting member 252 may be removed from the protecting member 250 and the base part 200. The needle 51 of the inserter 50 may be inserted into the membrane 3 of the cannula device 1 and extend through the cannula 4 in the first direction 18. The inserter 50 may be removed and replaced with the protecting member 252 or alternatively with a connector, such as a connector 450, 550, 650 described below, for delivery of a therapeutic substance.

Figure 19:
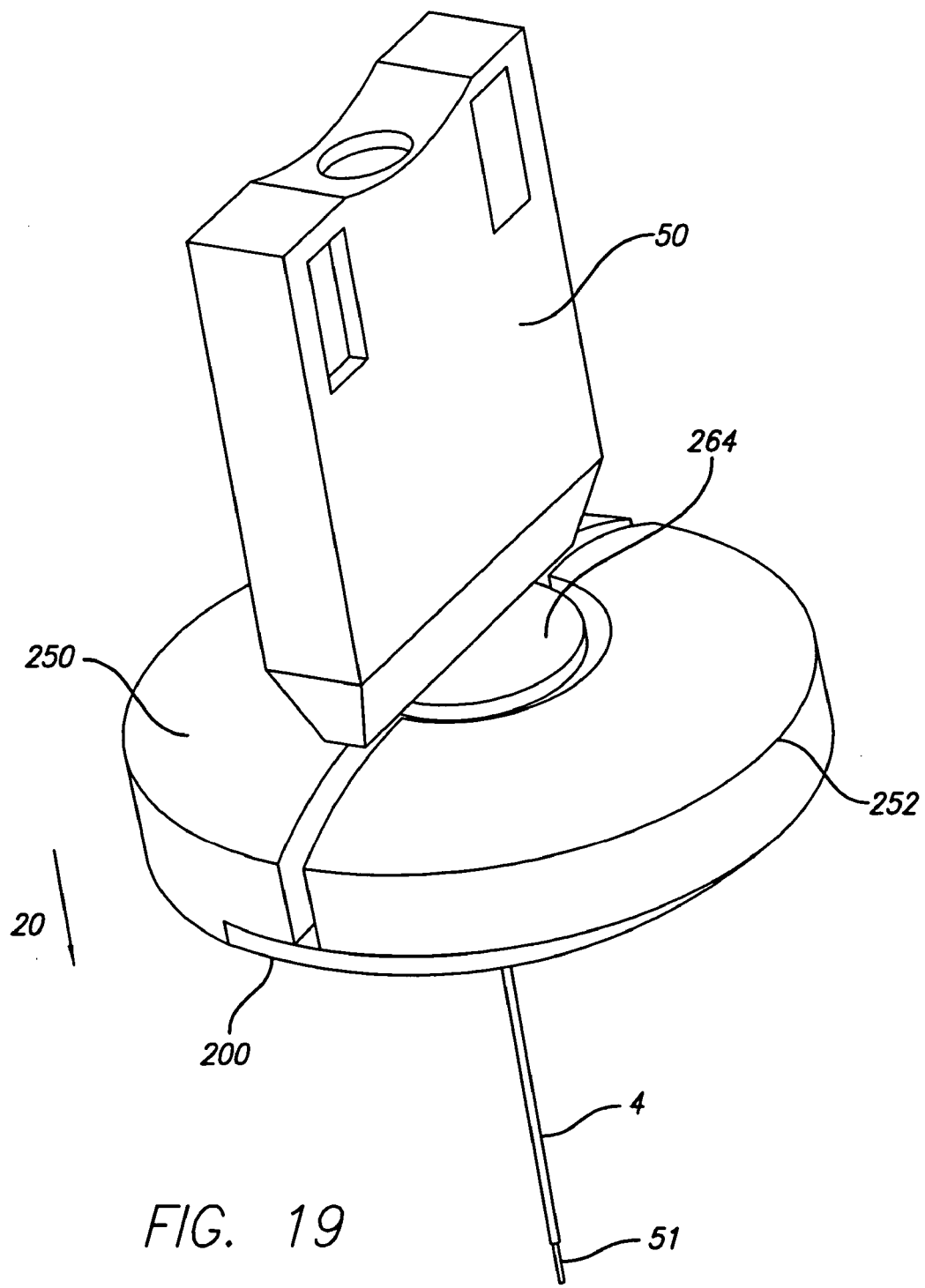
FIG. 19 is a perspective view of the embodiment shown in FIG. 18 with the inserter inserted in an orthogonal direction.

FIG. 19 illustrates the cannula device 1 (beneath the protecting members 250, 252) engaged with the base part 200 in the second direction 20 and the inserter 50 having needle 51 inserted into the cannula device 1 through the cannula 4 in the second direction. FIG. 19 shows the needle 51 penetrating the portion 264 of the protecting member 250. When the cannula device 1 is engaged with the base part 200 in the second direction 20, the protective members 250, 252 may remain engaged with the base part 200, protecting the base part 200 and the cannula device 1 while the needle 51 of the inserter 50 extends through the cannula 4.

Figure 20:
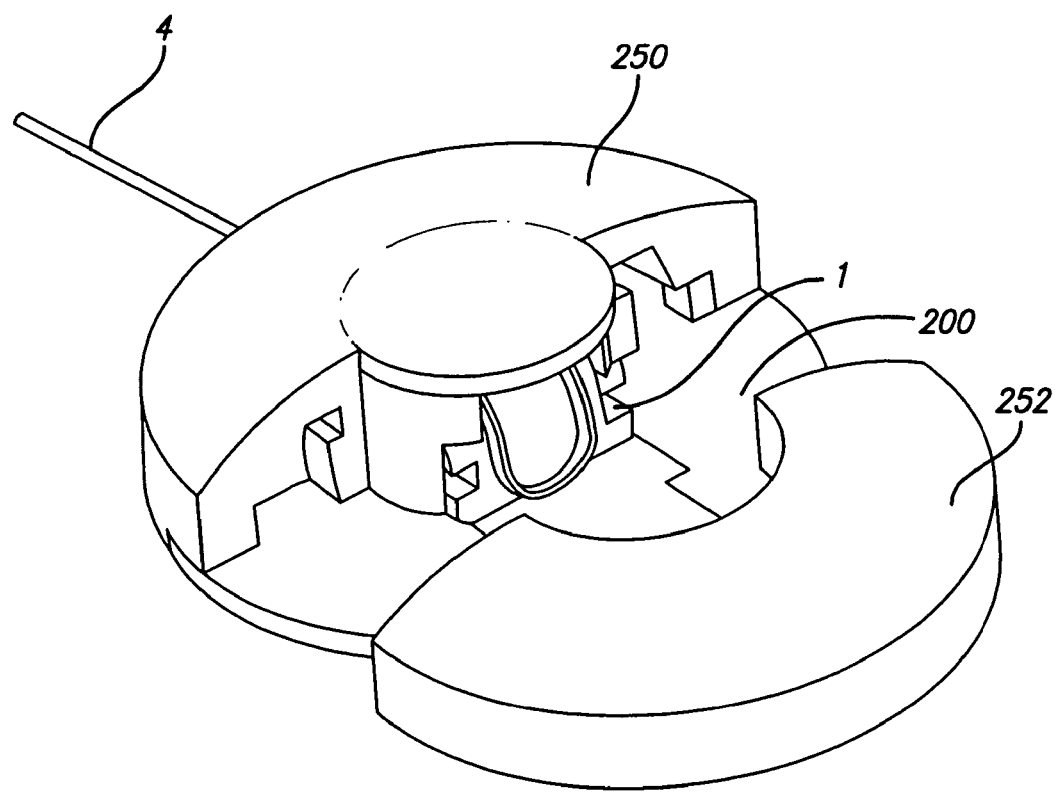
FIG. 20 is a perspective view of the embodiment shown in FIG. 18 with the inserter removed.
Figure 21:
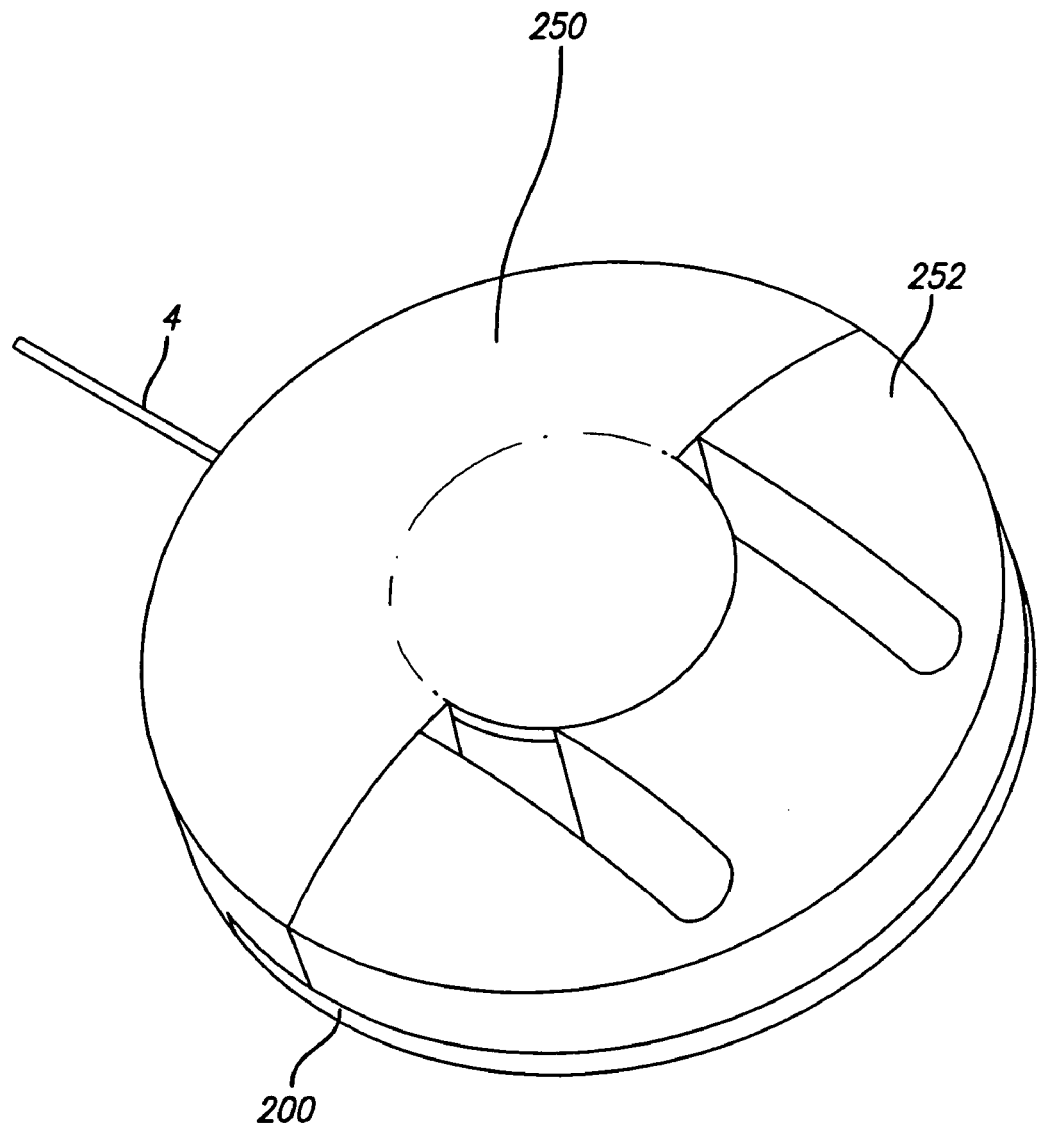
FIG. 21 is a top perspective view of the embodiment shown in FIG. 18 with the protective member engaged with the base part.

FIG. 20 illustrates the embodiment described above for FIG. 17 showing the protecting member 250 engaged with the base part 200 and the protecting member 252 not yet engaged. As shown, the protecting member 252 may be engaged parallel to the direction of the cannula 4 extending from the base part 200. FIG. 21 illustrates the compact size of the device when the protecting member 252 is engaged with the protecting member 250 and the base part 200. In this configuration, the more sensitive parts of the device are concealed and protected, and the assembly itself is easily transported or packaged. As described above, the protecting member 252 may be removed and a connector may be inserted in place of the protecting member 252, having a similar compact size.

Figure 22:
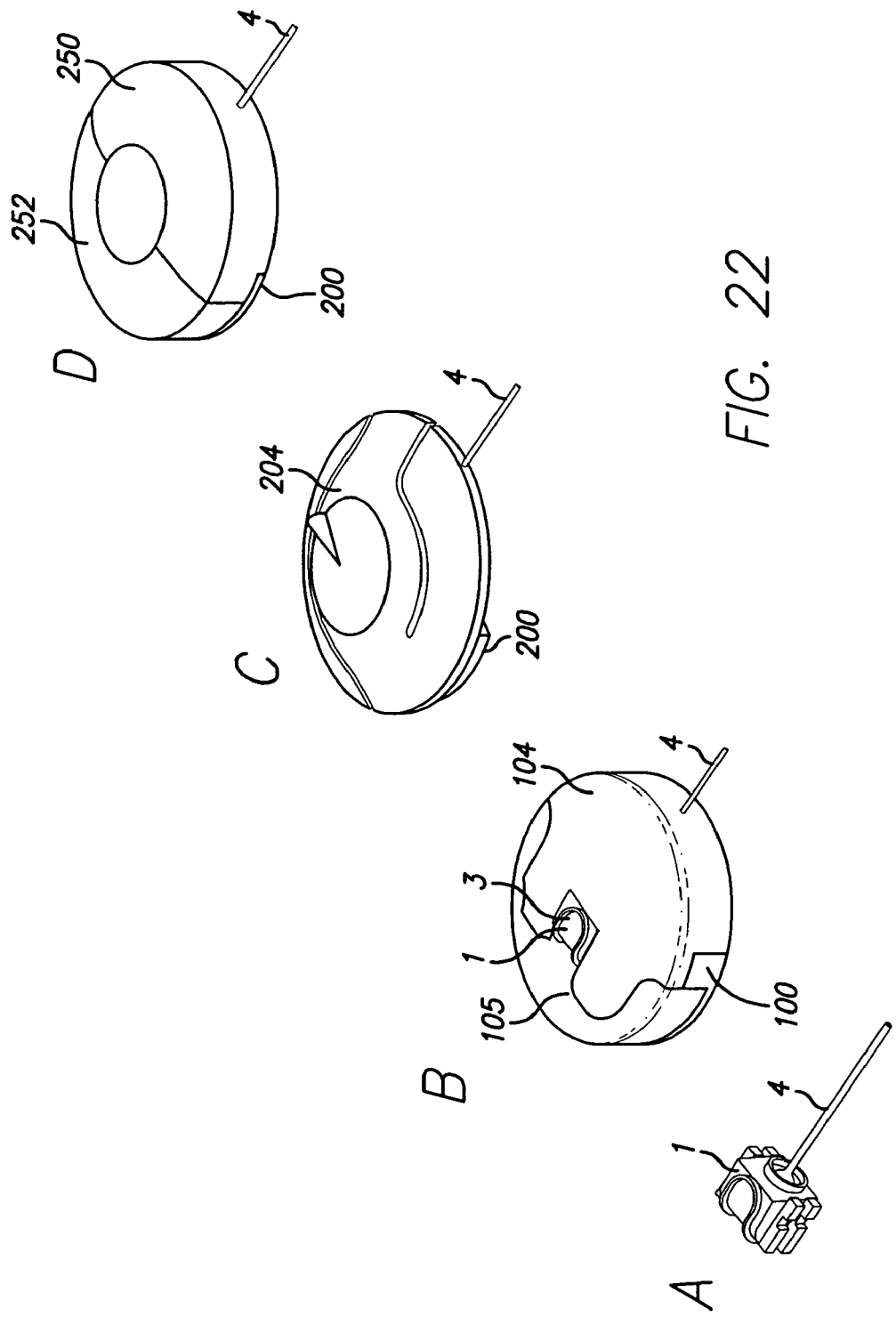
FIG. 22A shows the cannula device of FIG. 1.
FIGS. 22B-D show the cannula device of FIG. 22A having various protective members.
Figures 23, 24:
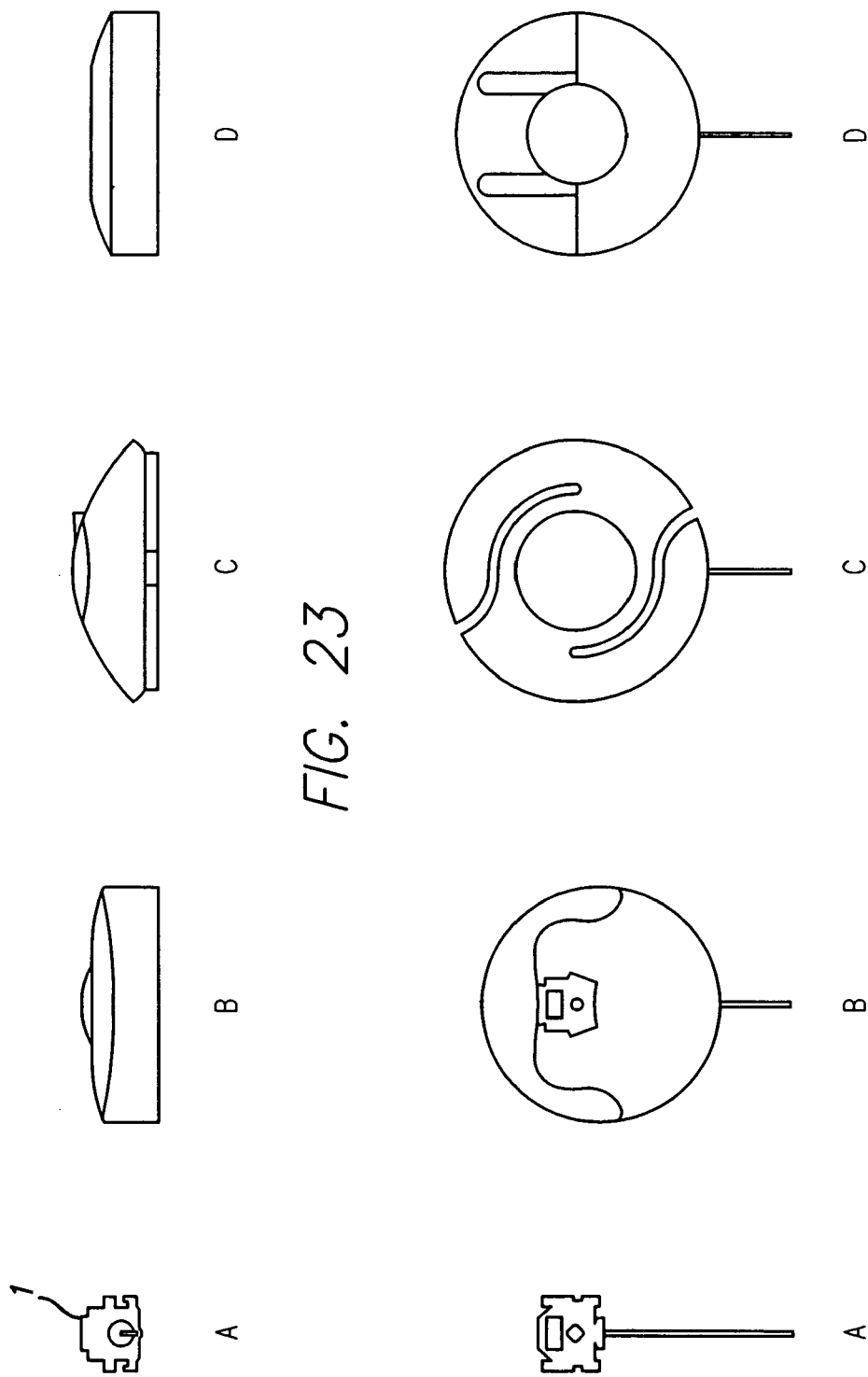
FIG. 23A-D show side views of the embodiments shown in FIGS. 22A-D.
FIG. 24A-D show top views of the embodiments shown in FIGS. 22A-D.

FIG. 22 illustrates perspective views of the cannula device 1 and includes several assembly configuration including the base parts 100, 200 and the protecting members 104, 105, 204, 250, 252. FIG. 22A shows the cannula device 1 itself. FIG. 22B shows the cannula device 1 inserted into the base part 100. The protecting members 104, 105 cover the base part 100 and the cannula device 1 with at least part of the membrane 3 accessible for insertion of a needle of an inserter or a connector for delivery of a therapeutic substance.

FIG. 22C shows the cannula device 1 engaged with the base part 200. The protecting member 204 is shown covering the cannula device 1 and the base part 200 and has been described above.

FIG. 22D shows the cannula device 1 engaged with the base part 200 and protecting members 250, 252 covering the device 1 and base part 200.

FIGS. 23A-D illustrate side views of the cannula device 1 engaged with the corresponding different embodiments shown in FIGS. 22B-D.

FIGS. 24A-D illustrate top views of the embodiments shown in FIGS. 22B-D respectively.

Figure 25:
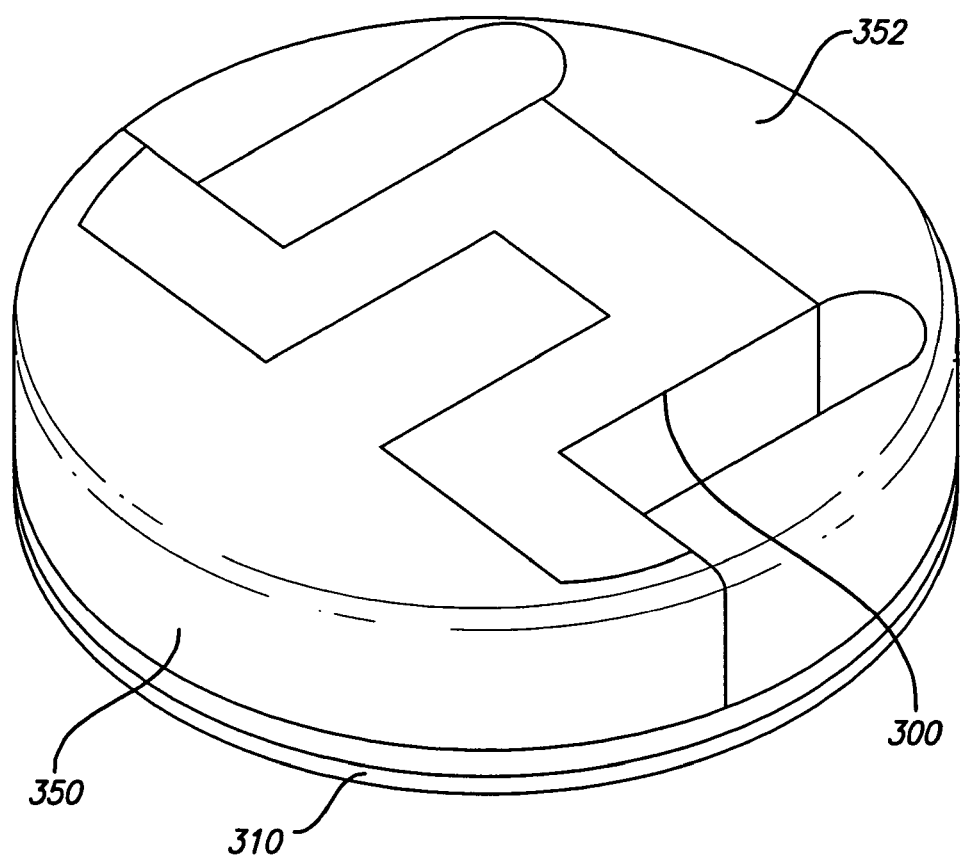
FIG. 25 is a perspective view of an embodiment of the present invention having a protective member.

FIG. 25 illustrates another embodiment of the present invention. As shown, a base part 300 is engaged with protecting members 350, 352 to form a compact device. An adhesive layer 310 for adhering the base part 300 to the patient's skin is shown connected to the base part 300.

Figure 26:
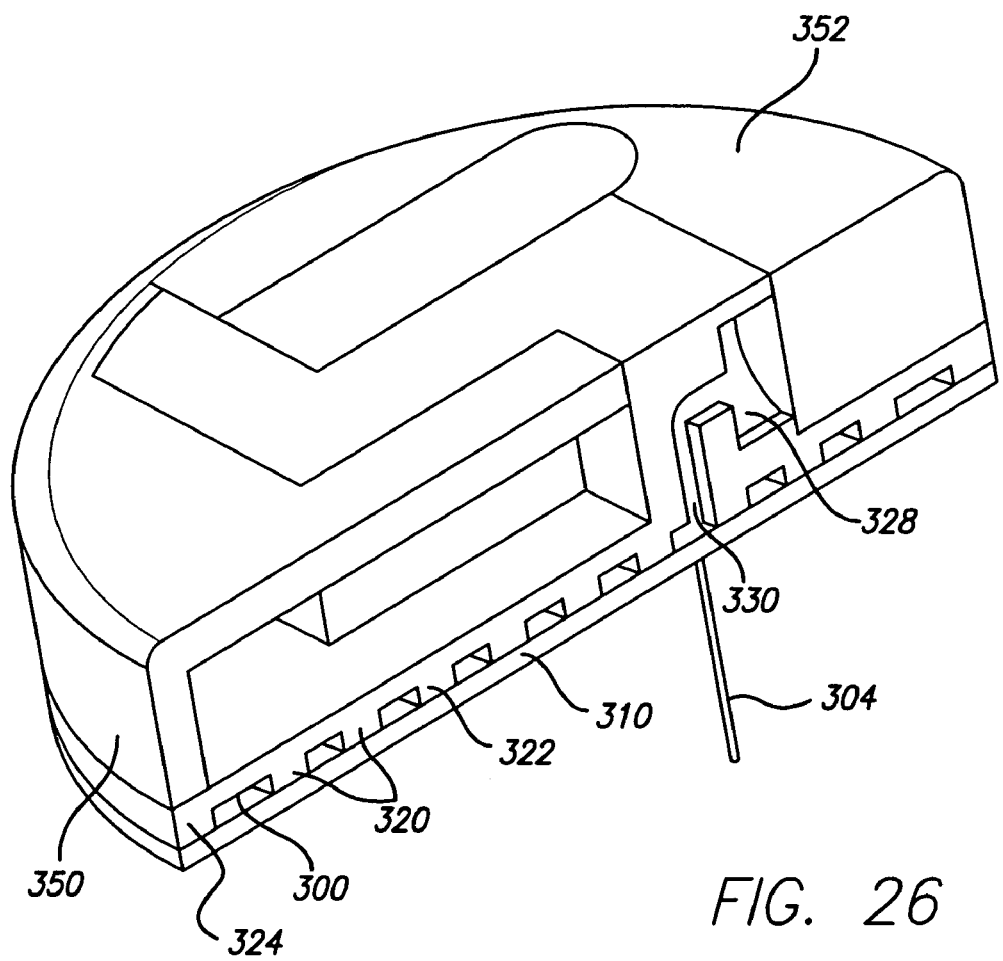
FIG. 26 is a sectional view of the embodiment shown in FIG. 25.
Figure 28:
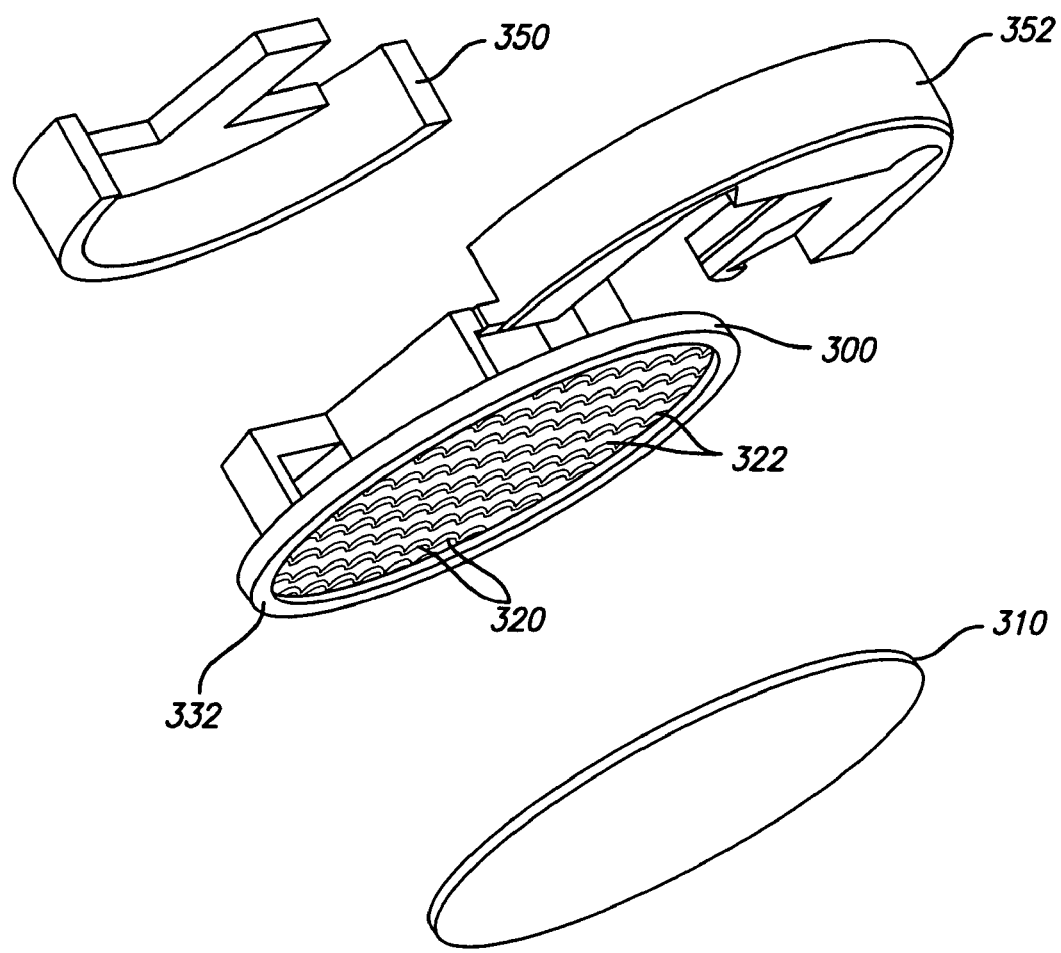
FIG. 28 is an exploded bottom view of the embodiment shown in FIG. 27.

FIG. 26 illustrates a sectional view of the embodiment shown in FIG. 25. The base part 300 includes a plurality of projections 320 having bottom surfaces 322 that together form the bottom surface 324 of the base part 300 as shown in FIGS. 26 and 28. An entry port 328 may be formed in the base part 300 wherein the entry port 328 is connected to a canal 330 that fluidly connects with a cannula 304 that extends from the base part 300. The protecting member 352 may be removed and a connector, such as the connector 450, 550, 650, described below, may be inserted at the same position for delivery of a therapeutic substance. The adhesive layer 310 adheres to the bottom surfaces 322 of the base part 300 and may be formed from a material that may be penetrated by a needle of an inserter (not shown) extending through the cannula 304. Alternatively, the adhesive layer 310 may include an opening through which the cannula 304 may extend.

Figure 27:
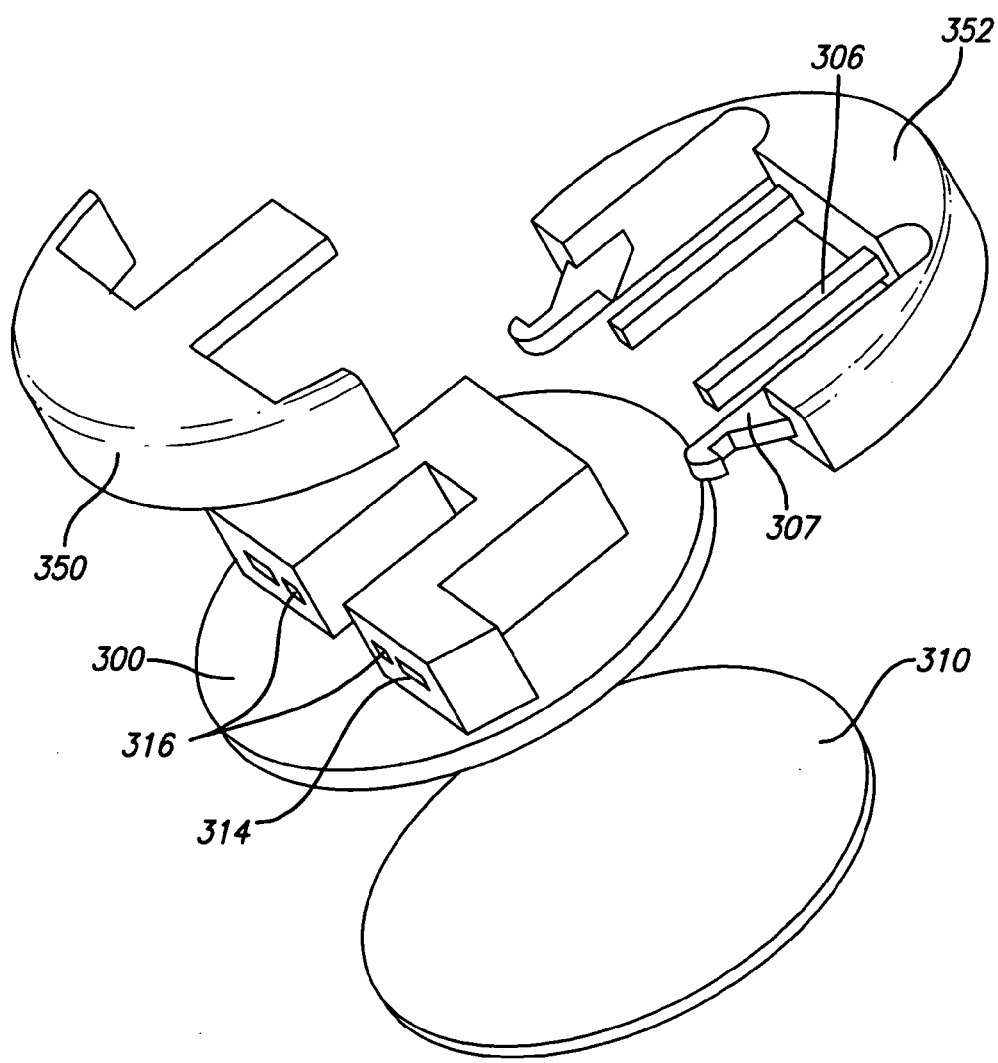
FIG. 27 is an exploded view of an embodiment of the present invention including adhesive layer.

FIG. 27 shows an exploded view of the embodiment shown in FIG. 25. As shown, the protecting member 352 includes guiding arms 306 and locking arms 307 for engagement of the protecting member 352 with the base part 300. The locking arms 307 may engage the base part 300 through corresponding openings 314 in the base part 200 as described above in FIGS. 5 and 6.

FIG. 28 shows an exploded bottom view of the embodiment shown in FIG. 25. The projections 320 having bottom surfaces 322 on the base part 300 are shown. The base part 300 may further include a peripheral surface 332 that extends around the periphery of the base part 300 to which the adhesive layer 310 may adhere in addition to the surfaces 322. As shown in the FIGS. 25-28, the general shape of the embodiment is cylindrical having the adhesive layer 310, the base part 300, and the protecting members 350, 352 shaped to fit together to form a compact device. One of skill in the art will recognize that alternative shapes are possible, including but not limited to oval, rectangular, and square shapes, preferably where the assembly of embodiment may form a compact device.

Figure 29A:
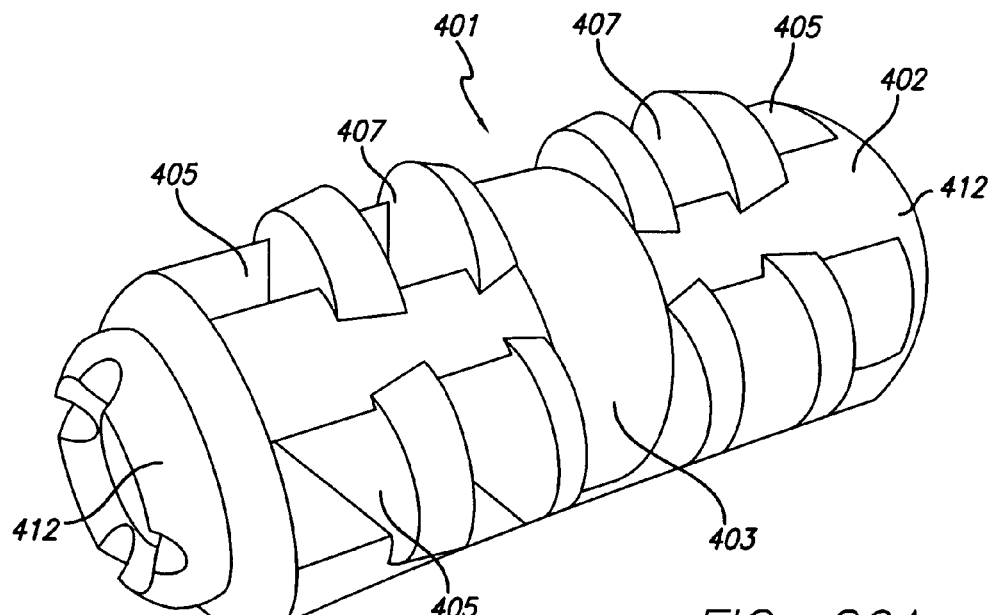
FIG. 29A is an another embodiment of the cannula device of the present invention.
Figure 29B:
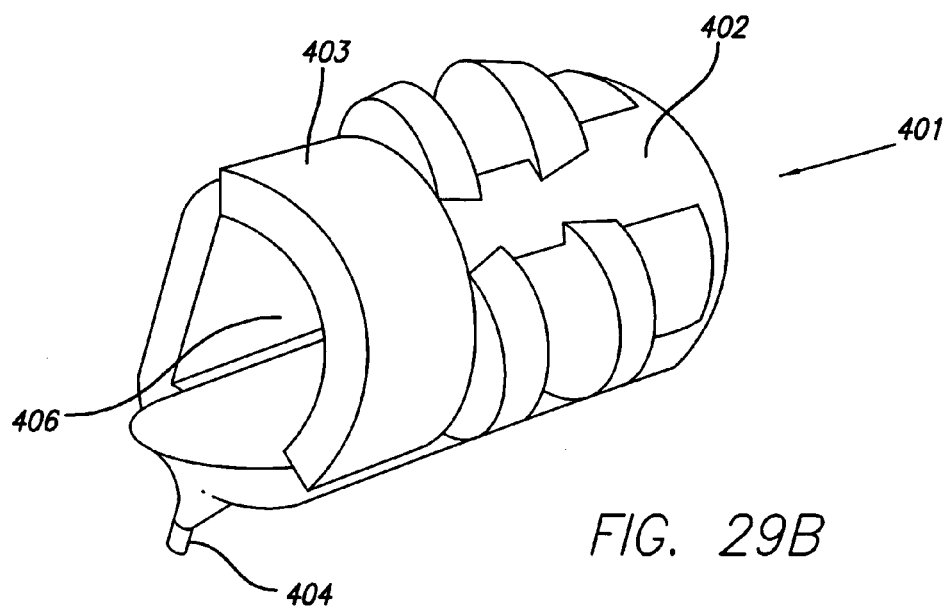
FIG. 29B is a partial sectional view of the embodiment shown in FIG. 29A.

FIGS. 29A and 29B show an alternative embodiment of a cannula device 401. The cannula device 401 includes a housing 402, a membrane 403 and openings 405, 407. Preferably, the housing 402 may be essentially cylindrically shaped, although other shapes are possible. In the present embodiment, the cylindrical shape includes radially extending projections 413 (or flanges) that define openings 405 and 407 and may be used as guides when positioned in a base part, such as base part 400, shown in FIG. 30 A. As shown in the sectional view in FIG. 29B, the membrane 403, together with the housing 402 define a cavity 406 within the housing 402 for reception of a cannula from a connector (described below). A cannula 404 extends from the housing 402 below the cavity 406 as shown in FIG. 29B. In this embodiment, the housing 402 may be rotatably attached to the base part 400, shown in FIG. 30, so that the rotatable attachment allows the housing 402 to rotate in the base part 400 after insertion of the cannula 404 into the skin of the patient, without movement of the cannula 404 and thereby minimizing pain to the patient. Alternatively, the base part 400 may be turned to a desired angle relative to the cannula 404 and then inserting the cannula 404 using an inserter such as inserted 50 shown in FIG. 4. As shown in FIG. 29A, end portions 412 protrude from the housing 402. Preferably, the end portions 412 may be generally circularly shaped to provide for rotation within the base part 400. However, the end portions 412 may be any size and shape that is movable within the base part 400 known to one of skill in the art.

Figure 30A:
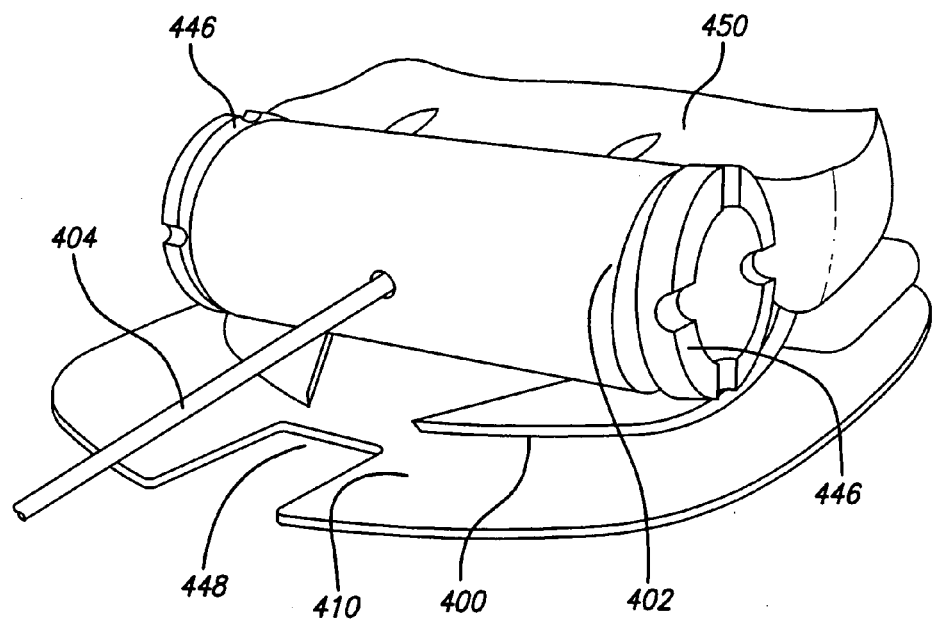
FIG. 30A is a front perspective view of the cannula device and a connector.

In FIGS. 30A and B, the cannula 404 of the cannula device 401 can be seen connected to the base part 400 and a connector 450. In this embodiment, the base part 400 includes connecting members 446 adapted to receive the end portions 412 of the housing 402. The connecting members 446 and the end portions 412 may be shaped and sized to facilitate rotation of the housing 402 with respect the base part 400. The device 401 further includes an adhesive layer 410 for adhering the base part 400 to the patient's skin. The adhesive layer 410 is shown connected to the base part 400 and the adhesive layer 410 may include a cutout 448 for the cannula 404 when the end portion 412 of the housing 402 is rotated in the connecting member 446 of the base part 400 to change the angle of the cannula 404 with respect to the skin.

The connector 450 connects to the cannula device housing 402 via openings 405, 407 in the housing 402. (Also shown and described below with reference to FIG. 31A.) The connector 450 may further include tubing 452 for delivering a therapeutic substance to the cannula 404 for delivery to the patient. The connector 450 may include a button 454 for release of the connector 450 from the housing 402. Alternatively, any method for releasing the connector 450 from the housing 402 may be used, including, but not limited to pressing on an exterior portion 456 on each side of the connector 450 to release gripping arms 458 (shown in FIG. 31A).

Figure 31A:
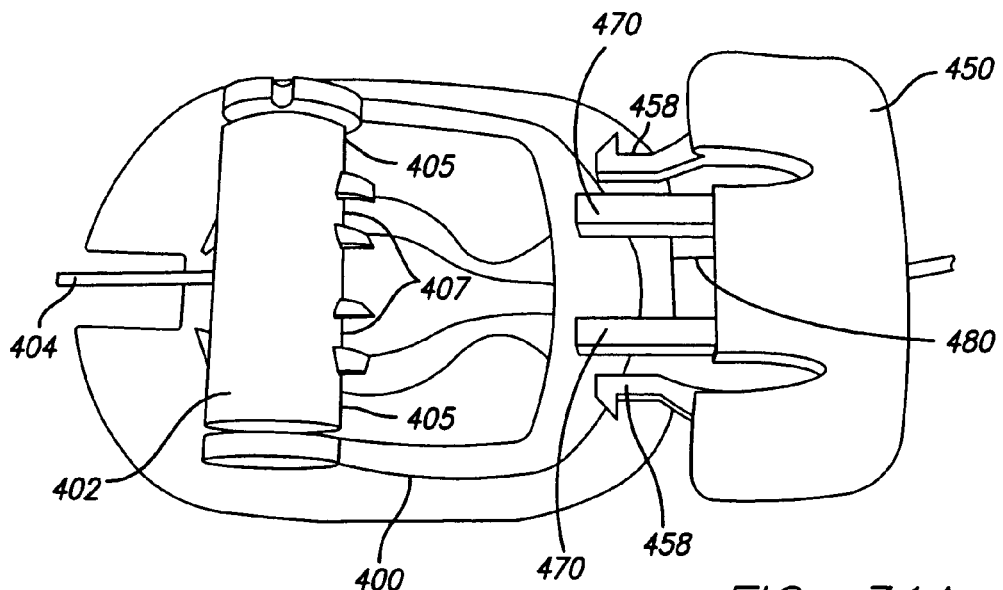
FIG. 31A is an exploded top view of the cannula device, the base and the connector.

FIG. 31A illustrates the connector 450 prior to connection with the housing 402. The connector 450 may include locking arms 458 and guiding members 470 similar to the locking arms and guiding members described above for the protecting member with the cannula device 1. The locking arms 458 allow the connector 450 to be inserted into the openings 405 of the housing 402 and be removably locked in place for delivery of the therapeutic substance. The connector 450 may also include a piercing member 480 that connects the connector 450 to the cannula 404. The piercing member 480 may be inserted through the membrane 403 and into the cannula 404 or into the chamber 406 to fluidly connect with the cannula 404. The piercing member 480 may be adapted to be broken at a predetermined place. This allows the connector 450 to be used as an inserter for inserting the cannula 404 of the cannula device 401. Then the piercing member 480 may be broken at the desired spot and the connector 450 used in the traditional manner. The piercing member 480 extends through the membrane and may piece the membrane, but does not necessarily have to puncture the membrane. For example, the piercing member may be inserted through a pre-formed hole in the membrane. The term piercing member as used herein may include a cannula, including a rigid cannula or a needle, a semi-rigid cannula, or a soft cannula or any member suitable piercing the membrane.

Figure 31B:
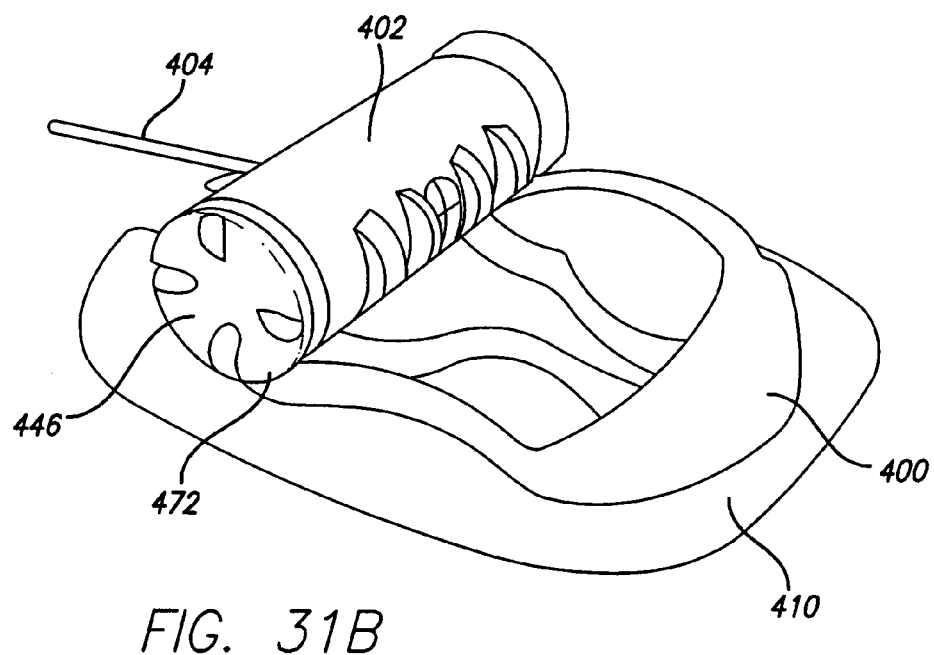
FIG. 31B is a perspective view of the cannula device and base part of the embodiment shown in FIG. 31A.

As shown in FIGS. 31A and B, the base part 400 of this embodiment may be flexible or hinged to facilitate the rotation of the housing 402 in the base part 401. FIG. 31B illustrates the cannula 404 rotated toward the skin and the base part 400 flexing for rotation. The base part 401 may further include hinges 472 joined to the connecting members 446. The hinges 472 may be used for rotating the cannula 404 from parallel to the skin to angled toward the skin. Rotation of the housing 402 also allows the cannula 404 to be placed into the skin with an injector needle, such as the needle 51 shown with the cannula device 1. The connector 450 may be connected at any angle and the insertion device 480 can be inserted into the membrane 403 from a plurality of directions.

Figure 32A:
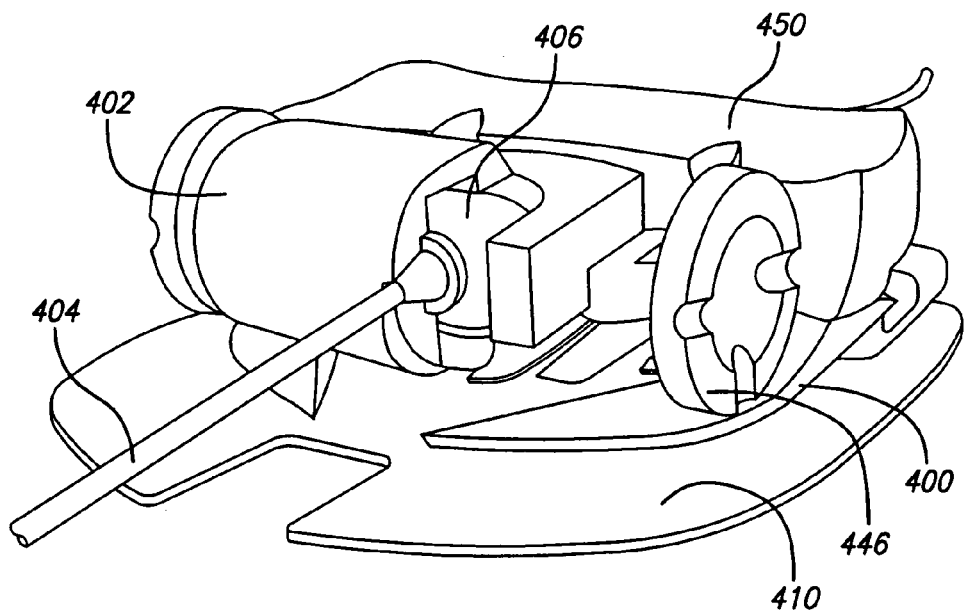
FIG. 32A is a sectional view of the embodiment shown in FIG. 31A.
Figure 32B:
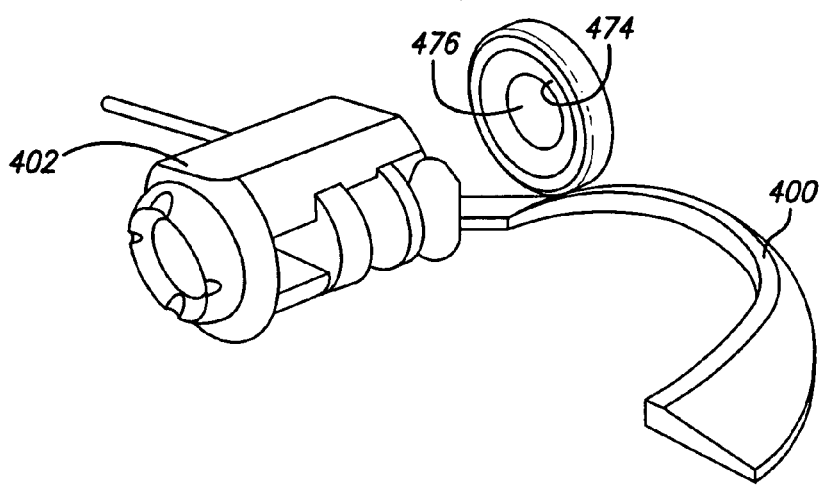
FIG. 32B is a sectional view of the embodiment shown in FIG. 31B.
Figure 32C:
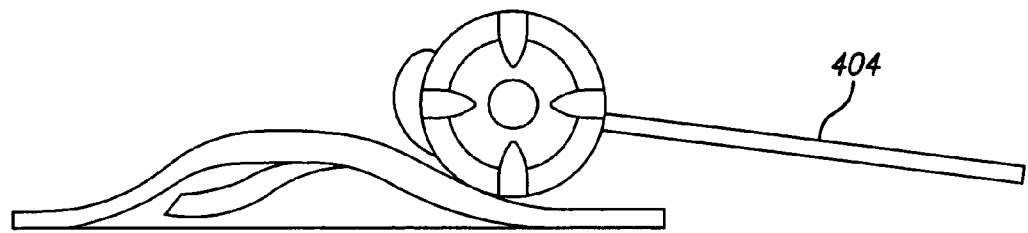
FIG. 32C is a side view of the embodiment shown in FIG. 31B.
Figure 32D:
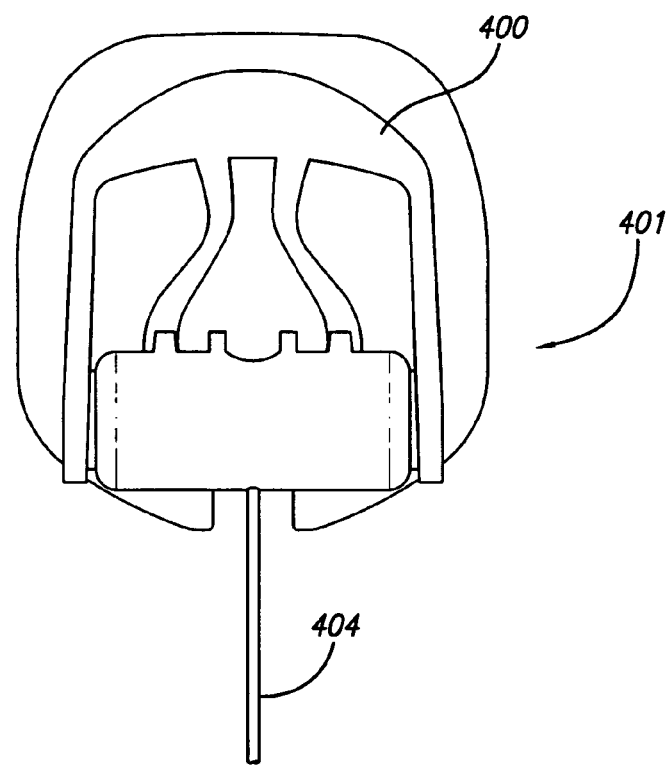
FIG. 32D is a top view of the embodiment shown in FIG. 31B.

FIG. 32A shows the cavity 406 formed in the housing 402 and the cannula 404 extending from the cavity 406. FIG. 32B shows a portion of the housing 402 cut away from the base part 400. The connecting member 446 is shown in a circular configuration having a raised circumference 474 and a central depression 476 adapted to receive the end portion 412 of the housing 402. A portion of the base part 400 is shown extending from the connecting member 446. FIG. 32C shows the cannula 404 rotated from the direction parallel to the skin. FIG. 32D shows a top view of the cannula device 401.

Figure 30B:
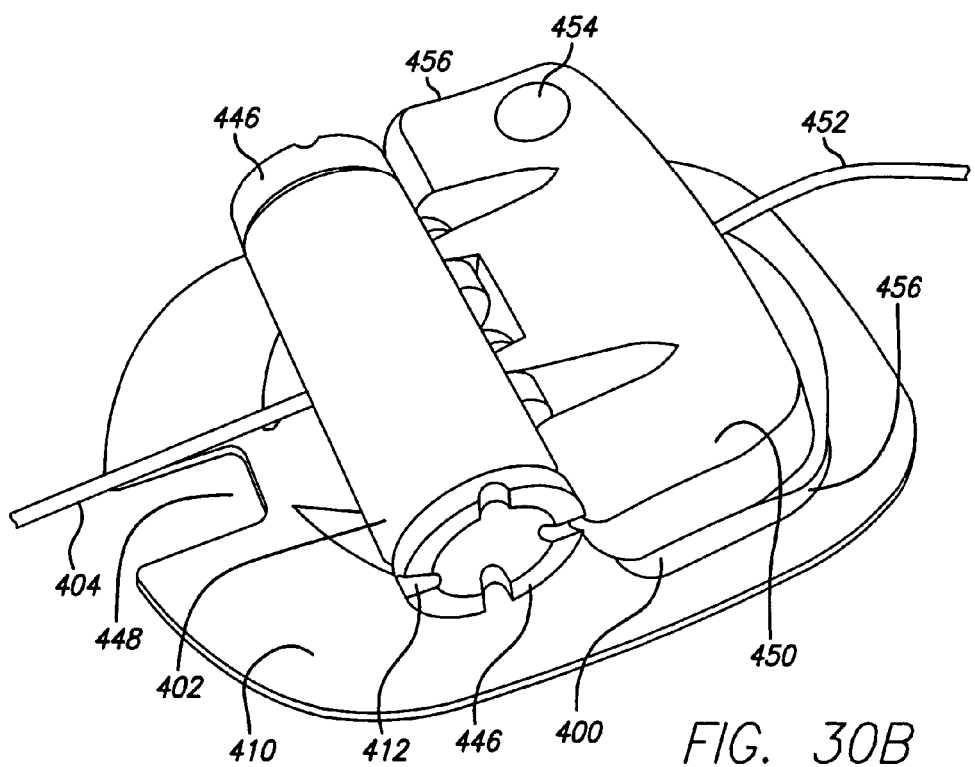
FIG. 30B is top perspective view of the embodiment shown in FIG. 30A.
Figure 33A:
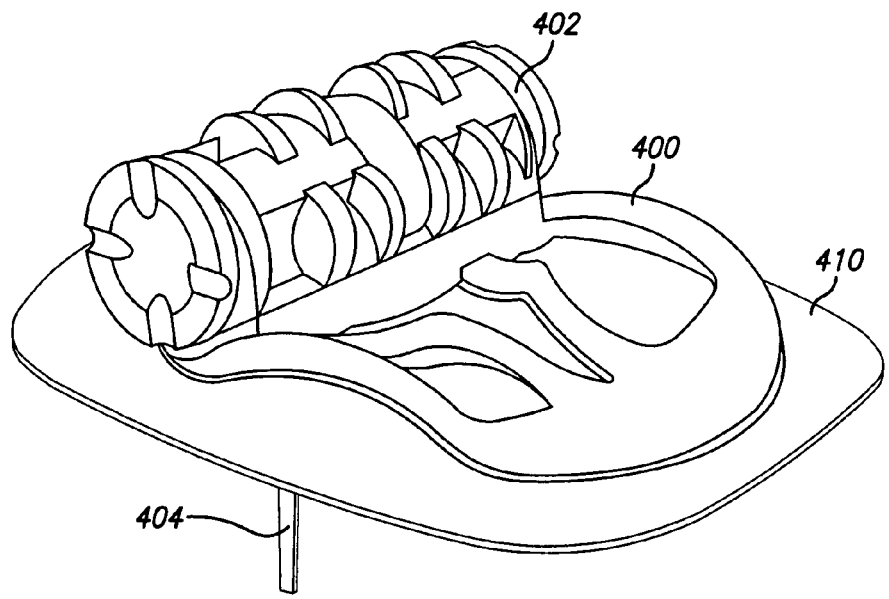
FIG. 33A is a perspective view of the cannula device shown in FIG. 31B with the cannula device in an orthogonal direction.
Figure 33B:
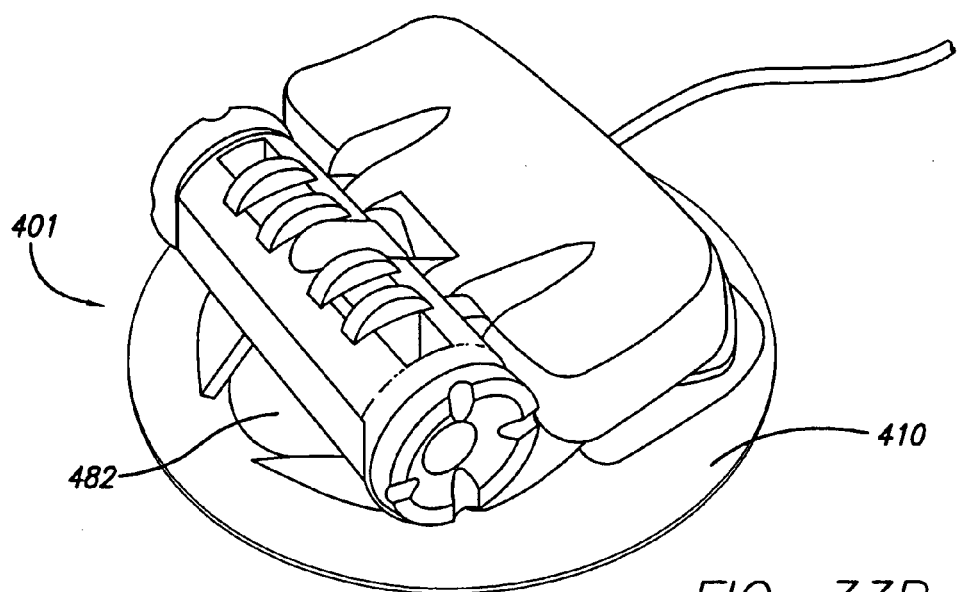
FIG. 33B is a perspective view of the cannula device shown in FIG. 31A with the cannula device in an orthogonal direction.
Figure 33C:
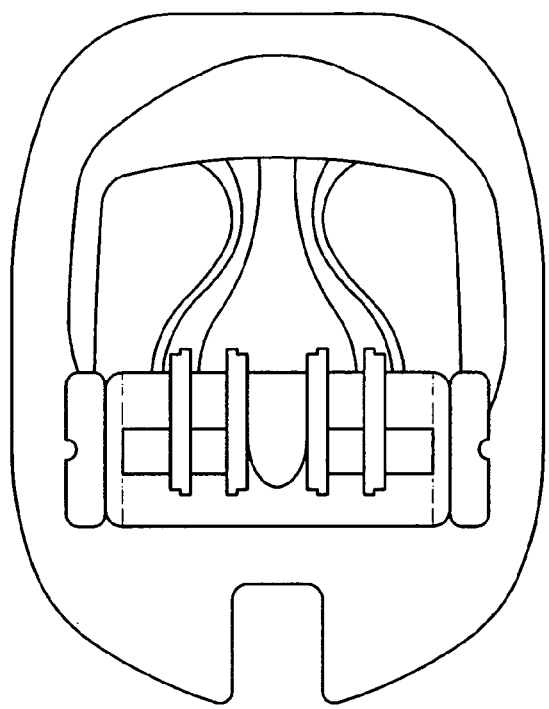
FIGS. 33C and D show top views of the embodiments shown in FIGS. 33A and B respectively.
Figure 33D:
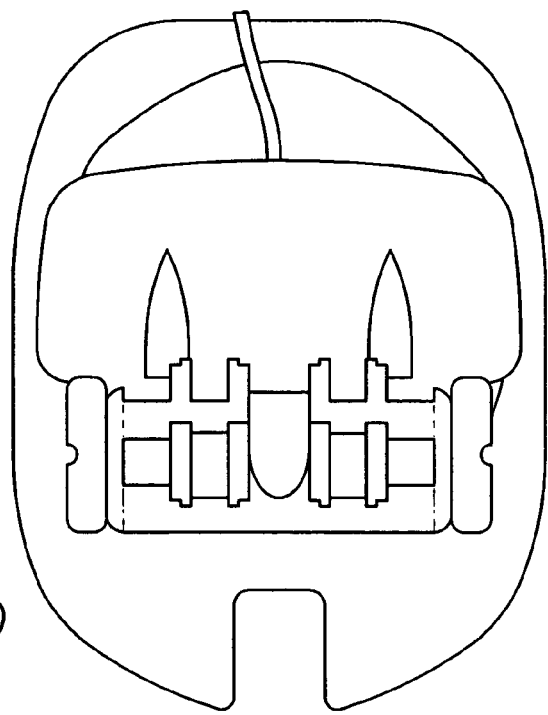

FIGS. 33A-D illustrate the cannula device 401 having the cannula 404 extending in a different direction as previously shown in FIGS. 30-32. The cannula 404 is shown extending substantially orthogonally with respect to the cannula 404 shown in FIGS. 31-32. FIG. 33B shows the cannula device 401 with the cannula 404 extending vertically from the base part 400. The connector 450 is shown removably connected to the housing 402 in the openings 405, 407 of the housing 402. An opening 482 in the adhesive layer 410 is shown in FIG. 33B for the cannula 404 to extend through and into the skin of the patient. FIGS. 33C and D show top views of the cannula device 401 shown in FIGS. 33A and B, respectively.

Figure 34A:
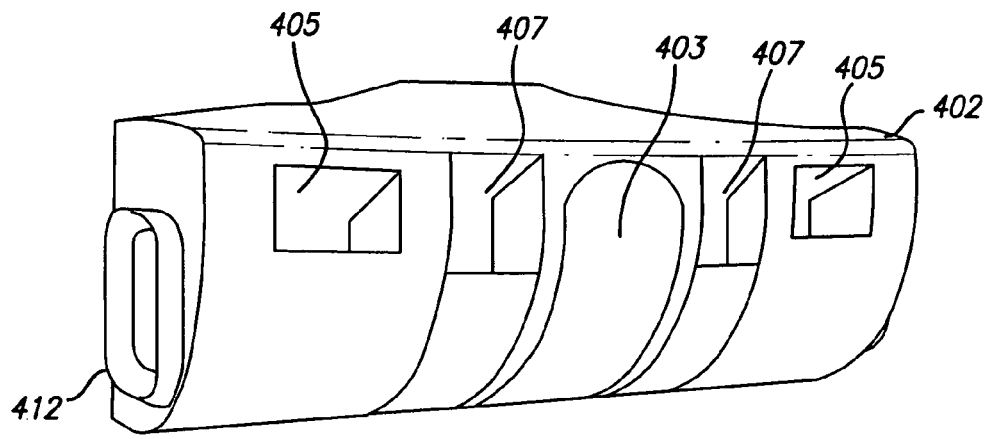
FIG. 34A is a front perspective view of an embodiment of the cannula device.
Figure 34B:
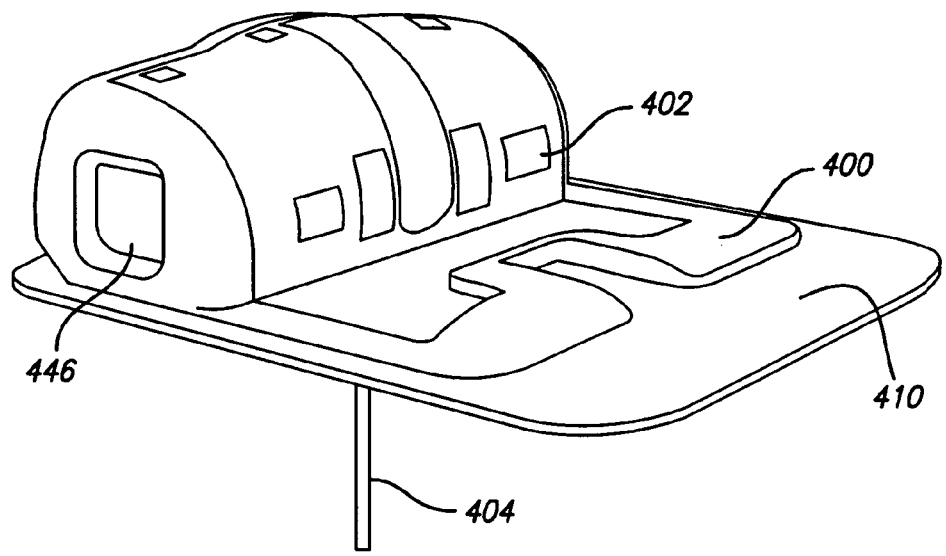
FIG. 34B is a perspective view of an embodiment of the cannula device, the base part and the adhesive layer.

FIG. 34A illustrates the housing 402 having openings 405, 407. The membrane 403 is shown in the center of the housing 402 for reception of an insertion device for fluidly delivering a therapeutic substance through the cannula 404. The end portion 412 is shown having a generally rectangular shape for mating with a similarly shaped connecting member 446 of the base part 400 shown in FIG. 34B. The housing 402 is rotatable in the base part 400 as described above.

Figure 35:
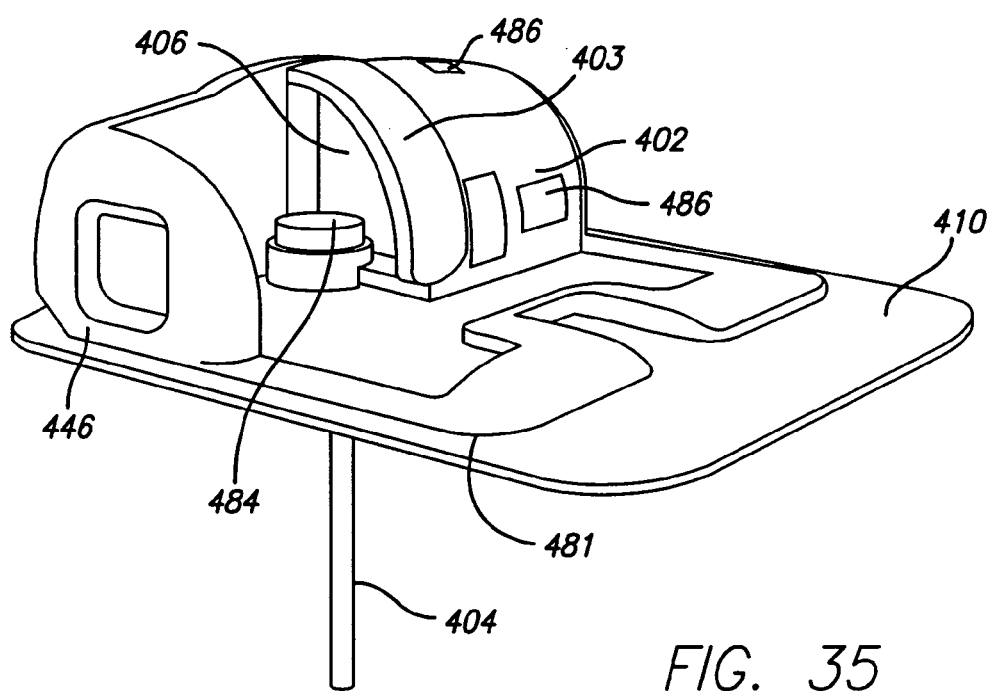
FIG. 35 is a sectional view of the embodiment shown in FIG. 34B.

FIG. 35 shows the cavity 406 formed inside the housing 402. The membrane 403 may cover a portion of the cavity 406. A top portion 484 of the cannula 404 connects with the cavity 406 in the housing 402. The cavity 406 allows for an piercing member of a connector to be inserted into the membrane 403 in any reception direction and have the cannula 404 be in fluid communication with the connector for delivery of the therapeutic substance. In this embodiment, the cannula 404 is shown extending vertically from the housing 402 in relation to the plane 418 of the base part 400. A pair of openings 486 is shown on the housing 402 for reception of a connector or a protective member in two different directions. The base part 400 also includes the connecting member 446 in a generally square shape for reception of the end portion 412 of the housing 402. The adhesive layer 410 may be adhered to the skin of the patient.

Figure 36A:
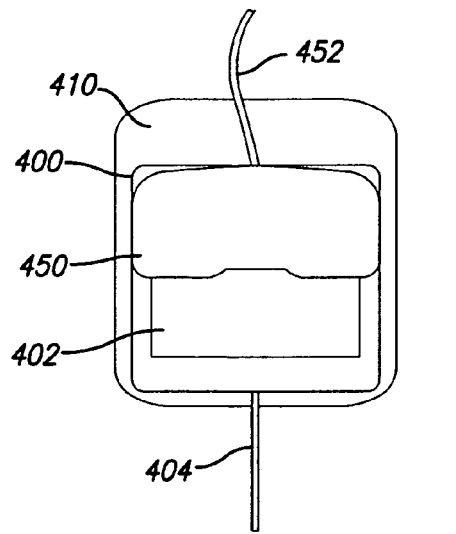
FIGS. 36A-E are top and perspective views of an embodiment of the present invention.
Figure 36B:
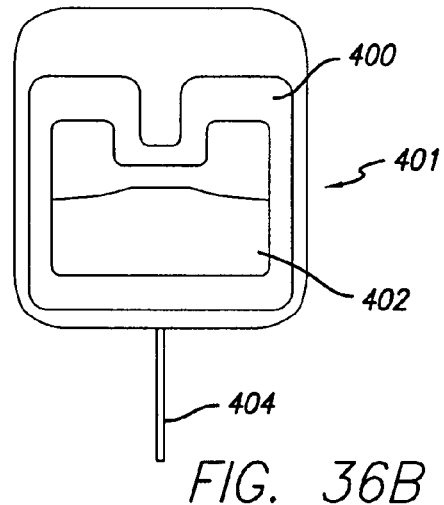
Figure 36C:
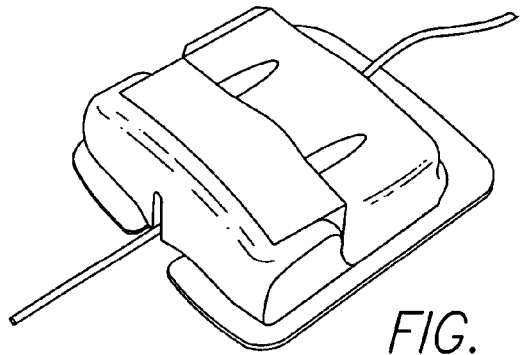
Figure 36D:
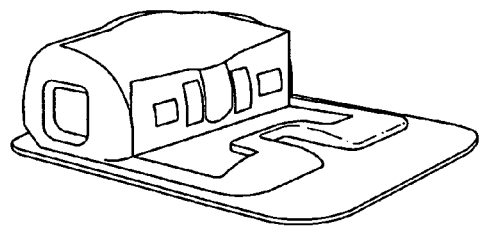
Figure 36E:
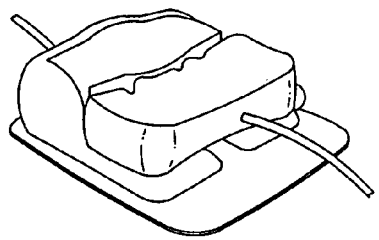

FIGS. 36A-E show the cannula device 401 from different angles. FIG. 36A shows a top view of the cannula device 401 with the connector 450 connected to the housing 402. The cannula 404 is shown extending in a direction generally parallel to the base part 400. Tubing 452 extends from the connector 450 for connection to a medical device (not shown) for delivery of a therapeutic substance. FIG. 36B shows the cannula device 401 from FIG. 36A with the connector 450 removed. FIG. 36C shows a perspective view of the cannula device 401 of FIG. 36A. FIG. 36D shows a rear perspective view of the cannula device 401 and FIG. 36E shows a rear perspective view of the cannula device 401 with the connector 450 connected to the housing 402.

Figure 37A:
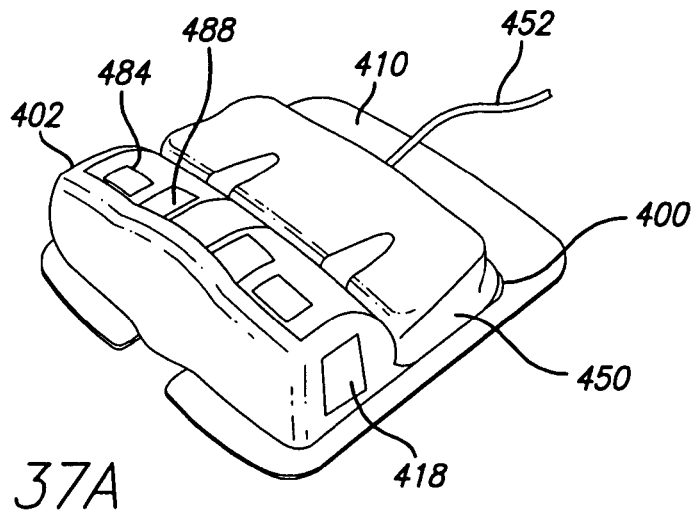
FIG. 37A is a top perspective view of the cannula device and the connector showing the cannula in an orthogonal direction.
Figure 37B:
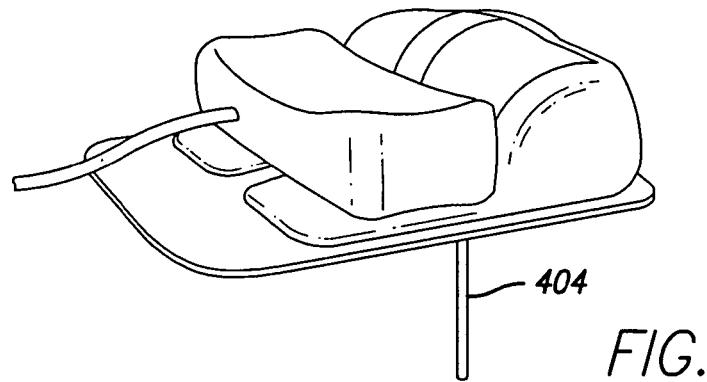
FIG. 37B is a side perspective view of the embodiment shown in FIG. 37A.
Figure 37C:
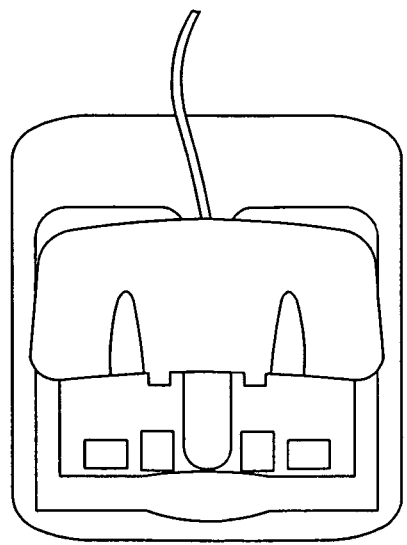
FIG. 37C is a top view of the embodiment shown in FIG. 37A.

FIGS. 37A-C illustrate the cannula device 401 with the cannula 404 extending in a direction generally vertically to the plane 418 of the base part 400. FIG. 37A shows the connector 450 connected in one set of the openings 484 in the housing 402 wherein the connection is parallel to the plane of the base part 400. The second set of the pair of openings 488 are shown opening in a second direction that the connector 450 may be inserted into wherein the connection is generally orthogonal to the plane 418 of the base part 400. FIG. 37B shows a side perspective view of the cannula device 401 and the cannula 404 extending below the base part 400. FIG. 37C shows a top view of the device shown in FIG. 37A.

Figure 38A:
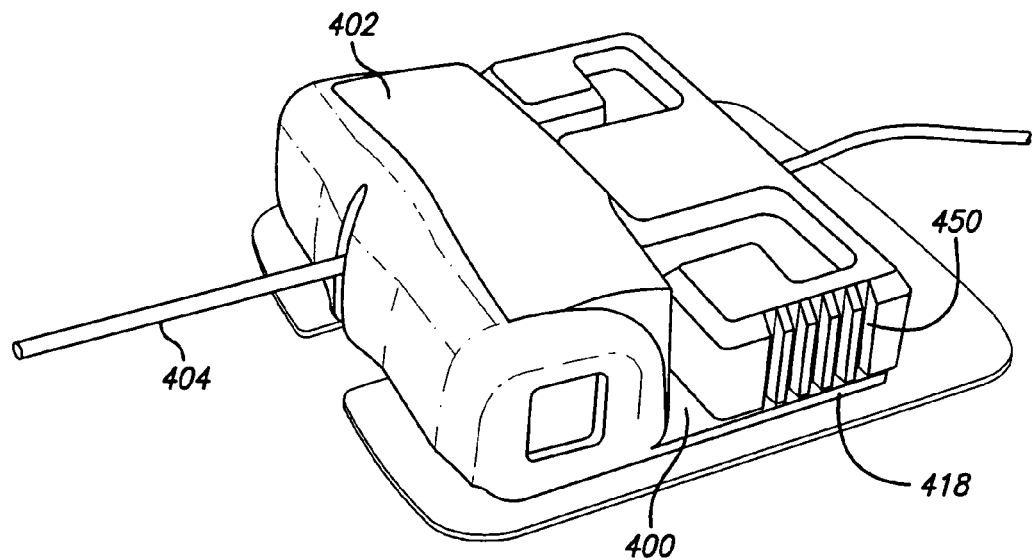
FIG. 38A is a side perspective view of the cannula device and the connector showing the cannula in a parallel direction.
Figure 38B:
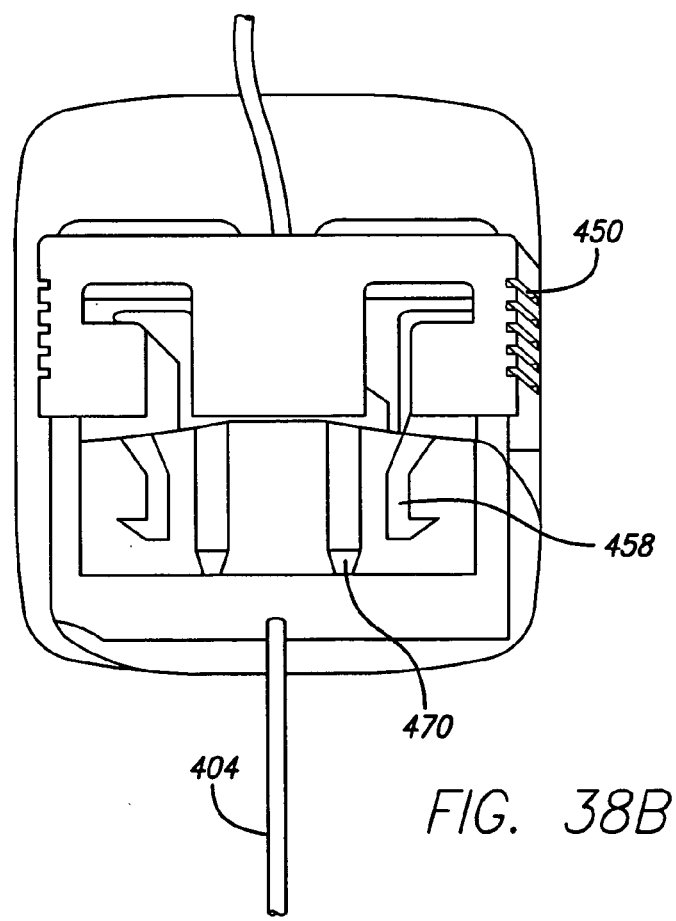
FIG. 38B is a top view of the embodiment shown in FIG. 38A.

FIG. 38A shows the cannula device of FIG. 37A with the housing 402 repositioned in the base part 400 so that the cannula 404 extends generally parallel main plane 418 of the base part 400. The connector 450 is shown connected to the housing 402 in a parallel direction to the plane 418 of the base part 400. FIG. 38B is a top view of the cannula device 401 shown in FIG. 38A where the guiding arms 470 and the locking arms 458 from the connector 450 can be seen connected to the housing 402 for removable connection.

Figure 39:
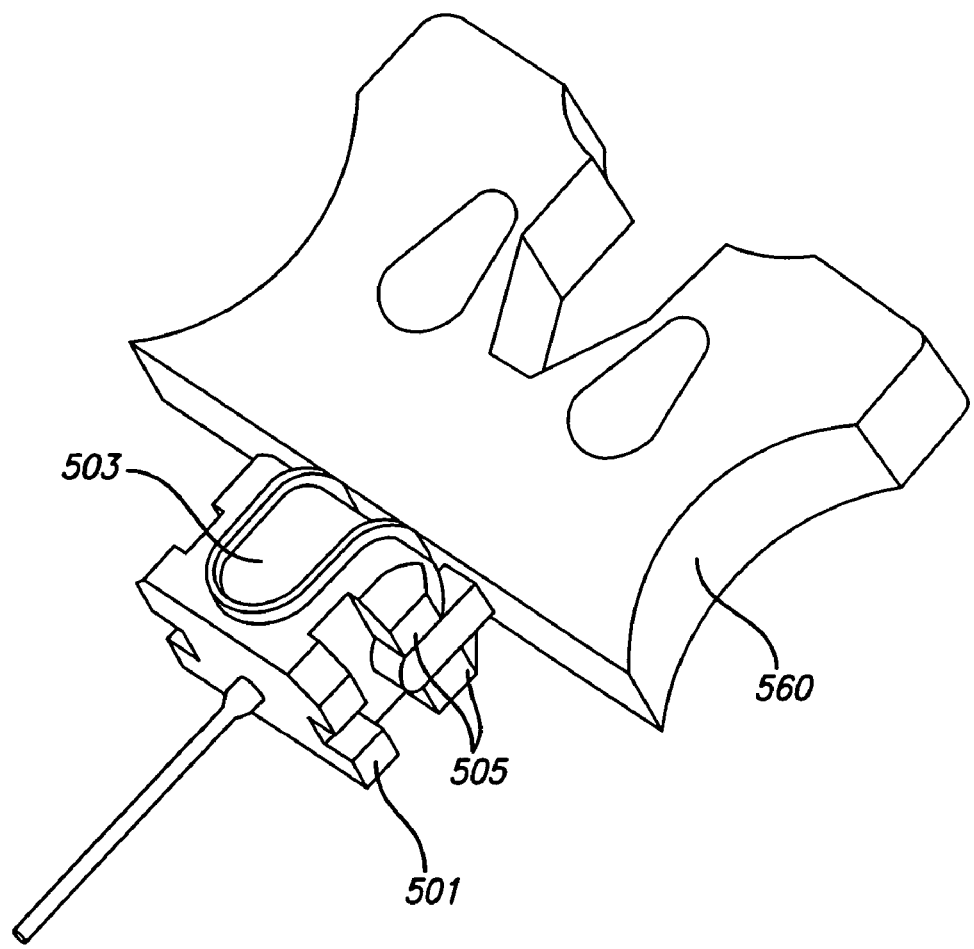
FIG. 39 is a perspective view showing an inserter with the cannula device.

FIG. 39 illustrates a cannula device 501 connected to an inserter 550. The cannula device 501 is shown removed from a base part to show the connection of the inserter 560 with the guiding members 505 of the cannula device 501.

Figure 41A:
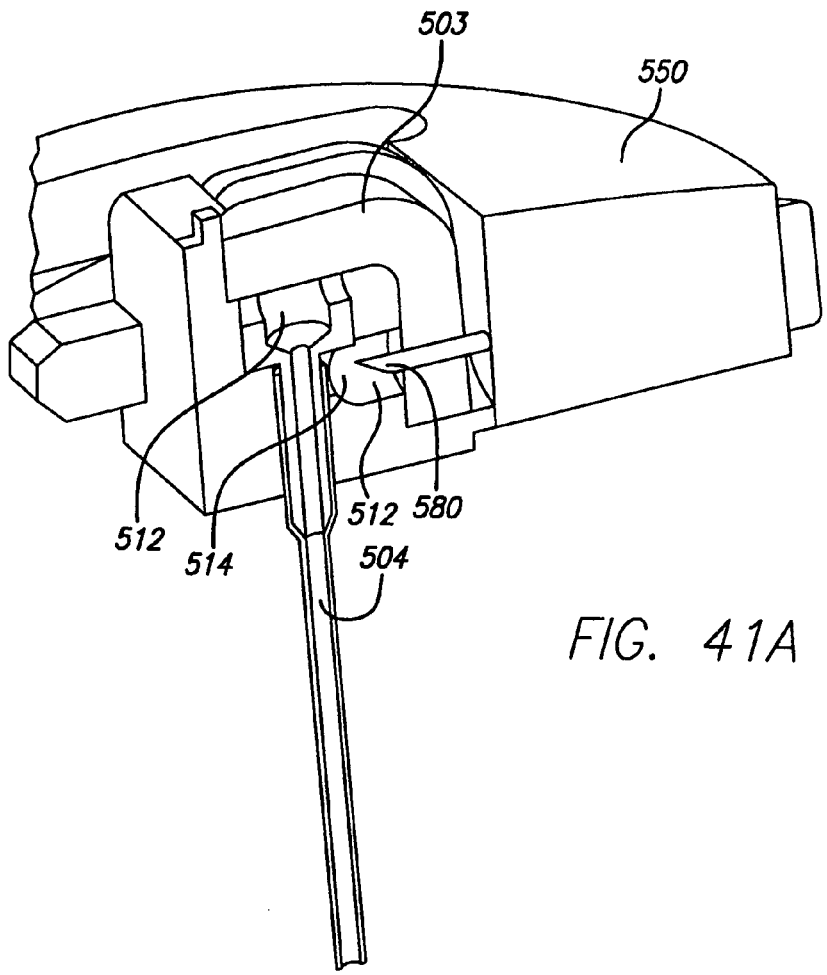
FIGS. 41A and B are sectional views of the embodiment shown in FIGS. 41A and B respectively.

As shown in FIGS. 40A and B, the cannula device 501 may be connected to a connector 550 at different heights and distances from skin of the patient so that the cannula 504 may extend into the skin of the patient in varying depths. A positioning member 507 is shown in FIGS. 40A and 41A positioned beneath the cannula device 501. The positioning member 507 may be positioned between a base member 500 (shown in FIG. 43) and the cannula device 501 for changing the height and distance that the cannula 501 may be inserted into the skin. The positioning member 507 allows the cannula device 501 to be positioned higher in the connector 550 in FIG. 40A when compared to the position of the cannula device in the connector 550 in FIG. 40B without a positioning member (see also FIGS. 41A and 41B). The cannula device may also be positioned at multiple heights with respect to the base part using multiple guiding members. Multiple positions of the cannula device with respect to the base part allow one cannula device and one base part together to be used for more than one insertion depth, adapting the infusion set to the individual patient and also so that the infusion set may also be used for both children and adults. The cannula device 501 also includes a membrane 503 that is adapted to receive a piercing member 580, such as a cannula, from the connector 550 to fluidly connect the connector 550 to the cannula 504 for delivery of a therapeutic substance. As will be understood by one of skill in the art, the cannula may be rigid, for example, but not limited to, a needle, semi-rigid, or soft.

FIGS. 41A and B show a partial view of the embodiments shown in FIGS. 40A and B, respectively. FIG. 41A illustrates an embodiment that allows the connection of the cannula device 501 with the connector 550 from two different directions. As shown, the membrane 501 is a single membrane mounted to the housing 502. As described blow, multiple members 503 are possible. The piercing member 580, shown as a cannula, may extend from the connector 550 and penetrate the membrane 503 and depending on the direction from which the piercing member 580 is received in the cannula device 501, the piercing member 580 may end in one of two cavities 512 formed in the cannula device 501. The two cavities 512 may be in fluid communication with each other via a canal 514 formed in the cannula device 501. Preferably the canal 514 is provided in the interior of the housing 502. This embodiment allows the piercing member 580 to be in fluid communication with the cannula 504 regardless of the direction from which the insertion device is inserted through the membrane 503. As shown in FIG. 41A, the piercing member 580 may be essentially orthogonal with the cannula 504 of the cannula device 501 and the cavity 512, in to which the piercing member 580 inserts and ends, fluidly connects the canal 514 and a cavity 516 connected to the cannula 504. One of skill in the art will recognize that the piercing member 580 may also be inserted into the membrane 503 from a direction essentially parallel to the cannula 504 from the top of the cannula device 501. The piercing member 580 may also be inserted through the membrane 503 and the piercing member 580 may end in the cannula 504 and thus the piercing member 580 may fluidly connect directly with the cannula 504 without connecting via a cavity 512 or a canal 514.

Figure 41B:
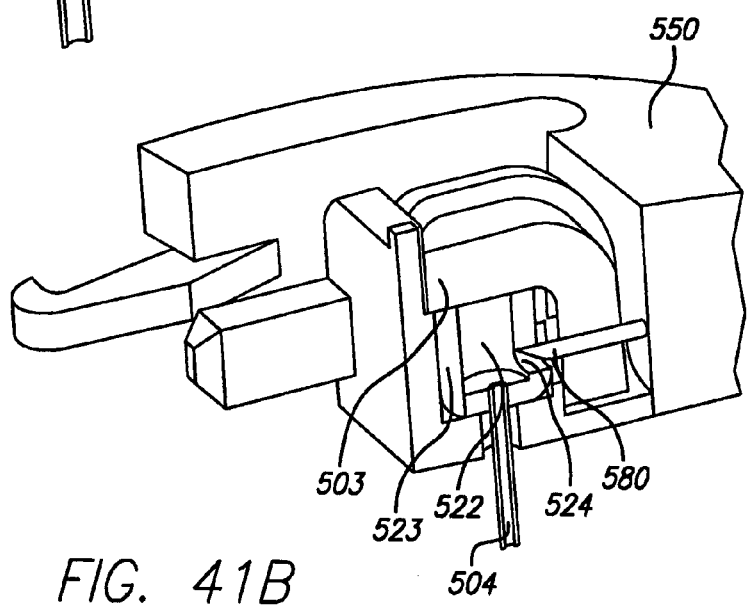

FIG. 41B illustrates the cannula device 501 that may be connected to the piercing member 580 from two directions and in which the piercing member 580 connects to the single cavity 522 from either direction through the membrane 503. When the piercing member 580 is inserted through the membrane 503 in the orthogonal direction to the direction of the cannula 504, the insertion device may enter the cavity 522 from a hole 524 in a wall 523 of the cavity 522. FIGS. 41A and B also illustrate the cannula device 501 connected at different heights in the connector 550.

Figure 42A:
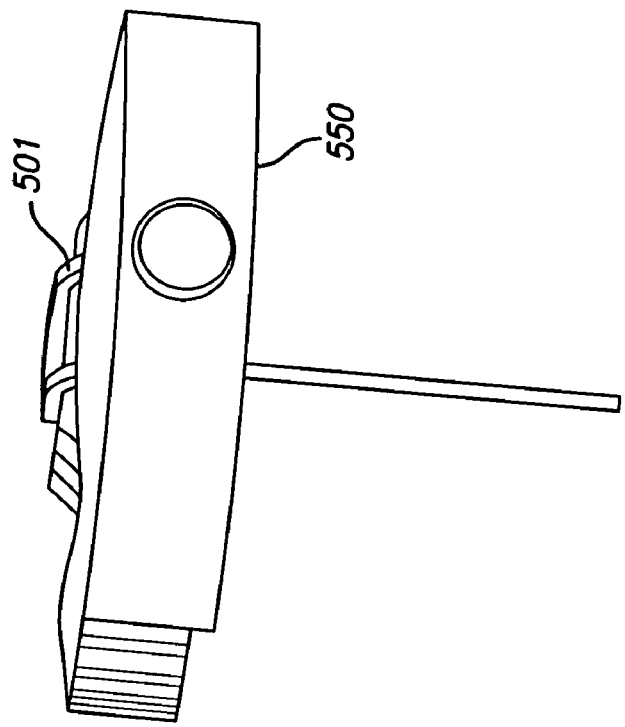
FIGS. 42A and B are side views of the embodiment shown in FIGS. 41A and B respectively.
Figure 42B:
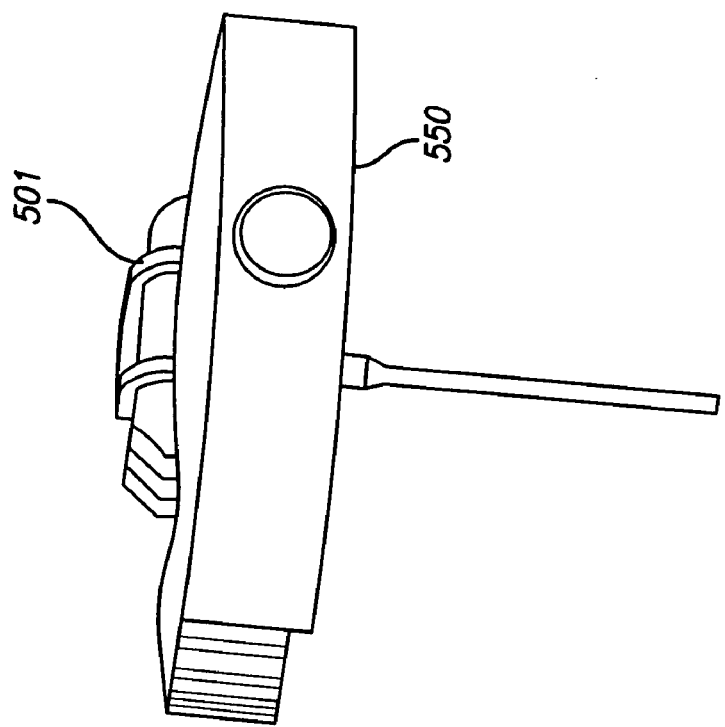

FIGS. 42A and B illustrate side views of the cannula device 501 connected to the cannula device 501 at different heights in the connector 550.

Figure 43:
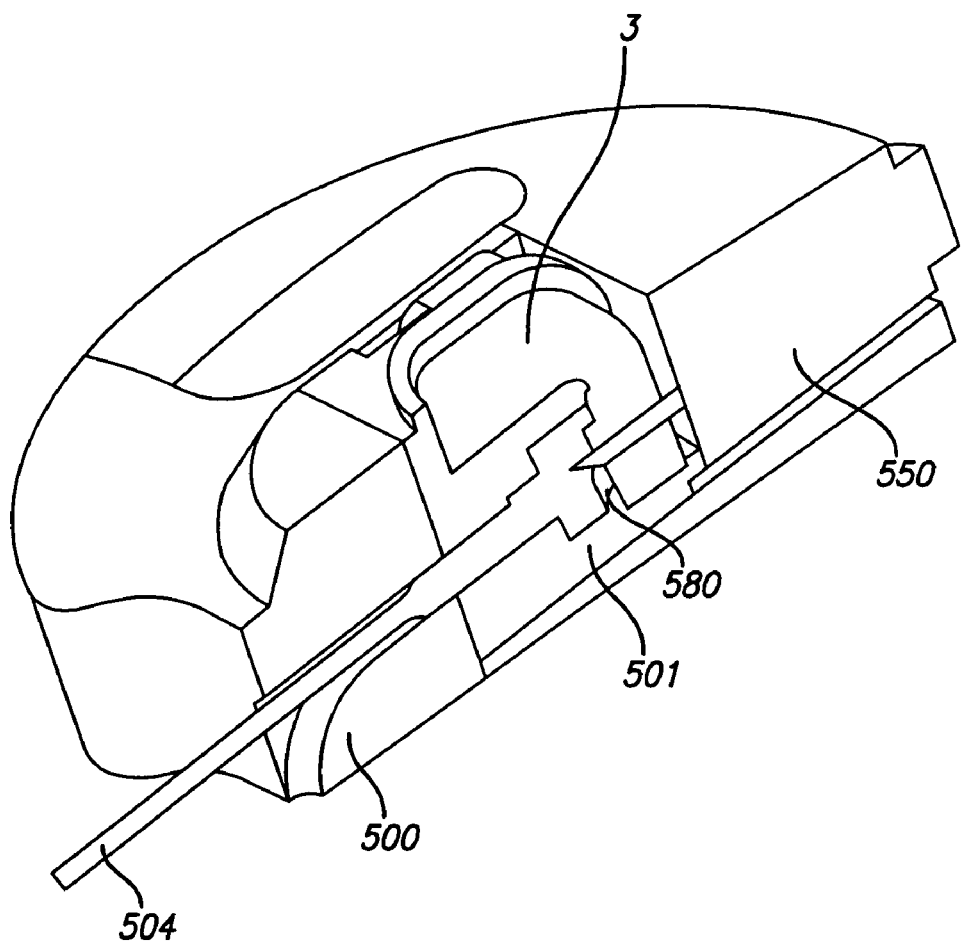
FIG. 43 is a sectional view of an embodiment of the cannula device of the present invention showing the connector in communication with the cannula.

FIG. 43 illustrates the connector 550 connected to the cannula device 501 and the cannula device 501 may be mounted in a base part 500. As shown, the connector 550 is connected in a direction parallel to the main plane of the base part 500. The connector 550 includes the piercing member 580 that is shown connecting through the membrane 503 directly with the cannula 504.

Figure 44:
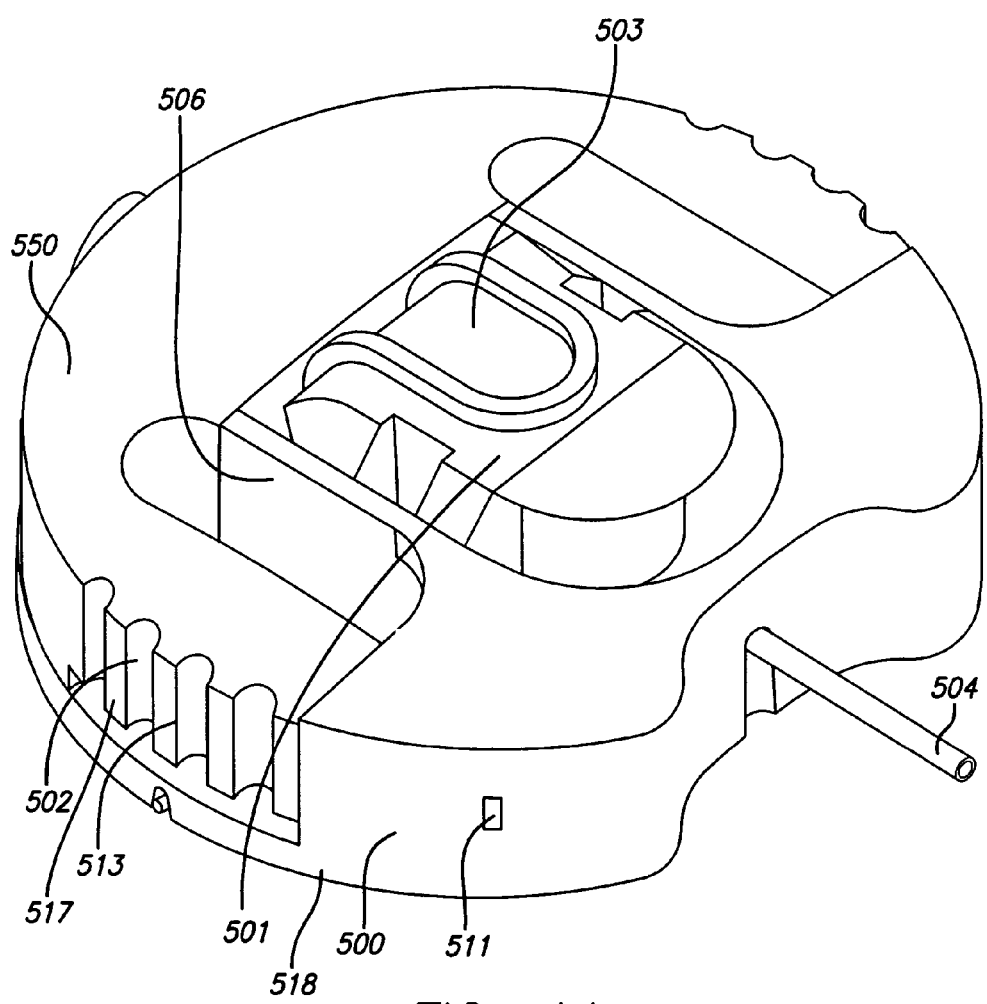
FIG. 44 is a top perspective view of the cannula device, base part and connector showing the locking members.

FIG. 44 shows the cannula device 501 connected to the connector 550 and mounted in the base part 500. The cannula 504 extends in the direction parallel to the plane 518 of the base part 500, orthogonal to the direction shown in FIGS. 42A and B. The connector 550 includes guiding arms 506 and locking arms 507. As described above, the guiding arms help to position the cannula device 501 in the base part 500 and the locking arms 507 removably lock the connector 550 with the base part 500. The locking arms 507 are shown extending into and locking with a portion of the base part 500 and into an opening 511 on the base part 500. Side portions 513 of the locking arms 507 may include ridges 517 to help the patient grip the locking arms 507 and slidably push together the connector 550 and the base part 500 to removably lock the connector 550 with the base part 500. The gripping arms 507 may also be flexible so that the patient may press inwardly on the locking arms 507 to release the locking arms from the base part 500. A portion of the membrane 503 remains exposed at the top of the cannula device 501.

Figure 45:
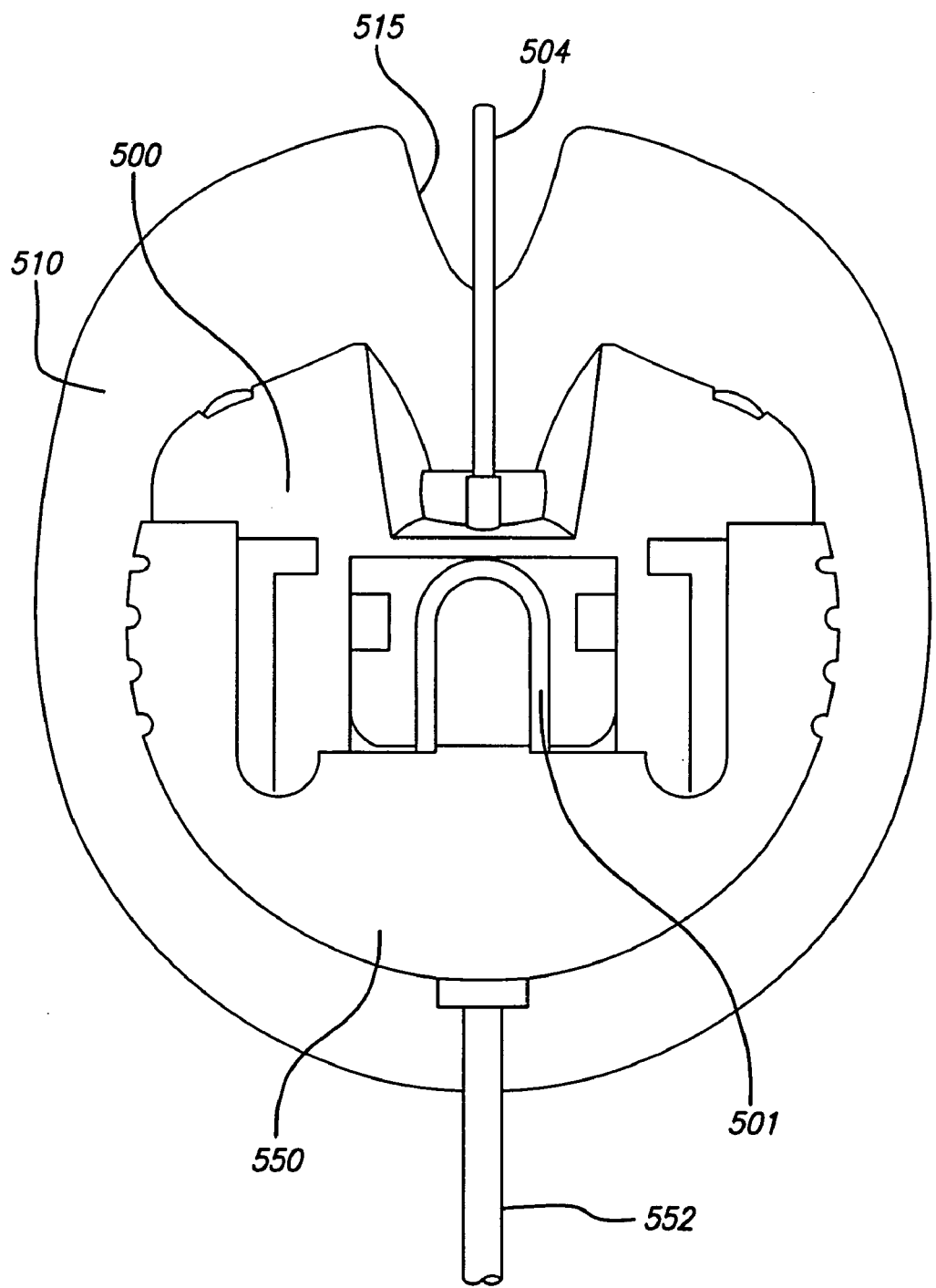
FIG. 45 is a top view of an embodiment of the present invention.

FIG. 45 shows the cannula device 501 together with the connector 550 and tubing 552 and the base part 500. An adhesive layer 510 is also shown having a cutout portion 515 for the cannula 504.

Figure 46:
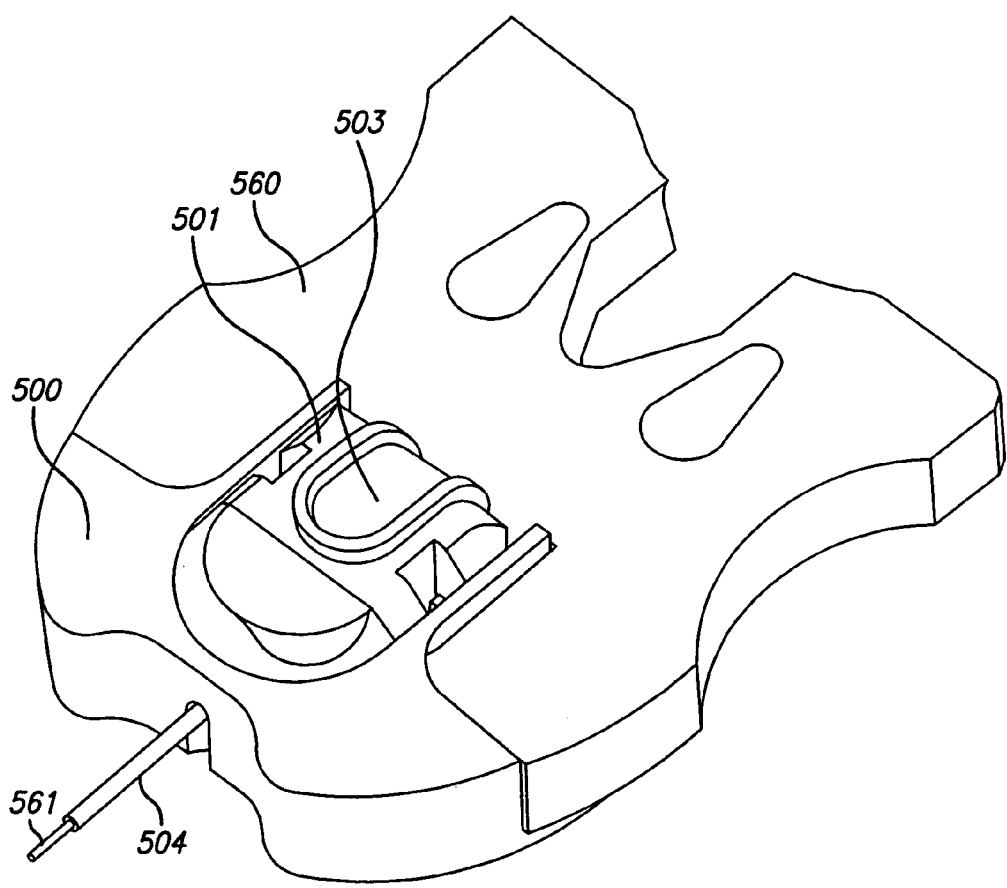
FIG. 46 is a top perspective view of the cannula device, base part and inserter.
Figure 47:
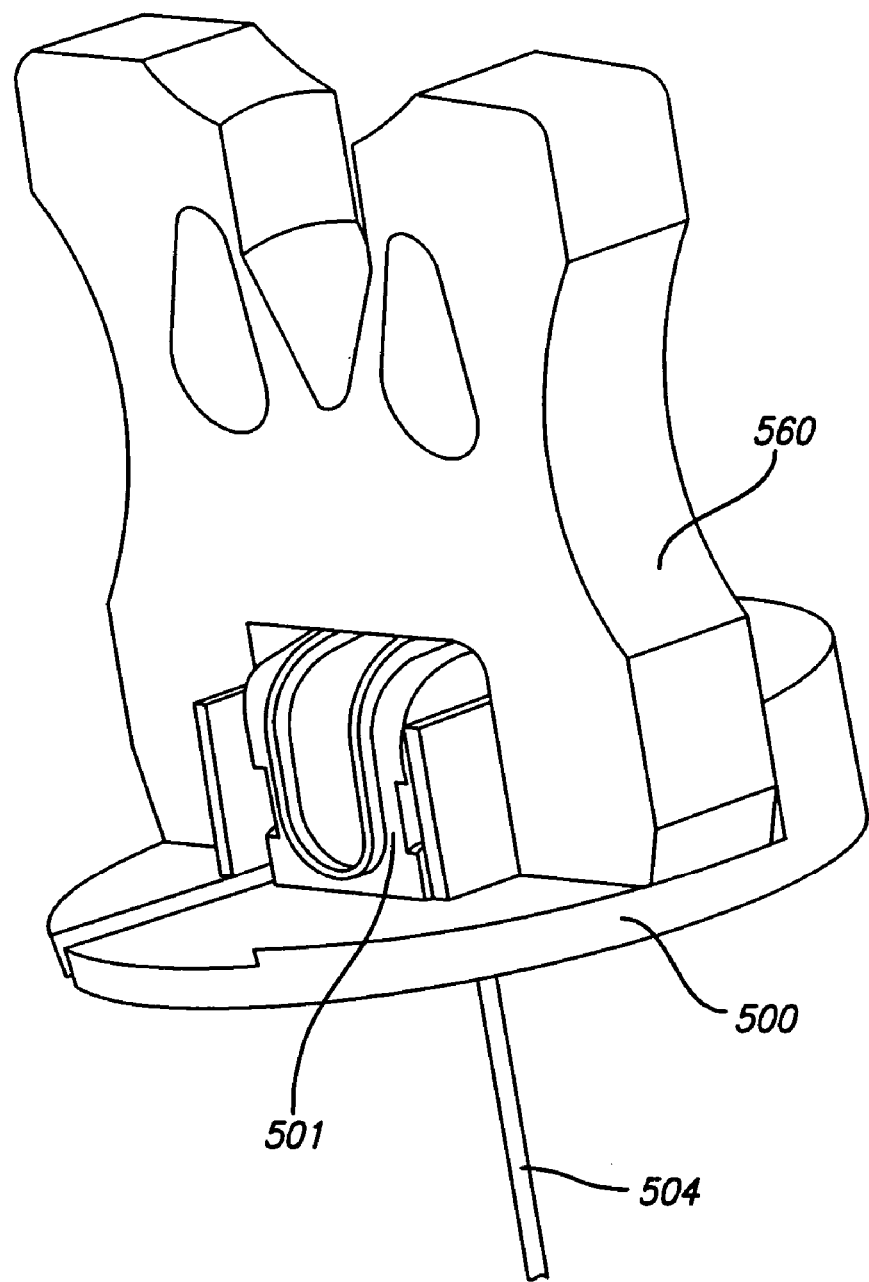
FIG. 47 is a perspective view of the cannula device and the inserter mounted on the base part in an orthogonal direction.

FIG. 46 illustrates the cannula device 501 mounted on the base part 500 with the cannula 504 extending in the direction parallel to the main plane of the base part 500. An inserter 560 may be connected to the base part 500 and the cannula device 501. A needle 561 extends from the inserter 560 though the membrane 503 of the cannula device and through the cannula 504. FIG. 47 illustrates the cannula device 501 shown in FIG. 46 may be rotated orthogonally to the direction shown in FIG. 46 and mounted to the same base part 500 shown in FIG. 46. The cannula 504 extends downward from the base part 500. The inserter 560 is also shown connected to the base part 500 and the cannula 501 in the direction orthogonal to that shown in FIG. 46.

Figure 48:
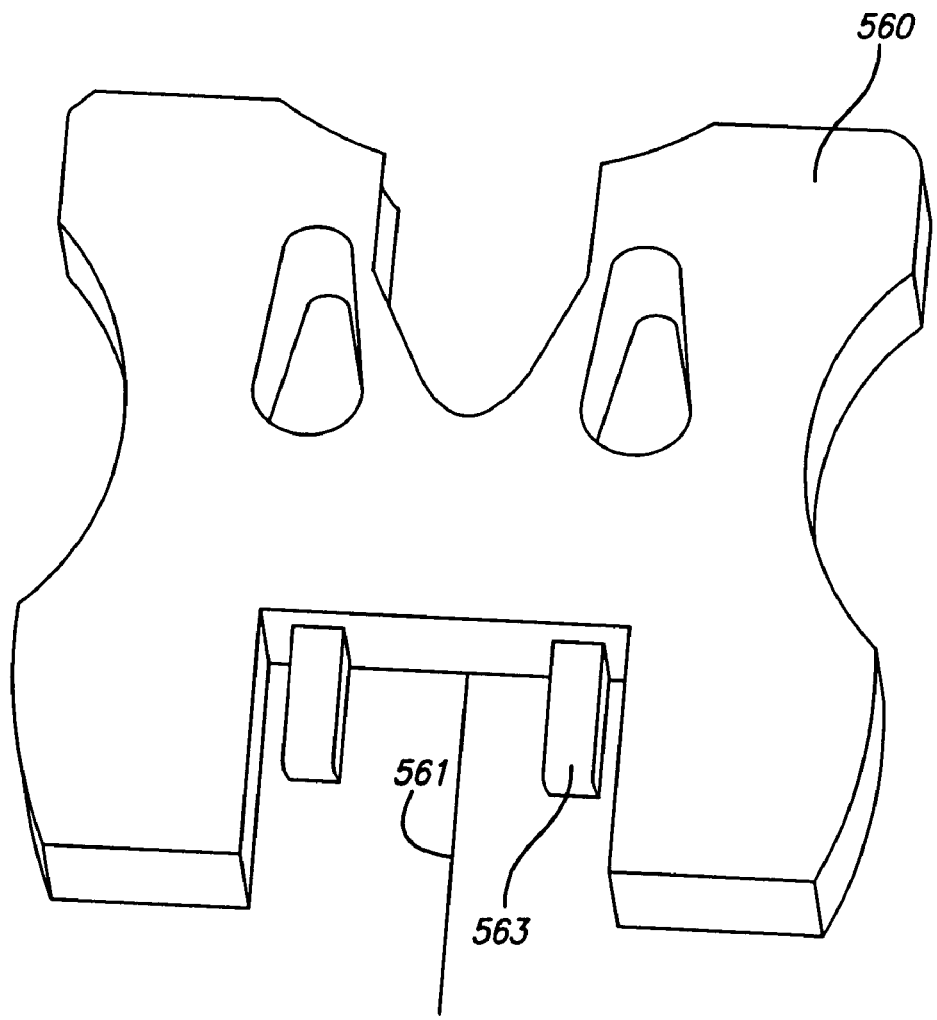
FIG. 48 shows the inserter that can be mounted on the cannula device.

FIG. 48 shows the inserter 560. The needle 561 extends from the inserter 560 and guiding arms 563 may extend on both sides of the needle 561 for slidable connection with the guiding members of the cannula device (described and shown above) to guide the inserter 560 into position in the cannula device 501.

Figure 49:
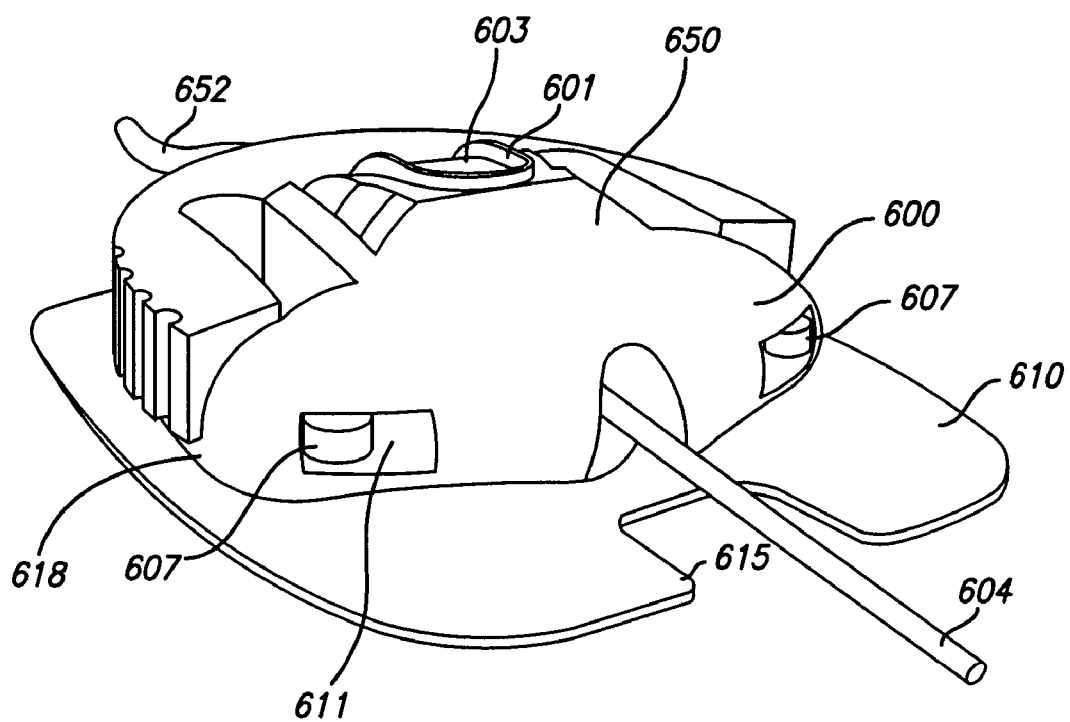
FIG. 49 is a perspective view of an embodiment of the present invention showing an angled base part.
Figure 50:
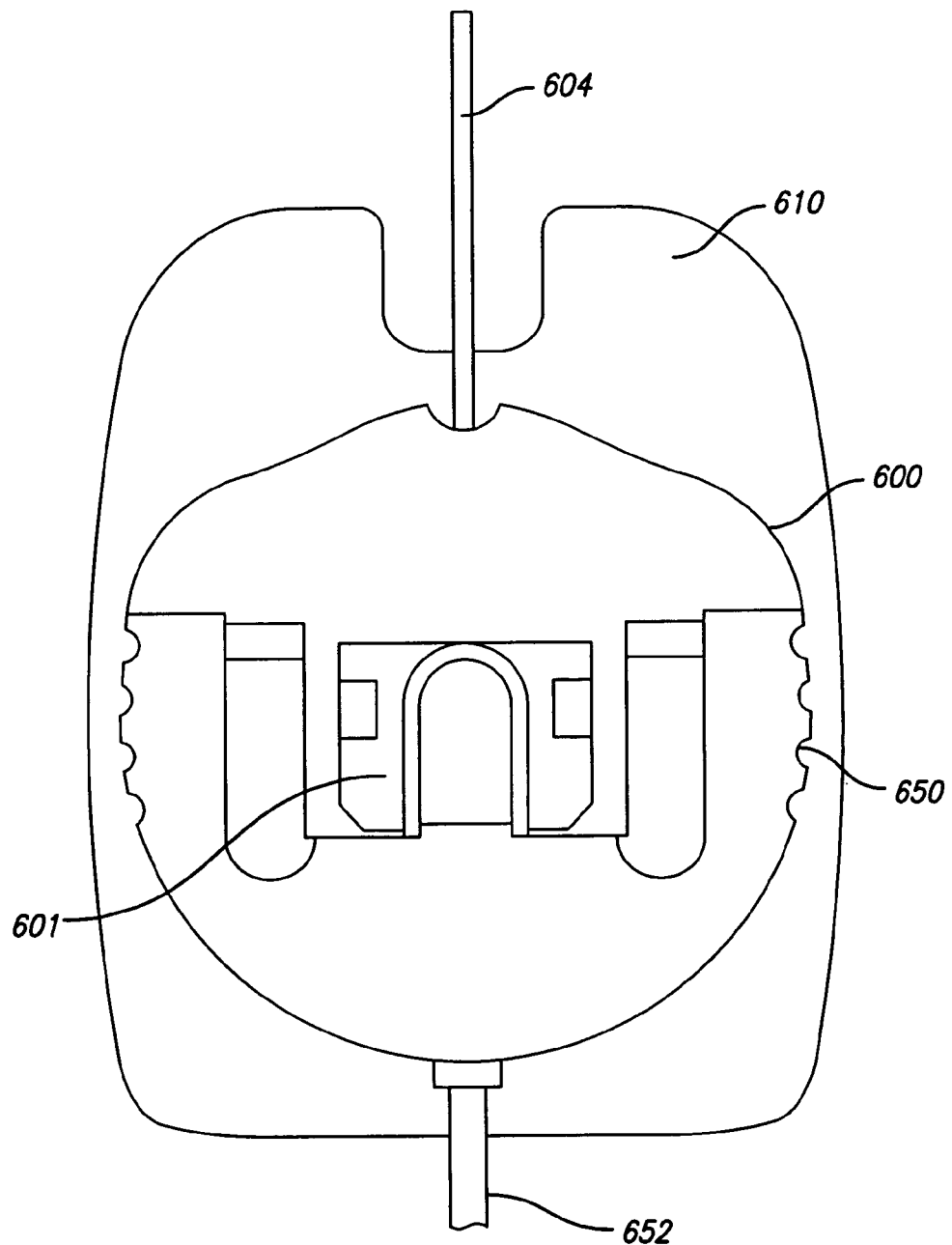
FIG. 50 is a top view of the cannula device mounted in an angled base part.
Figure 51:
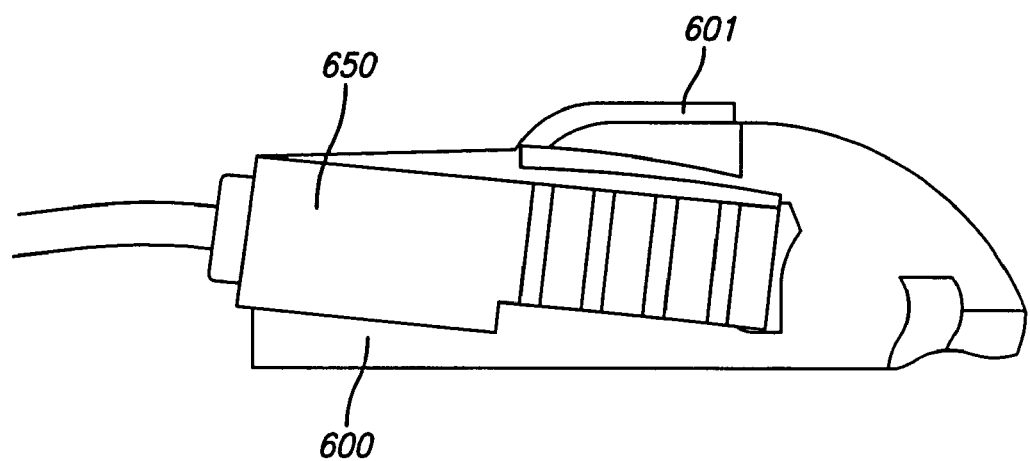
FIG. 51 is a sectional view of the embodiment shown in FIG. 50.

FIG. 49 shows an embodiment similar to the embodiment shown in FIG. 45 having an angled base part 600. The angled base part 600 can best be seen in the side view shown in FIG. 51, wherein the connector 650 is shown inserted in the base part 600 at an angle to the main plan of the base part 618. A cannula device 601 may be mounted in the base part 600 in several directions including as shown in FIG. 49 having a cannula 604 extending from the base part 600 in a direction generally parallel to the plane 618 of the base part 600. A connector 650 may be connected to the base part 600 and the cannula device 601. The connector 650 may include an piercing member 680 that inserts through the membrane 603 of the cannula device 601 for fluid connection between tubing 652 to the cannula 604 for delivery of a therapeutic substance to the skin of a patient. The connector 650 may also include locking arms 607 extending though an opening 611 in the connector 650 for removably locking the connector 650 to the base part 600. An adhesive layer 610 is also shown connected to the base part 600 and the adhesive layer 610 may include a cut out portion 615 for the cannula 604. FIG. 50 shows a top view of the embodiment shown in FIG. 49.

Figure 52:
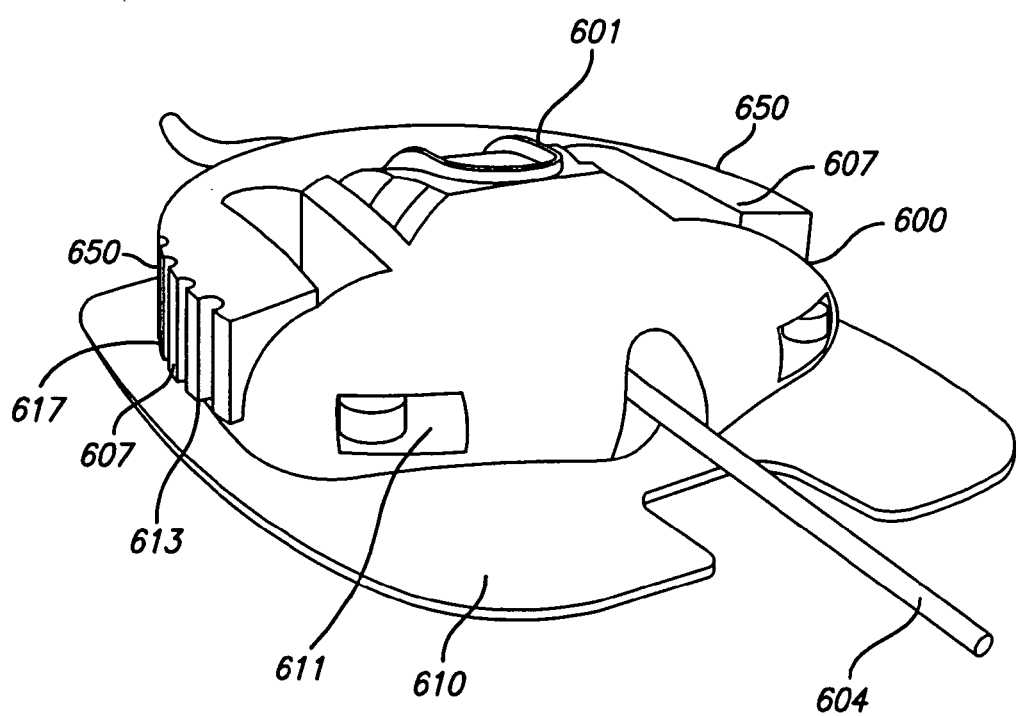
FIG. 52 is a front perspective view of the embodiment shown in FIG. 50.
Figure 53:
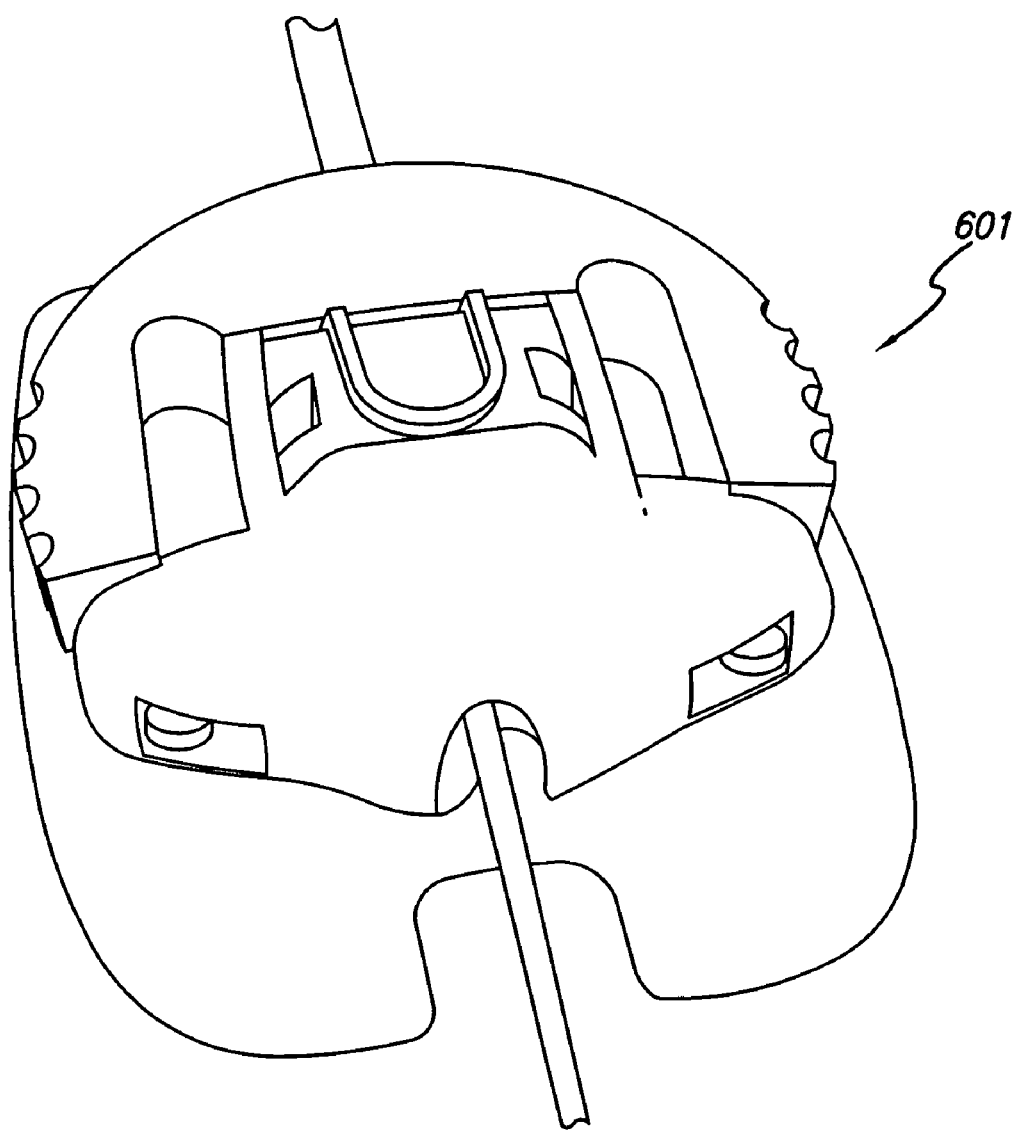
FIG. 53 is a top perspective view of the embodiment shown in FIG. 50.
Figure 54:
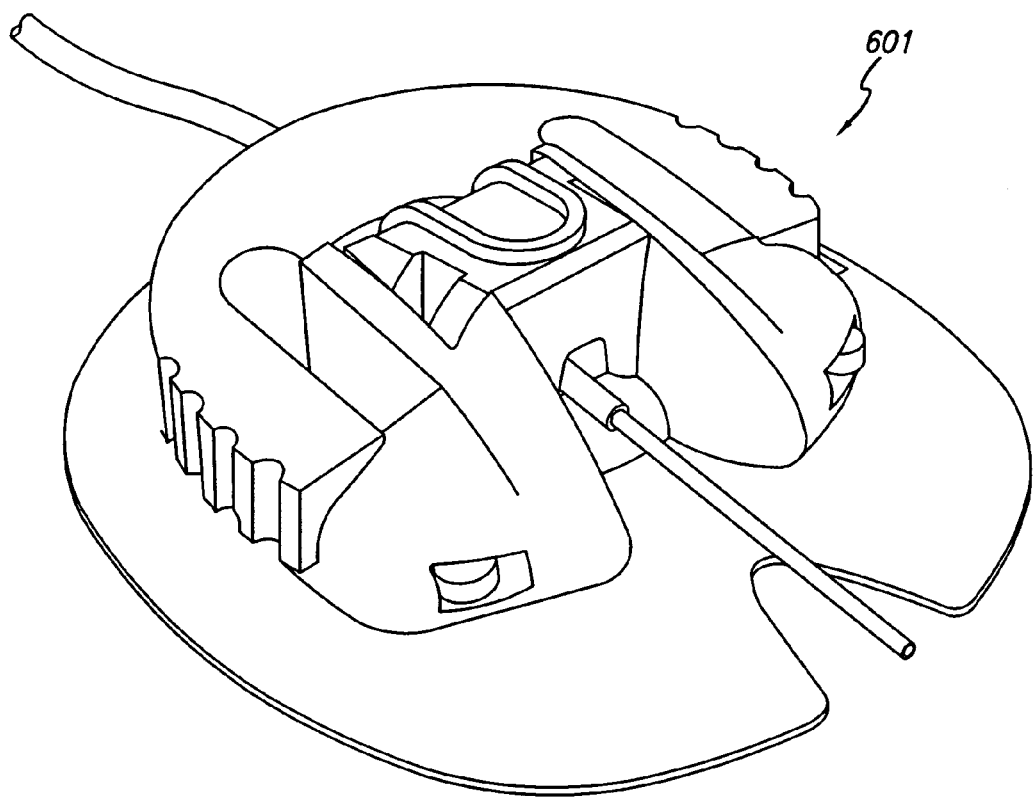
FIG. 54 is a perspective view of the embodiment shown in FIG. 50.
Figure 55:
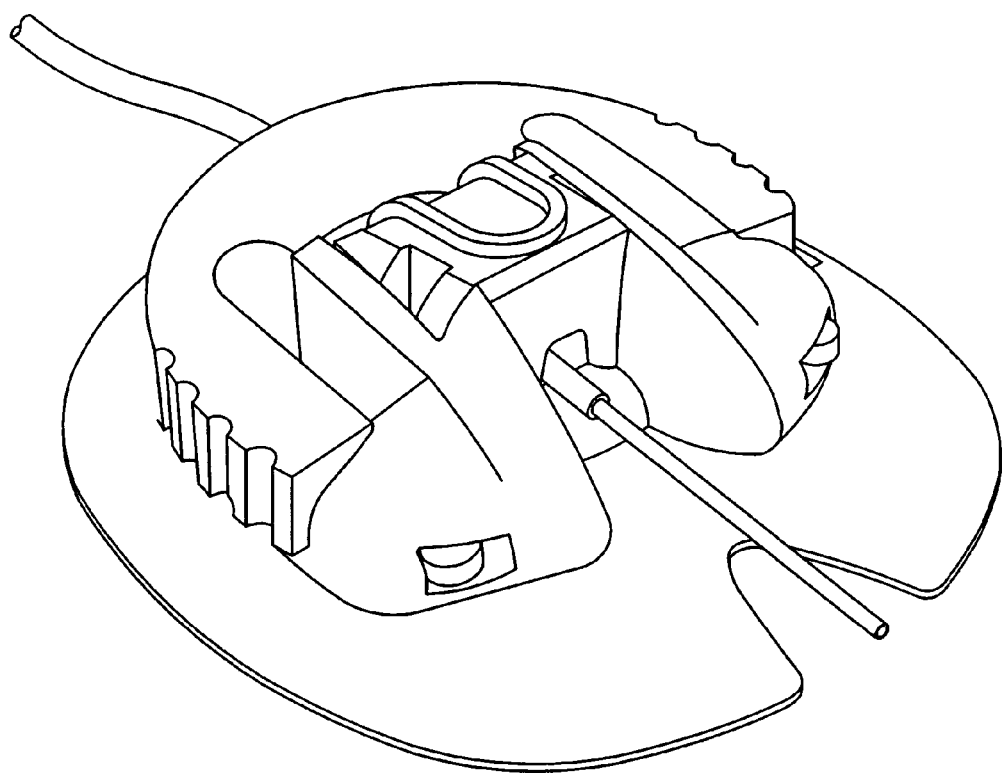
FIG. 55 is a perspective view of the embodiment shown in FIG. 50.
Figure 56:
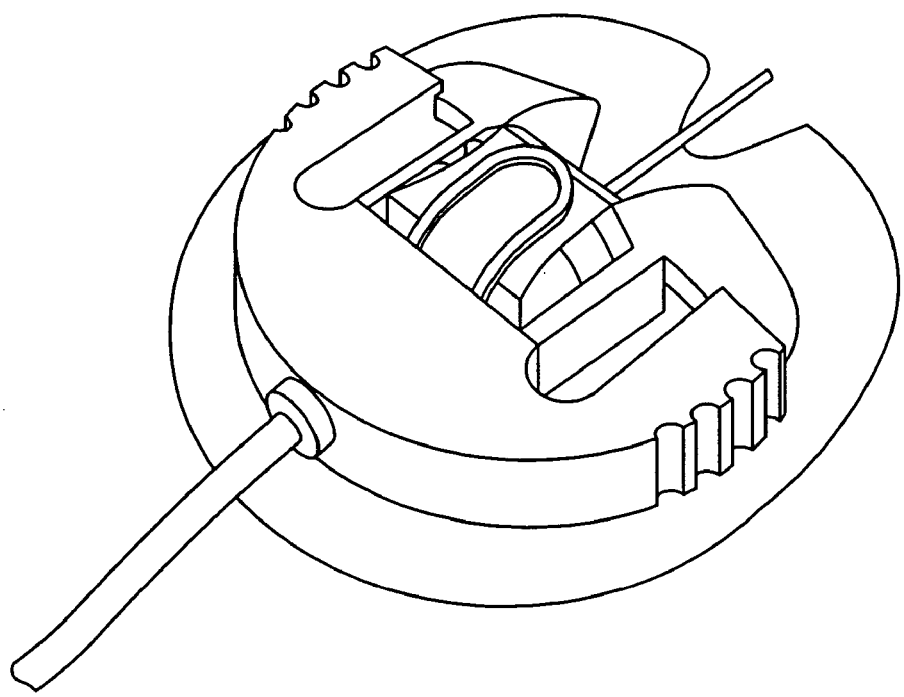
FIG. 56 is a perspective view of the embodiment shown in FIG. 50.
Figure 57:
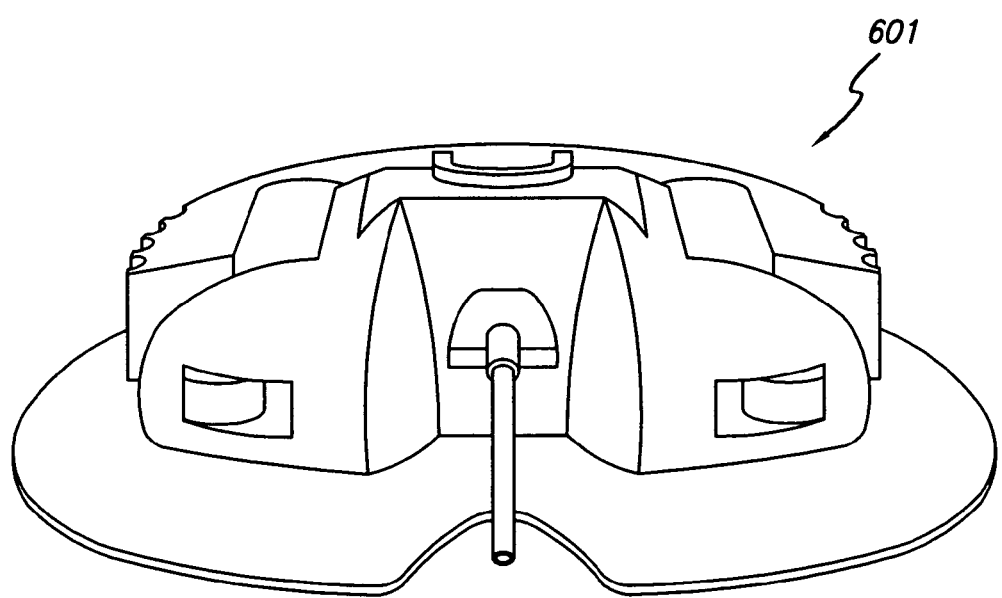
FIG. 57 is a front perspective view of the embodiment shown in FIG. 50.

FIG. 52 shows the cannula device 601 having an angled base part 600. As described above, the connector 650 may be connected with the base part 600. The connector 650 further includes guiding arms to help position the cannula device 601 in the base part 600 (not shown, described above for example in FIG. 6). Locking arms 607 removably engage the base part 600 though the opening 611 in the base part 600. The locking arms 607 are shown extending into and removably locking with a portion of the base part 600 into the opening 611 on the base part 600. Side portions 613 of the locking arms 607 may include ridges 617 to help the patient grip the locking arms and removably lock the connector 650 with the base part 600. The gripping arms 607 may also be flexible so that the patient may press inwardly on the locking arms 607 to release the locking arms 607 from the base part 600. FIGS. 53-57 illustrate perspective views of the cannula device 601 shown in FIG. 52.

Figure 58:
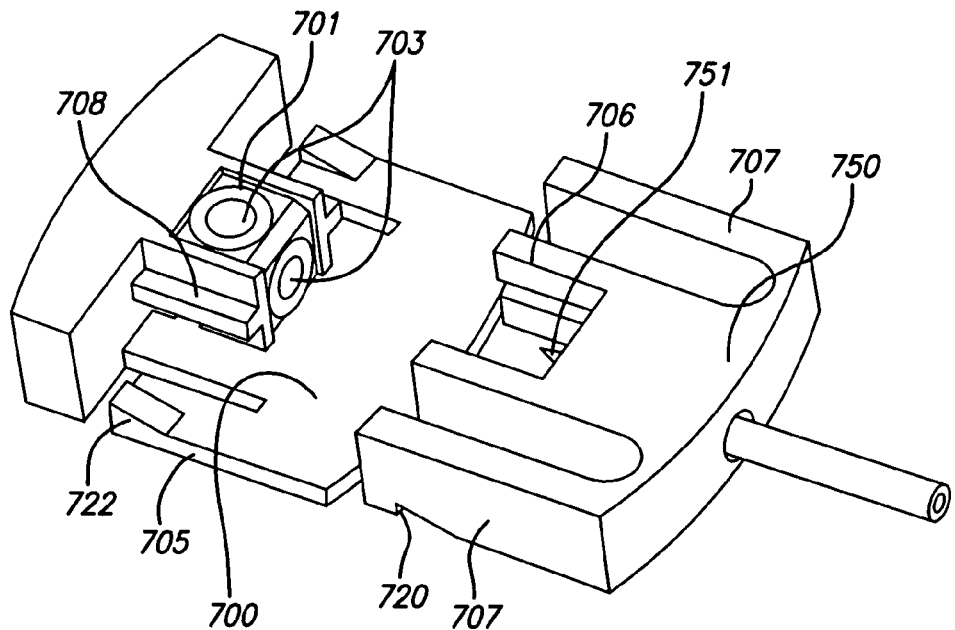
FIG. 58 is an exploded perspective view of another embodiment of the present invention.
Figure 59:
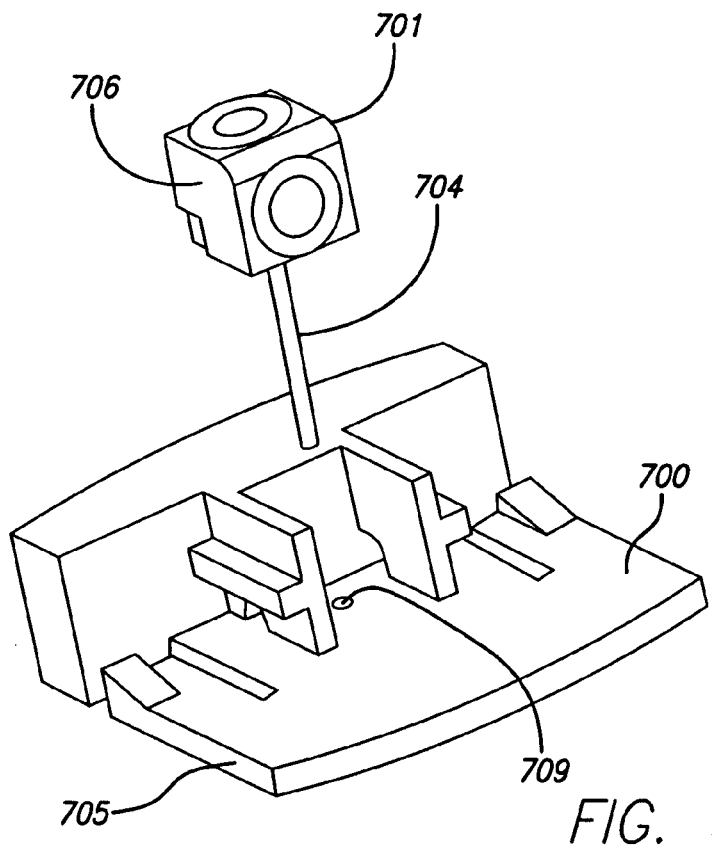
FIG. 59 is an exploded perspective view of the cannula device and the base part shown in FIG. 58.

FIGS. 58-65 illustrate another preferred embodiment of the present invention. In FIGS. 58 and 59, a cannula device 701 is cubically shaped and is positioned in a base part 700 so that a cannula 704 of the cannula device 701 is essentially orthogonal to a main surface 705 of the base part 700. As described above, other shapes for the cannula device 701 are possible. The cannula device 701 can receive both an inserter needle of an inserter (as described above and shown, for example, in FIG. 4) and a connector 750 having a cannula 751 from a direction being essentially parallel with the cannula 704. The cannula device 701 includes at least one membrane 703 through which the inserter needle or the piercing member 751 inserts. FIGS. 58 and 59 illustrate the cannula device 701 having two membranes 703, although one of skill in the art will understand that more membranes 703 are possible. A protective member or inserter may also be used with the cannula device 701 and base part 700 in place of the connector 750 as described above.

Further FIGS. 58 and 59 show that it is possible for the connector 750 to connect with the base part 700 from a direction being essentially orthogonal to the direction of the cannula 704 and the piercing member 751 can pierce the membrane 703 from a direction orthogonal to the direction of the connector 750 shown in FIG. 58. The cannula device 701 is constructed in such a manner that the cannula 704 is in fluid communication with the piercing member 751 when received regardless of the direction from which the piercing member 751 is received. In the embodiment shown in FIGS. 58 and 59, the cannula device includes a cavity 706 similar to the cavity 6 described above for the cannula device 1. Alternatively, the cannula device 701 may not include a cavity 706 wherein the piercing member 751 fluidly connects with the cannula 704, similar to the reception of the piercing member without having a cavity 706, similar to the device described above in FIG. 41B.

FIGS. 58 and 59 also illustrate an alternative mechanism for removable locking the connector 750 with the base part 700. The connector 750 includes locking arms 707 for removably locking the base part 700 to the connector 750. The locking arms 707 further include notched projections 720 for engaging angled projections 722 on the base part 700. The notched projections 720 of the connector 750 slidably engage the angled projections 722 of the base part 700. The projections 720 snap together with the projections 722 and the projections 720 fit into a gap in the base part 700 to releasably lock the base part 700 to the connector 750. The base part 700 may be released from the connector 750 by pressing on the projections 720. The connector 750 may also include guiding arms 706 to slidably engage guiding members 705 of the cannula device 701. Of course, alternative locking means may be used to releasably engage the base part 700 with the connector 751.

Figure 60:
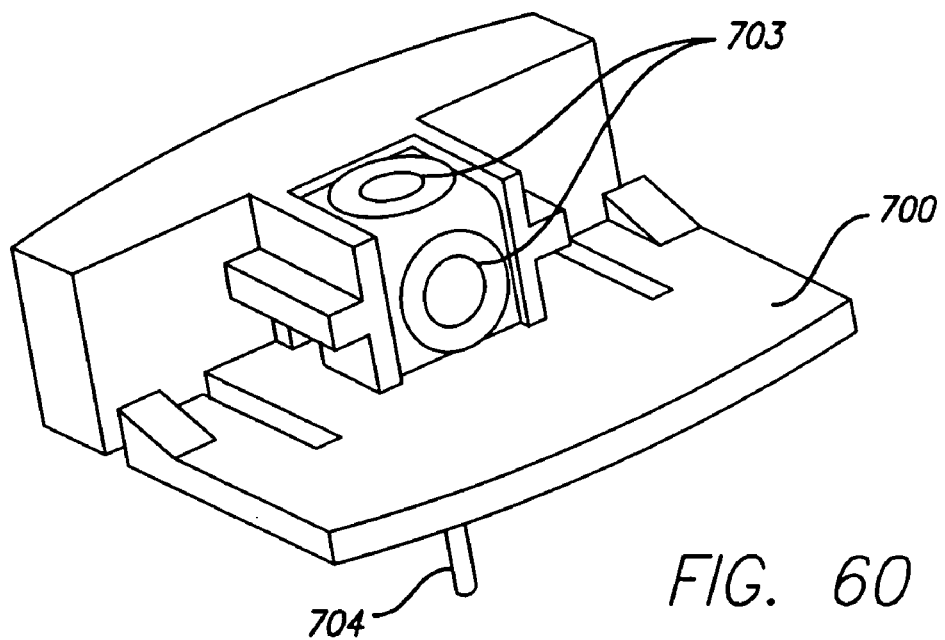
FIG. 60 is a perspective view of the embodiment shown in FIG. 59 with the cannula device in an orthogonal direction.

FIGS. 58-60 illustrate the cannula 704 extending essentially perpendicular to the main surface 705 of the base part 700 so that the cannula 704 penetrates the patient's skin essentially perpendicular to the main surface 705 of the base part 700. The base part 700 includes an opening 709 through which the cannula 704 of the cannula device 701 may extend.

Figure 61:
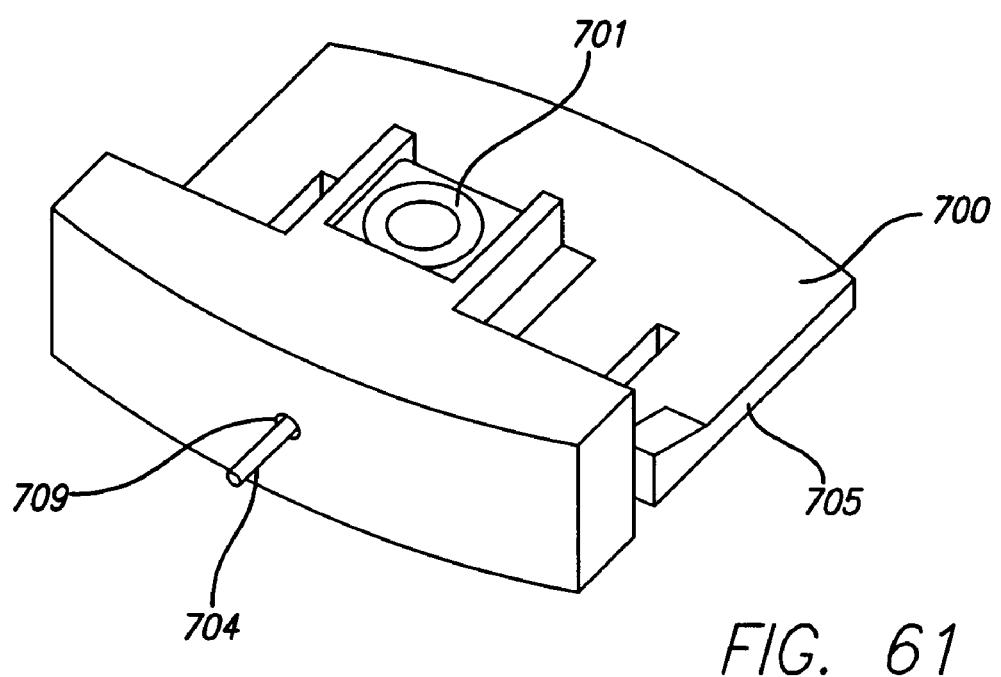
FIG. 61 is a perspective view of the embodiment shown in FIG. 60 with the cannula device in a parallel direction.
Figure 62:
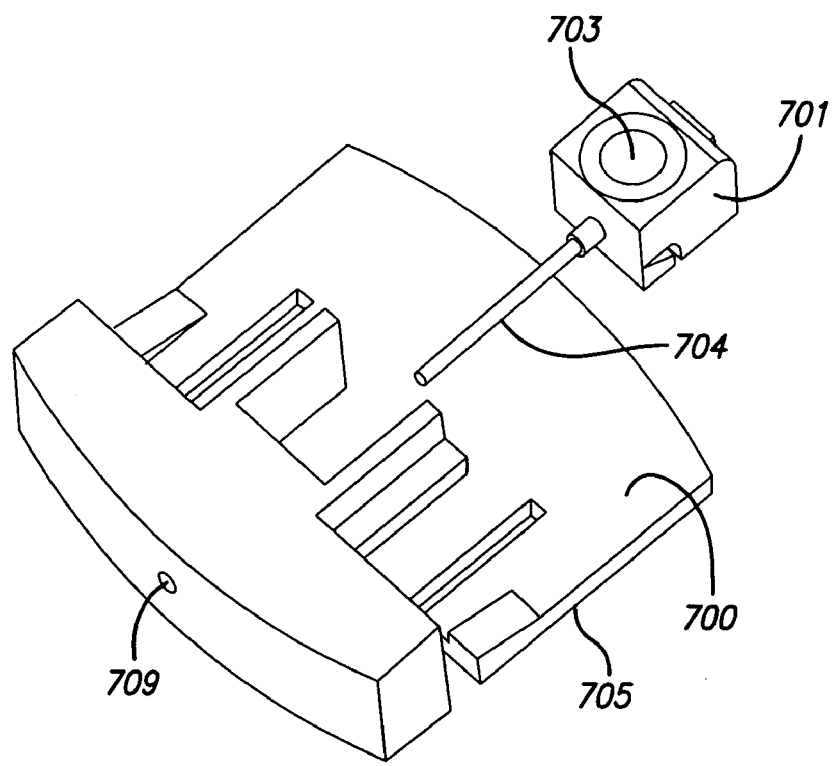
FIG. 62 is an exploded perspective view of the embodiment shown in FIG. 61.
Figure 63:
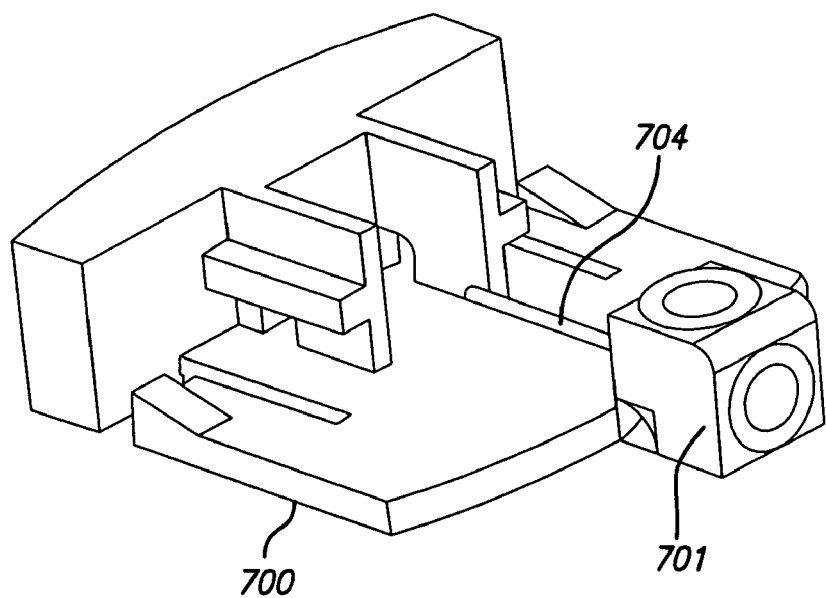
FIG. 63 is an exploded perspective view of the embodiment shown in FIG. 61.

FIG. 61 illustrates the cannula 704 extending essentially parallel to the main surface 705 of the base part 700 through the opening 709 in the base part 700. FIGS. 62 and 63 illustrate the cannula device 701 prior to connection with the base part 700 where the cannula 704 will extend through the opening 709 essentially parallel to the main surface 705 of the base part 700.

Figure 64:
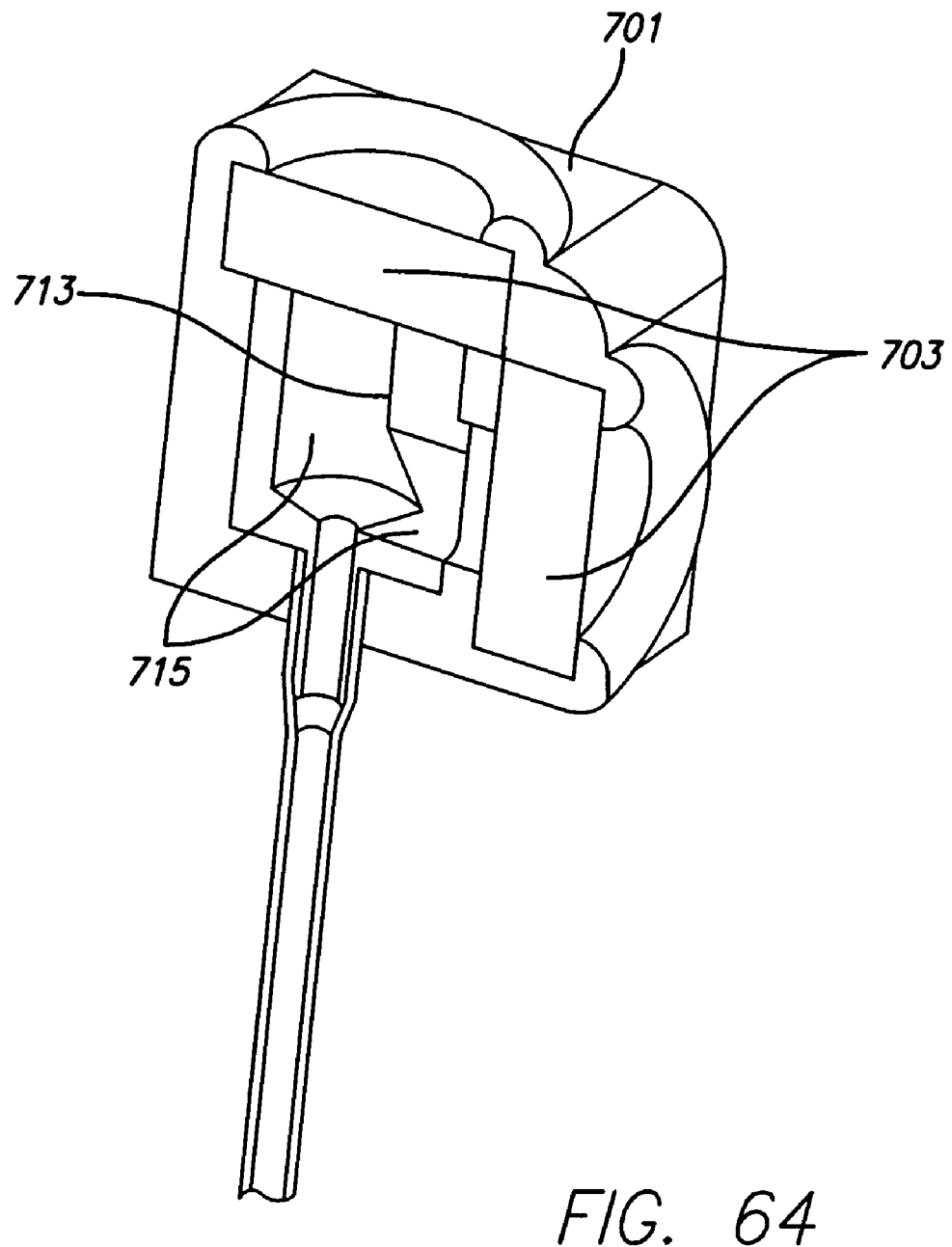
FIG. 64 is a sectional view of the cannula device shown in FIG. 58.

FIG. 64 shows an example of an interior portion 713 of the cannula device 701. In this embodiment, the piercing member 751 will insert directly into a channel 715 without having a cavity for fluidly connecting the piercing member 751 with the cannula 704 as described above. The cannula connector 751 can pierce the membranes 703 from either direction shown and directly enter the channels 715 to fluidly connect with the cannula 704.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A cannula device for mounting to a base part of an infusion set, said device comprising:
a housing and at least one membrane adapted to receive a piercing member; and
a cannula mounted to said housing; wherein said cannula device is adapted to removable attach to said base part in a first attachment configuration or a second attachment configuration and wherein said cannula device can receive said piercing member of a connector from a first receiving direction in the first attachment configuration and from a second receiving direction in the second attachment configuration, the second receiving direction being different from said first direction providing fluid communication between said piercing member and said cannula.

2. The cannula device according to claim 1 wherein said at least one membrane further comprises a first membrane oriented generally perpendicular to said first receiving direction and a second membrane oriented generally perpendicular to said second receiving direction.

3. The cannula device according to claim 1 wherein said at least one membrane further comprises a single membrane oriented to intersect both said first and second receiving directions.

4. The cannula device according to claim 1 wherein an angle between the first and the second receiving directions is at least 45°.

5. The cannula device according to claim 4 wherein said angle is at least 60°.

6. The cannula device of claim 4 wherein said angle is at least 75°.

7. The cannula device of claim 4 wherein said angle is at least 85°.

8. The cannula device according to claim 1 wherein the cannula device is adapted to receive the piercing member from a third direction.

9. The cannula device according to claim 8 wherein an angle between said first direction and said third direction is between about 5° and about 175°.

10. The cannula device of claim 8 wherein an angle between said first direction and said third direction angle is between about 30° and about 150°.

11. The cannula device according to claim 1 wherein said at least one membrane is self-sealing.

12. The cannula device according to claim 11, wherein said at least one membrane is made of silicone.

13. The cannula device according to claim 1, wherein said housing defines a plurality of cavities.

14. The cannula device according to claim 1 wherein said cannula device has a generally cylindrical shape.

15. The cannula device according to claim 1 wherein said housing and said at least one membrane together define at least one cavity.

16. The cannula device according to claim 1 wherein said cannula device can be attached to said base part at different levels with respect to said base part.

17. The cannula device according to claim 1 wherein said base part comprises attachment members adapted for removable attaching said cannula device to said base part in more than one direction with respect to said base part.

18. The cannula device according to claim 1 comprises guiding members adapted to engage with guiding members of said cannula device for positioning said cannula device on said base part.

19. The cannula device according to claim 18, wherein the guiding members guide both the assembling of the cannula device with a base part and coupling to the base part one of a connector and an inserter.

20. The cannula device according to claim 1 further comprising locking members.

21. The cannula device according to claim 20 wherein said locking members removable connect said cannula device to said base part.

22. The cannula device according to claim 1 wherein said locking members removable connect a connector to said base part.

23. The cannula device according to claim 1 wherein said cannula device is selectively rotatable relative to said base part.

24. The cannula device according to claim 23 further comprising hinges for attaching said cannula device to said base part.

25. A cannula device for mounting to a base part of an infusion set, said device comprising:
 a housing and at least one membrane adapted to receive a piercing member of a connector; and
 a cannula mounted to said housing;
 wherein said housing is adapted to be repositionable relative to said base part in more than one orientation with respect to said base part.

26. The cannula device of claim 25 wherein said housing further comprises guiding members for position said device on said base part.

27. The cannula device of claim 26 wherein said housing is repositionable at different levels with respect to said base part for changing the distance said cannula is inserted into the skin of a patient.

28. The cannula device of claim 26 wherein said housing is repositionable within said housing in at least a first direction and a second direction wherein an angle between said first direction and said second direction is at least 45°.

* * * * *